(12) United States Patent
Vaka et al.

(10) Patent No.: US 11,439,585 B2
(45) Date of Patent: *Sep. 13, 2022

(54) PROGRAMMABLE PHARMACEUTICAL COMPOSITIONS FOR CHRONO DRUG RELEASE

(71) Applicant: Amneal Complex Products Research LLC, Bridgewater, NJ (US)

(72) Inventors: Siva Ram Kiran Vaka, Piscataway, NJ (US); Paras Jariwala, Somerset, NJ (US); Jaydeep Vaghashiya, Franklin park, NJ (US); Atsawin Thongsukmak, Basking Ridge, NJ (US); Dipen Desai, Whippany, NJ (US); Wantanee Phuapradit, Montville, NJ (US); Navnit H. Shah, Monmouth Junction, NJ (US)

(73) Assignee: Amneal Complex Products Research LLC, Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/465,972

(22) Filed: Sep. 3, 2021

(65) Prior Publication Data

US 2021/0393512 A1 Dec. 23, 2021

Related U.S. Application Data

(63) Continuation of application No. 17/198,366, filed on Mar. 11, 2021, now Pat. No. 11,154,494, which is a (Continued)

(51) Int. Cl.
*A61K 9/00* (2006.01)
*A61K 9/20* (2006.01)
(Continued)

(52) U.S. Cl.
CPC .......... *A61K 9/0004* (2013.01); *A61K 9/2027* (2013.01); *A61K 9/2031* (2013.01);
(Continued)

(58) Field of Classification Search
None
See application file for complete search history.

(56) References Cited

U.S. PATENT DOCUMENTS 5,156,850 A 10/1992 Wong et al.
7,521,067 B1 4/2009 Greerke et al.
(Continued)

FOREIGN PATENT DOCUMENTS

EP 0768867 4/1997
WO WO 1995/34285 12/1995

OTHER PUBLICATIONS

Kurlan R, et al., Clonidine and methylphenidate were effective for attention deficit hyperactivity disorder in children with comorbid tics, Evidence-based medicine, BMJ Group, UK, US, vol. 7, No. 5, Sep. 1, 2002, p. 157 XP002724188, ISSN: 1356-5524, DOI: 10.1136/EBM.7.5.157.

(Continued)

*Primary Examiner* — Melissa L Fisher
*Assistant Examiner* — Barbara S Frazier
(74) *Attorney, Agent, or Firm* — Amneal Complex Products Research LLC; Vandana Awasthi

(57) ABSTRACT

The present disclosure provides programmable osmotic-controlled oral compositions providing delayed release of a therapeutically acceptable amount of a drug. The programmable osmotic-controlled compositions of the disclosure provide a lag time that is independent of the presence or absence of food, type of food, pH, gastric emptying, gastric motility, and volume and viscosity of gastric fluid. The compositions of the disclosure can be programmed to pro- (Continued)

Figure 1:
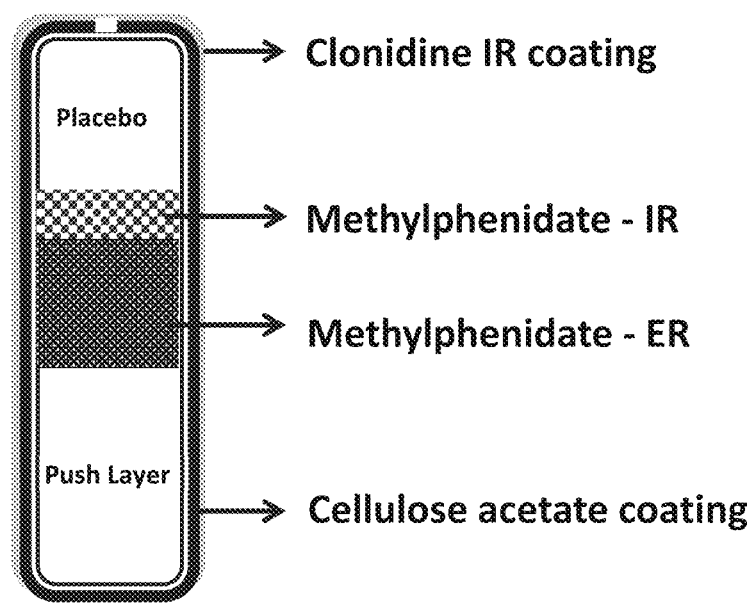

vide a desired and precise lag time, and release drug, after the lag time, at a rhythm, e.g., that matches the human circadian rhythm of a condition's symptoms and/or of the individual being treated in the application of the therapy to optimize therapeutic outcome and minimize side effects.

20 Claims, 27 Drawing Sheets

Related U.S. Application Data continuation of application No. 17/021,124, filed on Sep. 15, 2020, now Pat. No. 10,980,738, which is a continuation of application No. 16/809,714, filed on Mar. 5, 2020, now Pat. No. 10,898,431, which is a continuation-in-part of application No. PCT/US2019/020815, filed on Mar. 5, 2019.

(60) Provisional application No. 62/760,771, filed on Nov. 13, 2018, provisional application No. 62/638,667, filed on Mar. 5, 2018.

(51) Int. Cl.
    *A61K 31/4458*     (2006.01)
    *A61K 31/138*     (2006.01)
    *A61K 31/155*     (2006.01)
    *A61K 31/165*     (2006.01)
    *A61K 31/4045*     (2006.01)
    *A61K 31/4178*     (2006.01)
    *A61K 31/573*     (2006.01)
    *A61K 45/06*     (2006.01)
    *A61K 47/10*     (2017.01)

(52) U.S. Cl.
CPC .......... *A61K 9/2054* (2013.01); *A61K 9/2086* (2013.01); *A61K 31/138* (2013.01); *A61K 31/155* (2013.01); *A61K 31/165* (2013.01); *A61K 31/4045* (2013.01); *A61K 31/4178* (2013.01); *A61K 31/4458* (2013.01); *A61K 31/573* (2013.01); *A61K 45/06* (2013.01); *A61K 47/10* (2013.01)

(56) References Cited

U.S. PATENT DOCUMENTS

| | | | | |
|---|---|---|---|---|
| 10,898,431 | B2* | 1/2021 | Vaka | A61K 47/10 |
| 10,980,738 | B2* | 4/2021 | Vaka | A61K 31/573 |
| 11,000,471 | B2* | 5/2021 | Vaka | A61K 9/2031 |
| 11,154,494 | B2* | 10/2021 | Vaka | A61K 9/2086 |
| 11,166,906 | B2* | 11/2021 | Vaka | A61K 31/135 |
| 2001/0012847 | A1 | 8/2001 | Lam et al. | |
| 2010/0112052 | A1 | 5/2010 | Chen et al. | |

OTHER PUBLICATIONS

Robinson, et al., The osmotic coefficients of some organic compounds in relation to their chemical constitution, Trans. Faraday Soc., vol. 38, Jan. 1, 1942, pp. 63-70, XP5589305, Figure 1, table V.

International Search Report and Written Opinion dated May 28, 2019 in International Application No. PCT/US2019/020815.

* cited by examiner

PROGRAMMABLE PHARMACEUTICAL COMPOSITIONS FOR CHRONO DRUG RELEASE

1. RELATED APPLICATIONS

This application is a continuation of U.S. application Ser. No. 17/198,366, filed Mar. 11, 2021, which is a continuation of U.S. application Ser. No. 17/021,124, filed Sep. 15, 2020, now U.S. Pat. No. 10,980,738, which is a continuation of U.S. application Ser. No. 16/809,714 filed Mar. 5, 2020, now U.S. Pat. No. 10,898,431, which is a continuation-in-part of International Application No. PCT/US2019/020815, filed Mar. 5, 2019, which claims priority to U.S. Provisional Patent Application Nos. 62/638,667, filed Mar. 5, 2018, and 62/760,771, filed Nov. 13, 2018, the disclosures of which are hereby incorporated by reference herein in their entireties.

2. TECHNICAL FIELD

The presently disclosed subject matter relates to programmable osmotic-controlled oral compositions providing delayed controlled release of a drug. The osmotic-controlled oral compositions of the disclosure can be programmed to provide a desired and precise lag time, thereby releasing a drug, after the lag time, at a rhythm, e.g., that matches the human circadian rhythm of a condition's symptoms and/or of the individual being treated in the application of the therapy, to optimize therapeutic outcome and minimize side effects. The osmotic-controlled oral compositions of the disclosure can be programmed to provide a desired and precise lag time, and a desired release profile after the lag time to provide therapeutic plasma concentrations of drugs, even while releasing the drugs in the lower portions of the GI tract. The programmable osmotic-controlled compositions of the disclosure can provide a lag time that is substantially independent of the presence or absence of food, type of food, pH, gastric emptying, and volume and viscosity of immediate microenvironment of drug release.

3. BACKGROUND

Attention deficit disorders, e.g., ADHD, are among the most common developmental disorders in children and are characterized by symptoms such as impulsiveness, hyperactivity, and inattentiveness. Hyperactivity is common in children with ADHD. Stimulant medications are widely used as a pharmacological treatment for ADHD/ADD. Stimulant medications approved by the FDA include methylphenidate, and salts and isomers of amphetamine. One major challenge of treating ADHD and other stimulant-responsive conditions is delivering and maintaining an effective stimulant concentration in patients, particularly children, throughout the day, in particular during the morning hours when cognitive abilities and concentration are needed for school, work, or extracurricular activities, and during the late afternoon or evening when students often do homework. Early morning symptom control, including getting the children ready for school, is a major challenge for parents and caregivers of children suffering from ADHD/ADD. Typically, stimulant-based medications are dosed two hours prior to beginning an early morning routine, with an onset of treatment effect usually about two hours after administration. Such medications require twice-daily administration and cause compliance issues. JORNAY PM™, a commercially available product of methylphenidate (Ironshore Pharmaceuticals and Development Inc., NDA #209311), has been approved by the FDA for the treatment of ADHD in patients six years and older. JORNAY PM™ is a methylphenidate formulation that is to be administered in the evening in an attempt to improve ADHD symptoms in the early morning and throughout the day. However, drug release from the formulation can be affected by pH, food, and gastric transit time, with a potential for variable drug release during the night and predawn hours, leading to insomnia.

Extended release of a drug from an oral dosage form can be affected by hydrodynamic conditions in the GI tract that are associated with, e.g., pH and presence of food in the stomach. Osmotic-controlled oral drug delivery systems (OROS) known in the art provide controlled extended release of a drug with zero-order kinetics. The OROS drug delivery system is an advanced drug delivery technology that uses osmotic pressure as a driving force for controlled delivery of active agents. Such systems provide a constant release rate of a drug over an extended period of time. OROS delivery systems utilize osmotic pressure to generate a driving force for imbibing fluid into a compartment enclosed partially or completely by a semipermeable membrane that permits free diffusion of a fluid but not solutes, including active or osmotic agents.

Osmotic-controlled compositions comprising a drug in a mixture with osmotically active agents/osmotic agents are known in the art (e.g., U.S. Pat. Nos. 4,327,725; 4,612,008; 4,783,337; 5,082,668). These compositions comprise a bilayer tablet core surrounded by a semipermeable membrane with an orifice. The first component layer, the pull layer, comprises a drug(s) in a mixture of excipients that forms a deliverable drug formulation within the compartment. A second component layer, the push layer, comprises osmotic agents, e.g., swellable hydrophilic polymers and osmogens. The swellable hydrophilic polymers in the second component layer comprise one or more high molecular weight hydrophilic polymers that swell as fluid is imbibed. The second component layer is referred to as "push layer" because as fluid is imbibed, the hydrophilic polymer swells and pushes against the deliverable drug formulation in the first component layer, thereby facilitating release of drug formulation from the first layer through an orifice in the semipermeable membrane at a substantially constant rate.

Although suitable for providing a controlled release of drugs with various solubilities, osmotic-controlled compositions known in the art are not entirely suitable for being programmed as controlled release compositions that 1) delay the release of a drug/provide a lag time for at least about 3 hours, 2) provide a lag time that is independent of the presence or absence of food, type of food, pH, gastric emptying, and volume of gastric fluid, 3) provide a plasma concentration of the active pharmaceutical ingredient during the lag time that is less than about 20% of a maximum concentration ($C_{max}$), 4) provide pH-independent drug release, after the lag time, at a rhythm that matches the human circadian rhythm of a condition's symptoms and/or of the individual being treated in the application of the therapy, and 5) provide a desired bioavailability and complete drug recovery at a desired time. A typical osmotic-controlled system known in the art provides a short lag time of about 30-120 minutes during which the system hydrates before zero-order delivery from the system is obtained.

For at least these reasons, there remains a need to develop osmotic-controlled systems that can provide controlled release of a drug at a desired rate and time, while providing complete drug recovery. There remains a need to develop compositions that can be programmed for treating conditions that require delayed controlled release of a drug, e.g., compositions for treating central nervous system (CNS) disorders, asthma, arthritis, congestive heart failure, myocardial infarction, stroke, cancer, peptic ulcer, narcolepsy, epilepsy, migraine, pain, etc., wherein the risk and symptoms of the disease vary predictably over time.

The present disclosure addresses the above-mentioned unmet needs in the art by providing osmotic-controlled, oral delayed release compositions that can improve the symptoms of a disease in the early morning and throughout the day, or in a pulsatile manner, without the need for early morning dosing that requires an onset time of about two hours. Such compositions address the long-felt need of providing food-independent delayed release that can avoid burdensome early morning dosing and can be programmed to provide a desired and precise lag time, thereby releasing drug, after the lag time, at a rhythm, e.g., that matches the human circadian rhythm of a condition's symptoms and/or of the individual being treated in the application of the therapy, to optimize therapeutic outcome and minimize side effects. The compositions of the disclosure provide a precise lag time that is independent of the presence or absence of food, type of food, pH, gastric emptying, gastric transit time, and volume of fluid in the immediate microenvironment of drug release. In particular, the osmotic-controlled, oral, delayed release compositions of the disclosure provide desired drug bioavailability while releasing the drug in lower portions of the GI tract, e.g., colon, with viscous alkaline microenvironment. The osmotic-controlled oral compositions of the disclosure are designed to provide minimal variability in drug release among tablets.

4. SUMMARY

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

To achieve these advantages and in accordance with the purpose of the disclosed subject matter, as embodied and broadly described subject matter includes an osmotic-controlled oral pharmaceutical composition providing delayed release of a therapeutically effective amount a drug, the composition including a multilayer core including an active layer sandwiched between a placebo layer and a push layer, wherein the placebo layer includes at least one polyethylene oxide polymer having an average molecular weight of from about 300,000 Da to about 900,000 Da; the active layer includes a drug, at least one polyethylene oxide polymer having a molecular weight of from about 100,000 Da to about 600,000 Da; the push layer includes at least one polyethylene oxide polymer having an average molecular weight of greater than or equal to 1000,000 Da, and at least one osmogen; and a semipermeable membrane surrounding the multilayer core, wherein the semipermeable membrane is present in an amount of from about 1 wt % to about 20 wt % coating weight gain, based on the total weight of the multilayer core. In certain embodiments, the semipermeable membrane includes at least one orifice facing the placebo layer. In certain embodiments, the orifice has an optimum orifice diameter of from about 0.6 mm to about 2.0 mm. In certain embodiments, the placebo layer is present in an amount of from about 10 wt % to about 50 wt %, based on the total weight of the multilayer core. In certain embodiments, the active layer contains a drug: polyethylene oxide polymer ratio of between about 20:80 and about 80:20 by weight. In certain embodiments, the osmogen in the push layer is present in an amount of from about 5 w % to about 30 wt %, based on total weight of the push layer.

In certain embodiments, the composition provides a lag time of at least about 3 hours, during which the composition releases no more than 20 wt % of the drug.

In certain embodiments, the composition exhibits not more than 30% variability in the lag time with variations in pH, viscosity, and volume of a dissolution medium.

In certain embodiments, the lag time does not depend upon gastric motility and presence of food in the GI tract.

In certain embodiments, the semipermeable membrane includes a pH-independent water-insoluble polymer and a pH-independent pore former at a polymer to pore former ratio of between about 80:20 and about 99.5:0.5 by weight.

In certain embodiments, the semipermeable membrane includes a pH-independent water-insoluble polymer and a pH-independent pore former at a polymer to pore former ratio of between about 90:10 and about 95:5 by weight.

In certain embodiments, the pH-independent water-insoluble polymer is selected from the group consisting of cellulose acetate, cellulose acetate butyrate, and cellulose triacetate.

In certain embodiments, the pH-independent pore former is selected from the group consisting of polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

In certain embodiments, the semipermeable membrane further includes at least one plasticizer selected from the group consisting of polyethylene glycols, triethyl citrate, triacetin, diethyl tartrate, dibutyl sebacate, and combinations thereof.

In certain embodiments, the polyethylene oxide polymer in the push layer has an average molecular weight of about 1000,000 Da, about 2000,000 Da, about 4000,000 Da, about 5000,000 Da, about 7000,000 Da, or intermediate values therein.

In certain embodiments, the placebo layer further comprises a wicking agent selected from the group consisting of croscarmellose sodium, calcium carboxymethyl cellulose, crospovidone, low-substituted hydroxypropyl celluloses, sodium starch glycolate, colloidal silicon dioxide, alginic acid and alginates, acrylic acid derivatives, and various starches.

In certain embodiments, the placebo layer further comprises an osmogen selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, and combinations thereof.

In certain embodiments, the placebo layer further comprises a wicking agent and an osmogen.

In certain embodiments, the composition further comprises an immediate release drug layer over the semipermeable membrane, wherein the immediate release drug layer contains a drug that is similar to the drug in the active layer.

In certain embodiments, the composition further comprises an immediate release drug layer over the semipermeable membrane, wherein the immediate release drug layer contains a drug that is different from the drug contained in the active layer.

In certain embodiments, the present disclosure provides an osmotic-controlled oral pharmaceutical composition providing an immediate release of a therapeutically effective amount of a drug and a delayed release of a therapeutically effective amount of the same or a different drug, the composition including a multilayer core including an active layer sandwiched between a placebo layer and a push layer, wherein the placebo layer includes at least one polyethylene oxide polymer having an average molecular weight of from about 300,000 Da to about 900,000 Da; the active layer includes a drug, at least one polyethylene oxide polymer having a molecular weight of from about 100,000 Da to about 600,000 Da; the push layer includes at least one polyethylene oxide polymer having an average molecular weight of greater than or equal to 1000,000 Da, and at least one osmogen; a semipermeable membrane surrounding the multilayer core; and an immediate release drug layer surrounding the semipermeable membrane. The immediate release drug layer comprises at least one drug for immediate release. In certain embodiments, the semipermeable membrane is present in an amount of from about 1 wt % to about 20 wt % coating weight gain, based on the total weight of the multilayer core. In certain embodiments, the semipermeable membrane includes at least one orifice facing the placebo layer. In certain embodiments, the orifice has an optimum orifice diameter of from about 0.6 mm to about 2.0 mm. In certain embodiments, the placebo layer is present in an amount of from about 10 wt % to about 50 wt %, based on the total weight of the multilayer core. In certain embodiments, the active layer contains the drug and polyethylene oxide polymer in a ratio of between about 20:80 and about 80:20 by weight. In certain embodiments, the osmogen in the push layer is present in an amount of from about 5 w % to about 30 wt %, based on total weight of the push layer.

In certain embodiments, the drug for immediate release is a sedative selected from the group consisting of clonidine, guanfacine, diphenhydramine, melatonin, and pharmaceutically acceptable salts thereof.

In certain embodiments, the drug for delayed release is selected from the group consisting of methylphenidate, mixed amphetamines, armodafinil, hydrocortisone, and pharmaceutically acceptable salts thereof.

In certain embodiments, the drug for immediate release is a sedative and the drug for delayed release is a stimulant. In certain embodiments, the delayed release is a delayed extended release and the composition provides immediate release of the sedative, a lag time of at least about 6 hours during which the composition releases no more than 10% of stimulant, and a delayed extended release of the stimulant.

In certain embodiments, the disclosure provides an osmotic-controlled oral pharmaceutical composition providing pulsatile release of a therapeutically effective amount of one or more drugs, the composition including a multilayer core and a semipermeable membrane over the multilayer core. The multilayer core includes layers in the following order: a first placebo layer containing at least one polyethylene oxide polymer having an average molecular weight of from about 300,000 Da to about 900,000 Da; a first active layer containing a first drug and at least one polyethylene oxide polymer having an average molecular weight from about 300,000 Da to about 900,000 Da; a second placebo layer containing at least one polyethylene oxide polymer having an average molecular weight of from about 300,000 Da to about 900,000 Da; a second active layer containing a second drug and at least one polyethylene oxide polymer having an average molecular weight from about 300,000 Da to about 900,000 Da; and a push layer containing at least one polyethylene oxide polymer having an average molecular weight of greater than or equal to 1000,000 Da, and at least one osmogen. In certain embodiments, the semipermeable membrane is present in an amount of from about 1 wt % to about 20 wt % coating weight gain, based on the total weight of the multilayer core. In certain embodiments, the semipermeable membrane includes at least one orifice facing the placebo layer. In certain embodiments, the orifice has an optimum orifice diameter of from about 0.6 mm to about 2.0 mm. In certain embodiments, each of the first and the second placebo layer is present in an amount of from about 10 wt % to about 50 wt %, based on the total weight of the multilayer core. In certain embodiments, each of the first active layer and the second active layer contains a drug: polyethylene oxide polymer ratio of between about 20:80 and about 80:20 by weight. In certain embodiments, the osmogen in the push layer is present in an amount of from about 5 w % to about 30 wt %, based on total weight of the push layer. In certain embodiments, the pulsatile release comprises a delayed release of a first pulse containing the first drug, a lag time, and a second pulse containing the second drug.

In certain embodiment, the first drug and the second drug are same. In certain embodiments, the composition further comprises an immediate release drug layer over the semipermeable membrane, wherein the immediate release drug layer contains a third drug. In certain embodiments, the third drug is different from the first drug and the second drug.

In certain embodiments, the disclosure provides an osmotic-controlled oral pharmaceutical composition providing pulsatile release of a therapeutically effective amount of one or more drugs, the composition including a multilayer core and a semipermeable membrane over the multilayer core. The multilayer core includes layers in the following order: a first active layer containing a first drug and at least one polyethylene oxide polymer having an average molecular weight from about 300,000 Da to about 900,000 Da; a first placebo layer containing at least one polyethylene oxide polymer having an average molecular weight of from about 300,000 Da to about 900,000 Da; a second active layer containing a second drug and at least one polyethylene oxide polymer having an average molecular weight from about 300,000 Da to about 900,000 Da; a second placebo layer containing at least one polyethylene oxide polymer having an average molecular weight of from about 300,000 Da to about 900,000 Da; and a push layer containing at least one polyethylene oxide polymer having an average molecular weight of greater than or equal to 1000,000 Da, and at least one osmogen. In certain embodiments, the semipermeable membrane is present in an amount of from about 1 wt % to about 20 wt % coating weight gain, based on the total weight of the multilayer core. In certain embodiments, the semipermeable membrane includes at least one orifice facing the active layer. In certain embodiments, the orifice has an optimum orifice diameter of from about 0.6 mm to about 2.0 mm. In certain embodiments, each of the first and the second placebo layer is present in an amount of from about 10 wt % to about 50 wt %, based on the total weight of the multilayer core. In certain embodiments, each of the first active layer and the second active layer contains a drug: polyethylene oxide polymer ratio of between about 20:80 and about 80:20 by weight. In certain embodiments, the osmogen in the push layer is present in an amount of from about 5 w % to about 30 wt %, based on total weight of the push layer. In certain embodiments, the pulsatile release comprises release of a first pulse containing the first drug, a lag time, and a second pulse containing the second drug.

5. BRIEF DESCRIPTION OF THE DRAWINGS

FIG. 1 depicts a cross-section view of a four-layer osmotic dosage form comprising an IR clonidine coating; a cellulose acetate coating containing an orifice, placed below the clonidine IR coating; a placebo layer facing the orifice; a delayed immediate release layer, containing methylphenidate or a pharmaceutically acceptable salt thereof, placed below the placebo layer; a delayed extended release layer, containing methylphenidate or a pharmaceutically acceptable salt thereof, placed below the delayed immediate release layer; and a push layer placed below the delayed extended release layer.

Figure 2:
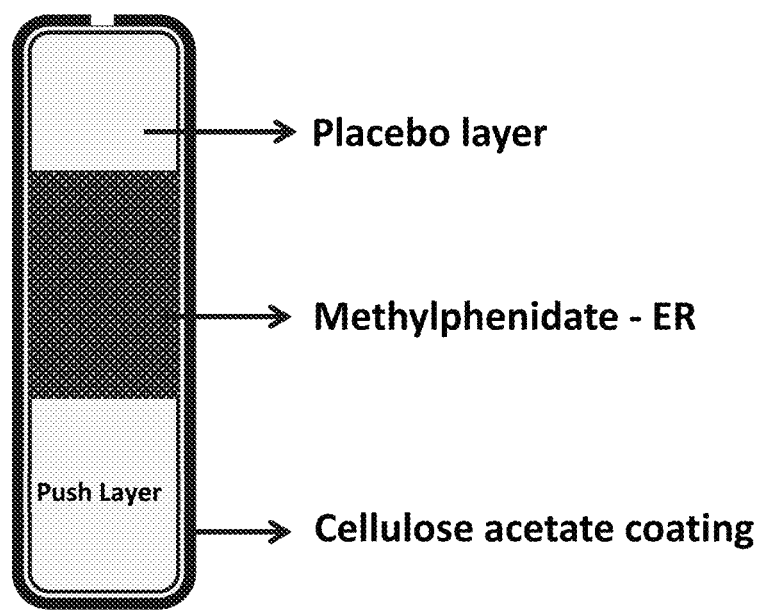

FIG. 2 depicts a cross-section view of a three-layer osmotic dosage form comprising a cellulose acetate coating containing an orifice; a placebo layer facing the orifice; a delayed extended release layer, containing methylphenidate or a pharmaceutically acceptable salt thereof, placed below the placebo layer; and a push layer placed below the delayed extended release layer.

Figure 3:
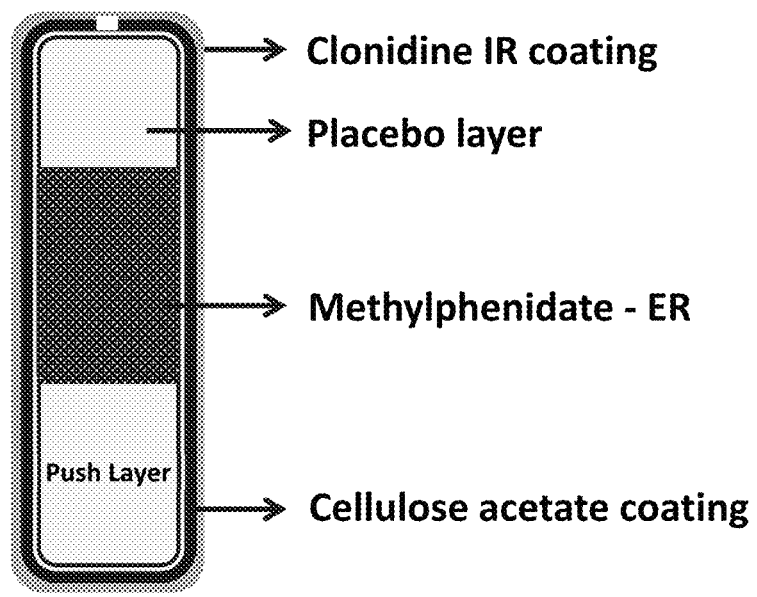

FIG. 3 depicts a cross-section view of a three-layer osmotic dosage form comprising an IR clonidine coating; a cellulose acetate coating containing an orifice, placed below the clonidine IR coating; a placebo layer facing the orifice; a delayed extended release layer containing methylphenidate or a pharmaceutically acceptable salt thereof, placed below the placebo layer; and a push layer placed below the delayed extended release layer.

Figure 4:
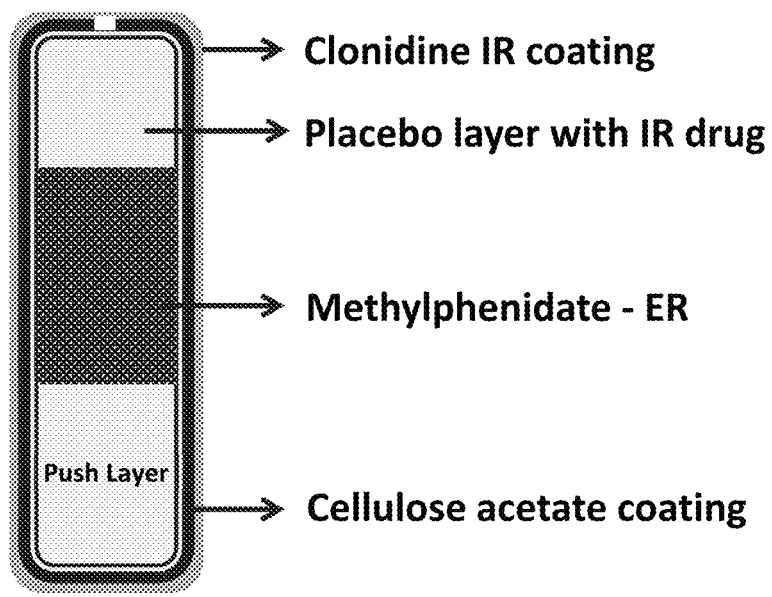

FIG. 4 depicts a cross-section view of a three-layer osmotic dosage form comprising an IR clonidine coating; a cellulose acetate coating containing an orifice, placed below the clonidine IR coating; a placebo layer containing small amounts of a drug for immediate release and facing the orifice; a delayed extended release layer, containing methylphenidate or a pharmaceutically acceptable salt thereof, placed below the placebo layer; and a push layer placed below the delayed extended release layer.

Figure 5:
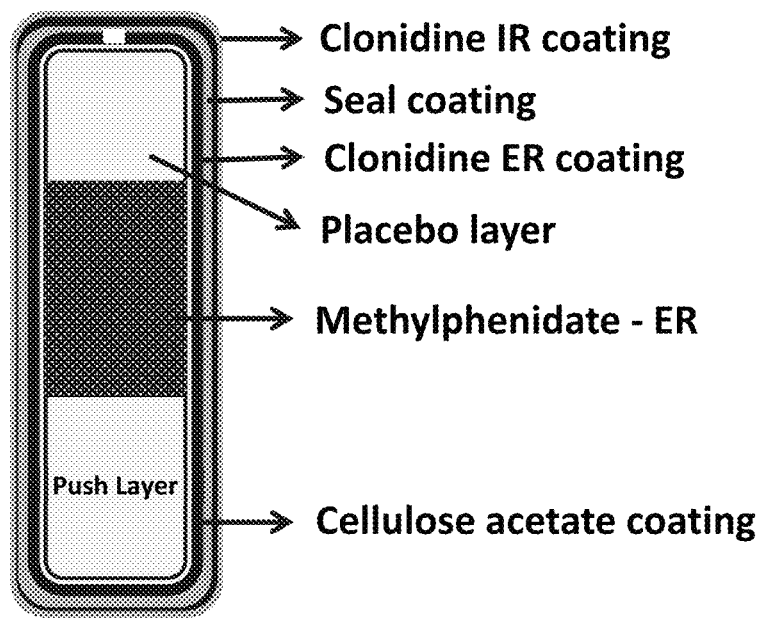

FIG. 5 depicts a cross-section view of a three-layer osmotic dosage form comprising an IR clonidine coating; a seal coating below the IR clonidine coating; a clonidine ER coating below the seal coating; a cellulose acetate coating containing an orifice, placed below the ER clonidine coating; a placebo layer facing the orifice; a delayed extended release layer containing methylphenidate or a pharmaceutically acceptable salt thereof, placed below the placebo layer; and a push layer placed below the delayed extended release layer.

Figure 6:
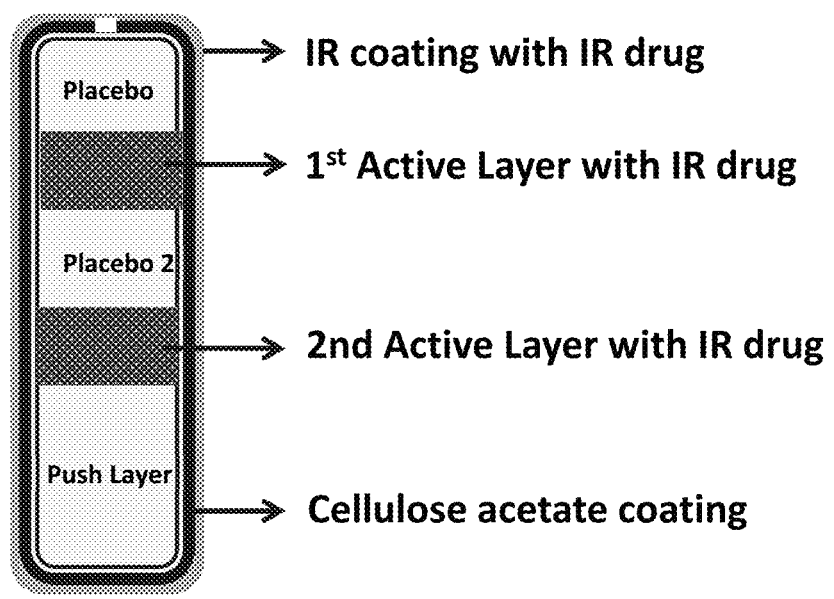

FIG. 6 depicts a cross-section view of a five-layer osmotic dosage form comprising an IR coating containing a drug for IR, a cellulose acetate coating containing an orifice below the IR coating, a first placebo layer facing the orifice, a first IR drug layer below the first placebo layer, a second placebo layer below the first IR drug layer, a second IR drug layer below the second placebo layer, and a push layer placed below the second IR drug layer and facing away from the orifice.

Figure 7:
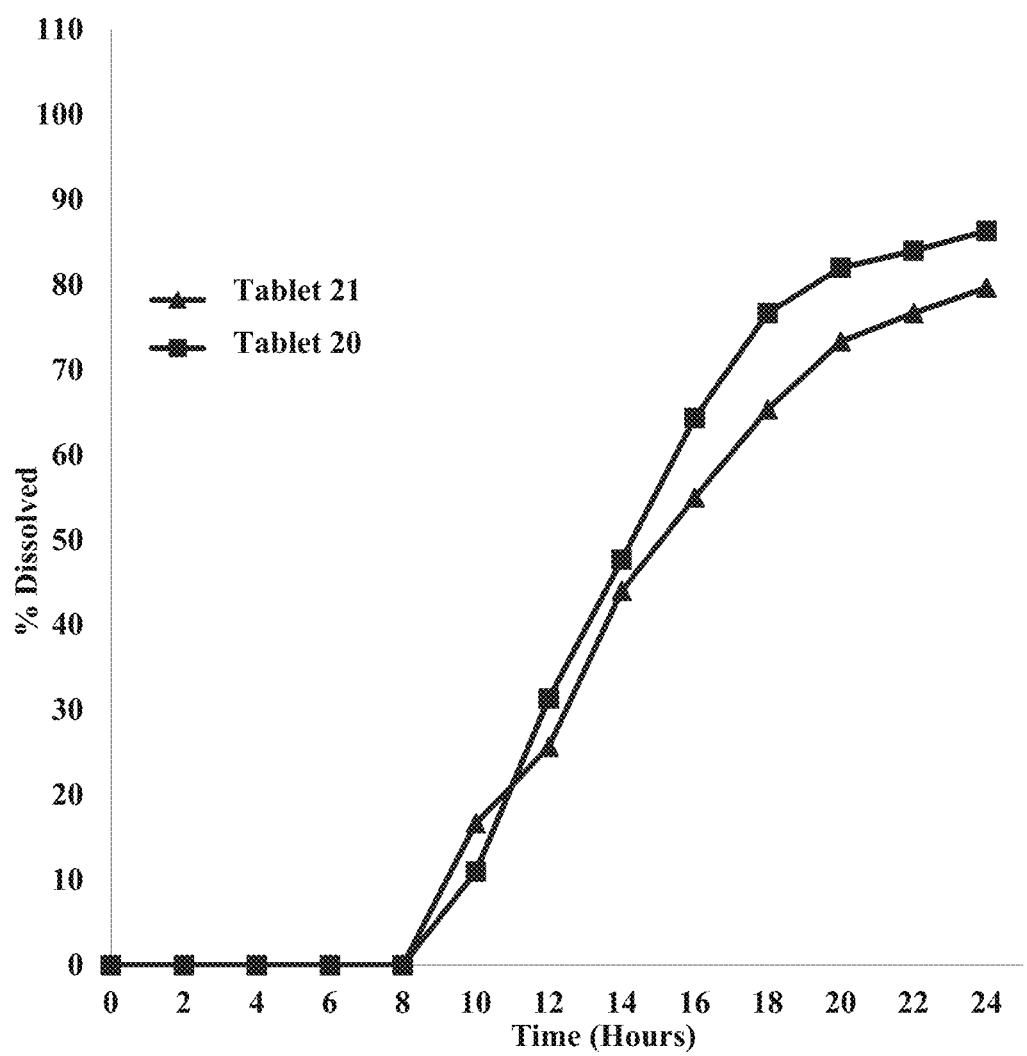

FIG. 7 shows the effect of the amount of placebo layer amount on dissolution profile of Tablets 20 and 21, placed in about 900 ml of about 0.01N HCl, using USP II (sinkers) at about 50 rpm and about 37° C. Percent drug dissolved is plotted over time (hours). Tablet 20 contains 150 mg of POLYOX® WSR 1105 in the placebo layer; and Tablet 21 contains 75.0 mg of POLYOX® WSR 1105 in the placebo layer. Tablet 20 contains about 34 wt % of placebo layer, based on the total weight of the uncoated tablet core. Tablet 21 contains about 20 wt % of placebo layer, based on the total weight of the uncoated tablet core. Tablets 20 and 21 contain 15 wt % of coating, based on the total weight of the uncoated tablet core. The figure demonstrates that tablets with higher amount of placebo layer exhibit higher dissolution rate and higher drug recovery compared to tablets with lesser amounts of placebo layer. The figure further demonstrates that the POLYOX® WSR 1105 amount in the placebo layer, and weight % of placebo layer, based on the total weight of the uncoated tablet core, does not affect lag time.

Figure 8:
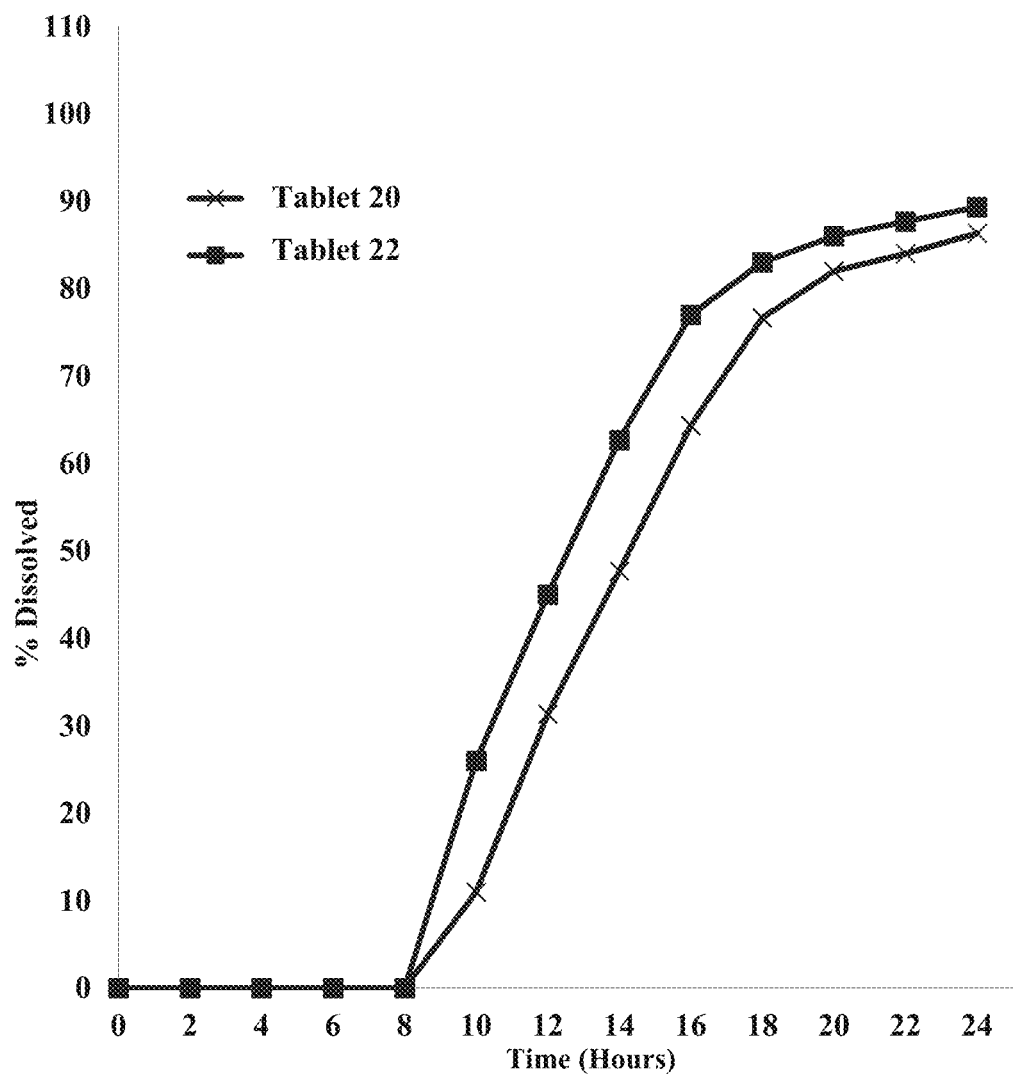

FIG. 8 shows the effect of average molecular weight of the POLYOX®, present in the placebo layer, on dissolution profile of the tablets 20 and 22, placed in about 900 ml of about 0.01N HCl for up to 24 hours, using USP Apparatus II (Sinkers), at 50 rpm and 37° C. Percent drug dissolved is plotted over time (hours) . . . Tablet 20 contains POLYOX® WSR 1105, and Tablet 22 contains POLYOX® 205 in the placebo layer. The Figure demonstrates an improvement in dissolution rate and reduction in drug recovery, and no change in lag time, with increasing the average molecular weight of POLYOX®, present in the placebo layer, from about 600K (POLYOX® 205) to about 900K (POLYOX® 1105).

Figure 9:
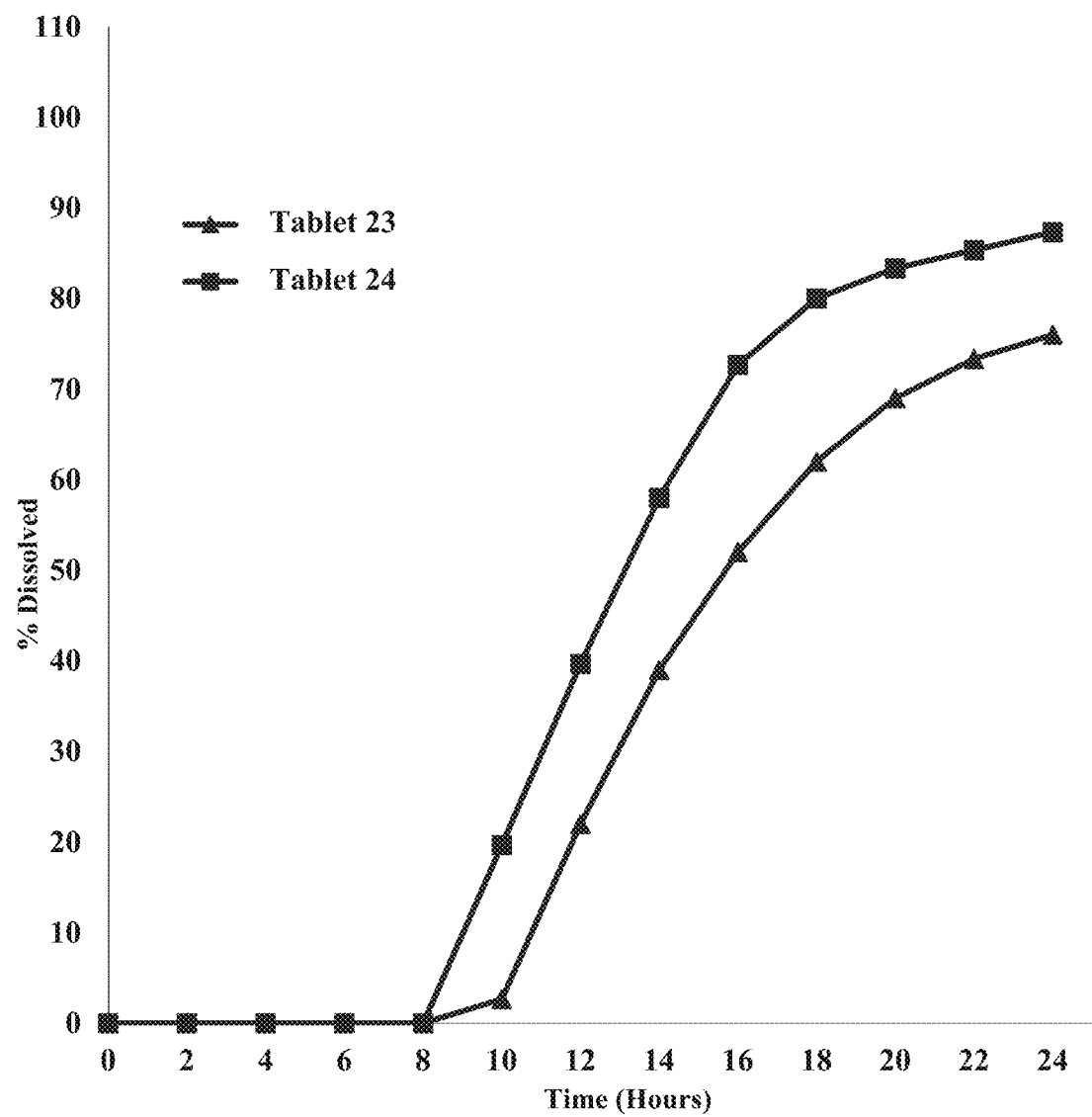

FIG. 9 shows the effect of drug:polymer weight ratio on lag time and drug recovery of Tablets 23 and 24, placed in about 900 ml of about 0.01N HCl for up to 24 hours, using USP Apparatus II (Sinkers), at 50 rpm and 37° C. Percent drug dissolved is plotted over time (hours). Tablet 24 containing a drug to polymer weight ratio of about 30:70 provides a lag time of about 9 hours, Tablet 23 containing a drug to polymer weight ratio of about 20:80 provides a lag time of about 10 hours. The figure demonstrates that increasing drug:polymer weight ratio in the active layer reduces lag time. The figure further demonstrates that tablets with the drug to polymer weight ratio of about 30:70 provide higher drug recovery compared to tablets with drug to polymer weight ratio of about 20:80.

Figure 10:
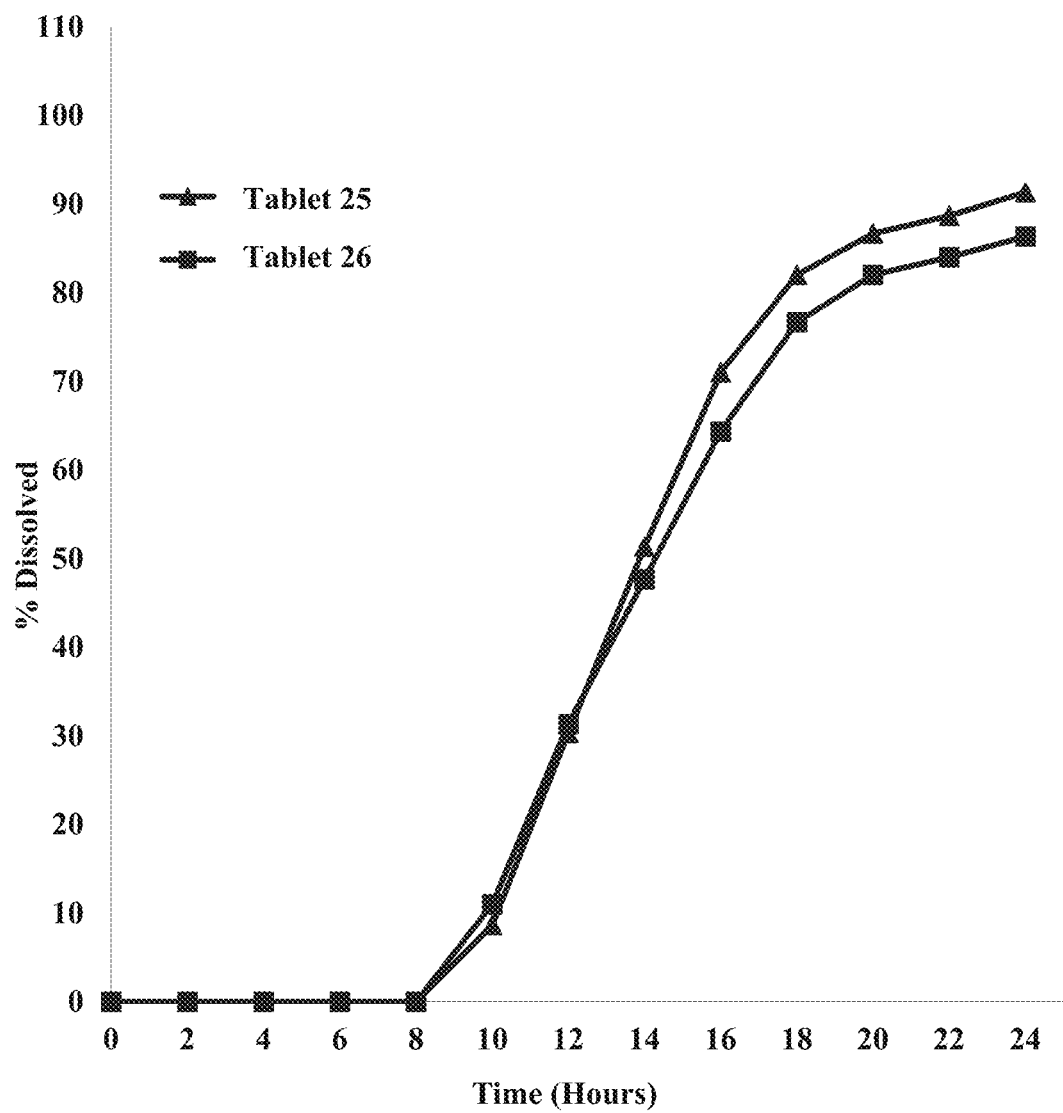

FIG. 10 shows the effect of presence of sodium chloride in the active layer on dissolution profile of Tablets 25 and 26, placed in about 900 ml of about 0.01N HCl using USP Apparatus II (Sinkers), at 50 rpm and 37° C. Percent drug dissolved is plotted over time (hours). Tablet 25 contains sodium chloride in the active layer and Tablet 26 does not contain sodium chloride in the active layer. The figure demonstrates that Tablet 25 containing NaCl in the active layer exhibits higher drug recovery compared to Tablet 26 containing no amount of sodium chloride in the active layer.

Figure 11:
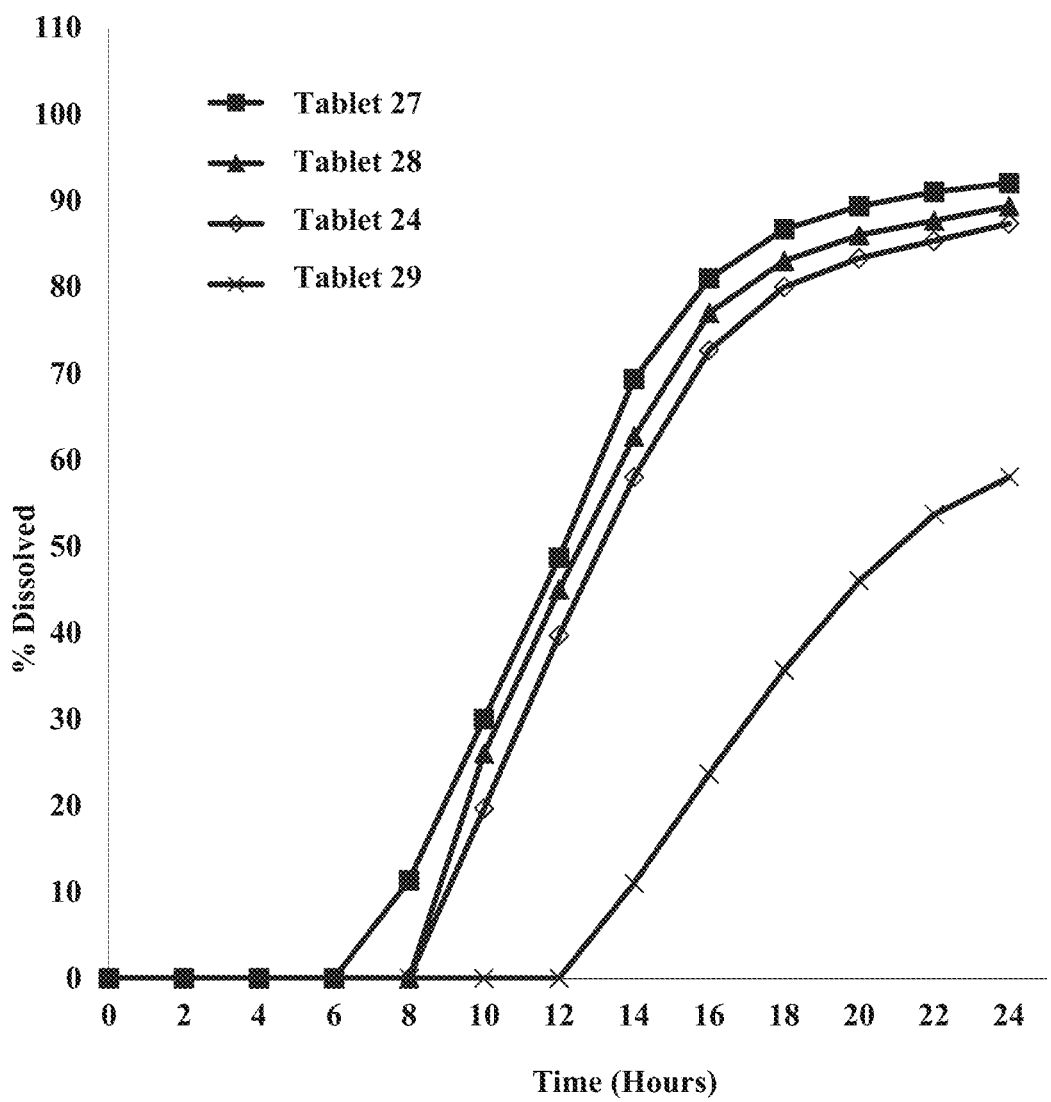

FIG. 11 shows the effect of presence of sodium chloride in the push layer on dissolution profile of Tablets 24, 27, 28, and 29, placed in about 900 ml of about 0.01N HCl for up to 24 hours, using USP Apparatus II (Sinkers), at 50 rpm and 37° C. Percent drug dissolved is plotted over time (hours). The figure demonstrates that the presence of sodium chloride in the push layer reduces lag time and improves release rate and drug recovery at 24 hours. The figure further demonstrates that increasing the amount of sodium chloride in the push layer reduces lag time.

Figure 12:
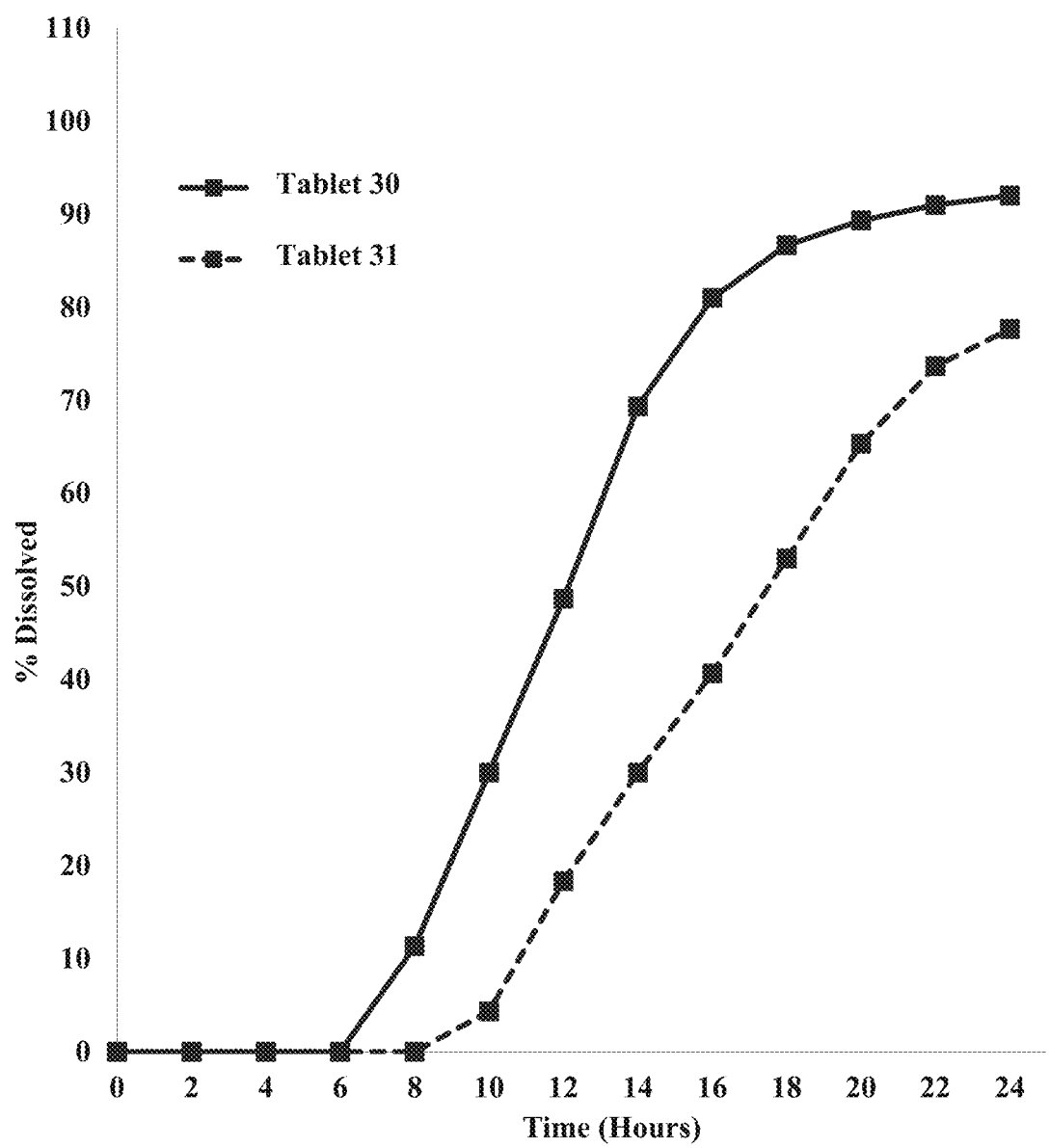

FIG. 12 shows the effect of CA to PEG ratio in the membrane on lag time and drug recovery of the Tablets 30 and 31, with 15% coating weight gain, placed in about 900 ml of about 0.01N HCl for up to 24 hours, using USP Apparatus II (Sinkers), at 50 rpm and 37° C. Percent drug dissolved is plotted over time (hours). The Figure demonstrates that increasing amount of cellulose acetate in the membrane increases lag time and reduces drug recovery from the membrane coated tablets.

Figure 13:
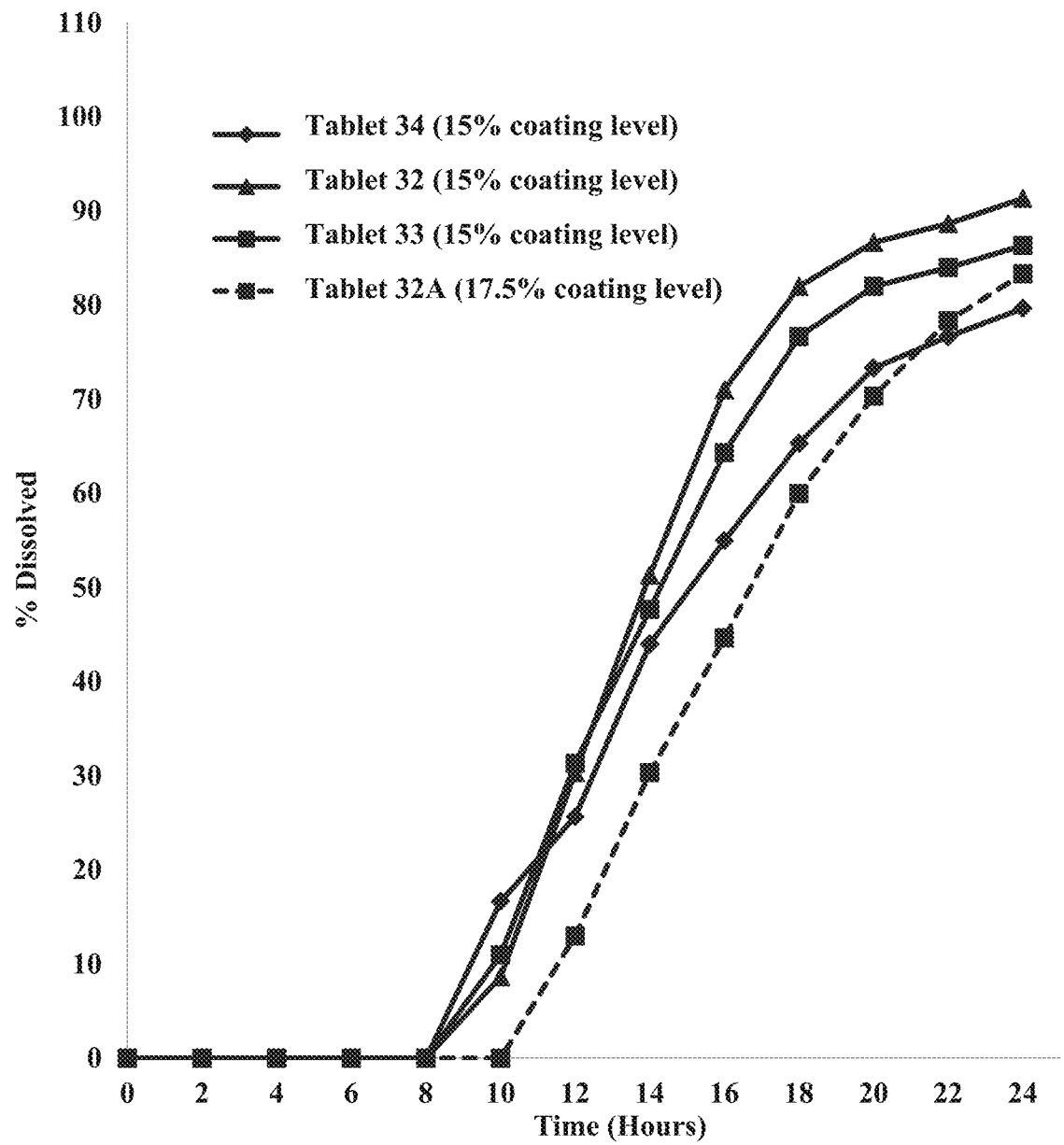

FIG. 13 shows the effect of coating weight gain, and presence of sodium chloride in the active layer, on lag time and drug recovery of Tablets 32, 32A, 33, and 34, placed in about 900 ml of about 0.01N HCl for up to 24 hours, using USP Apparatus II (Sinkers), at 50 rpm and 37° C. Percent drug dissolved is plotted over time (hours). The Figure demonstrates that the tablet with a higher coating level (Tablet 32A) exhibits reduced drug recovery and increased lag time compared to Tablet 32. The Figure further compares drug recovery between coated tablets at same coating weight gain, with and without sodium chloride in active layer. The Figure demonstrates that tablets containing sodium chloride in active layer exhibit improved drug recovery compared to tablets without sodium chloride in the active layer, both tablets at a same coating weight gain. The Figure further shows that a decrease in amount of POLYOX® 205 in placebo layer improves drug recovery.

Figure 14:
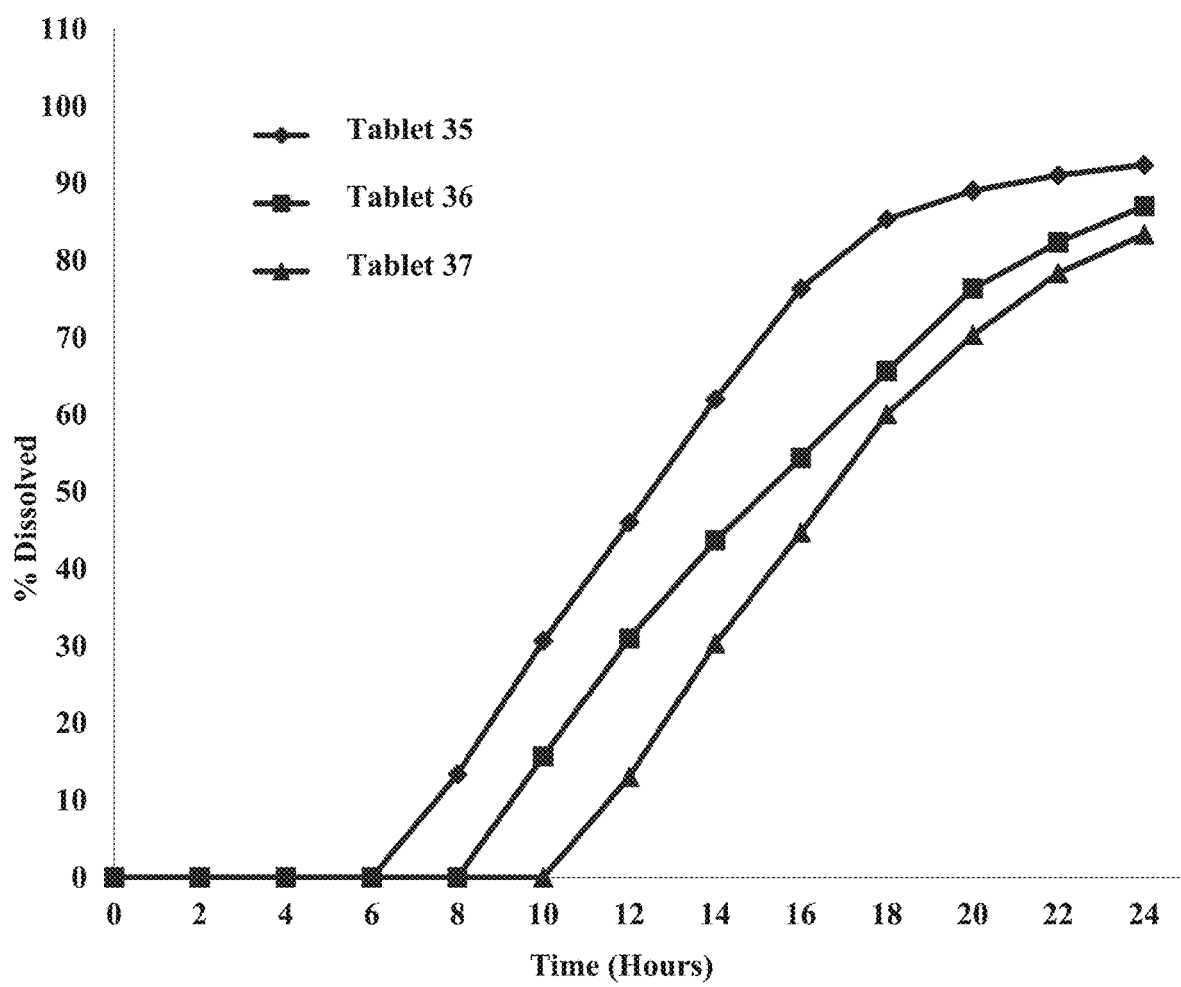

FIG. 14 shows the effect of average molecular weight of the POLYOX® present in the placebo layer on lag time and drug recovery of Tablets 35, 36, and 37, placed in about 900 ml of about 0.01N HCl for up to 24 hours, using USP Apparatus II (Sinkers), at 50 rpm and 37° C. Percent drug dissolved is plotted over time (hours). The figure demonstrates that Tablet 35 containing POLYOX® 205 in the placebo layer and 20 mg of sodium chloride in the active layer provide shorter lag time compared to Tablet 36 containing POLYOX® 1105 in the placebo layer and 10 mg od NaCl in the active layer.

The figure further demonstrates that for Tablets containing POLYOX® 205 in the placebo layer, the tablets with higher sodium chloride amount in active layer and less coating weight gain (Tablet 35) provide shorter lag time compared to tablets containing higher coating level and less amount of sodium chloride in the active layer (Tablet 36).

Figure 15:
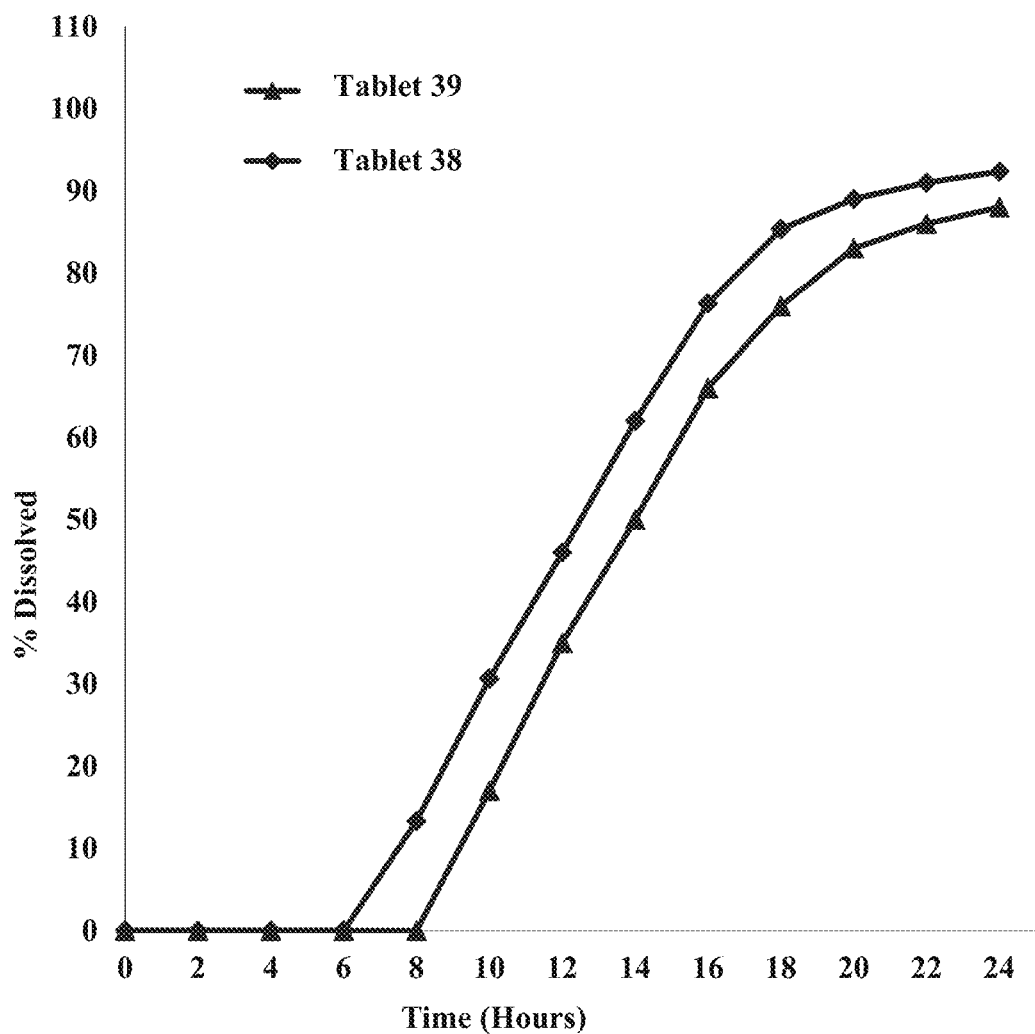

FIG. 15 shows the effect of push layer amount on lag time of Tablets 38 and 39, placed in about 900 ml of about 0.01N HCl for up to 24 hours, using USP Apparatus II (Sinkers), at 50 rpm and 37° C. Percent drug dissolved is plotted over time (hours). The Figure demonstrates that for tablets containing POLYOX® 205 in the placebo layer, the lag time decreases with increase in push layer amount from about 17 wt % to about 22 wt %, based on the total weight of the uncoated trilayer tablet.

Figure 16:
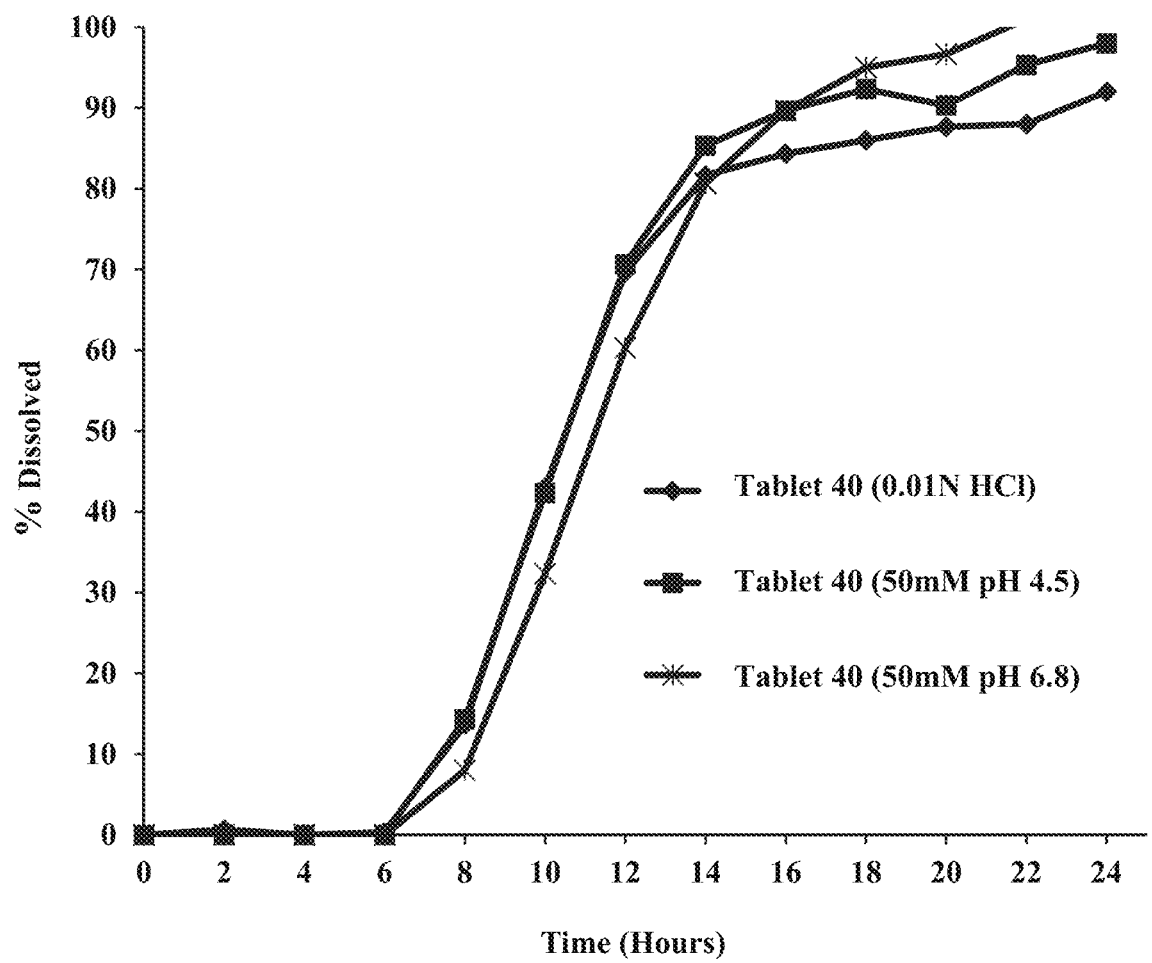

FIG. 16 shows the effect of pH on lag time of Tablet 40, placed in about 900 ml of about 0.01N HCl, in pH 4.5 acetate buffer, and in pH 6.8 phosphate buffer. Percent drug dissolved is plotted over time (hours). The Figure demonstrates that lag time is independent of the pH of the dissolution medium.

Figure 17:
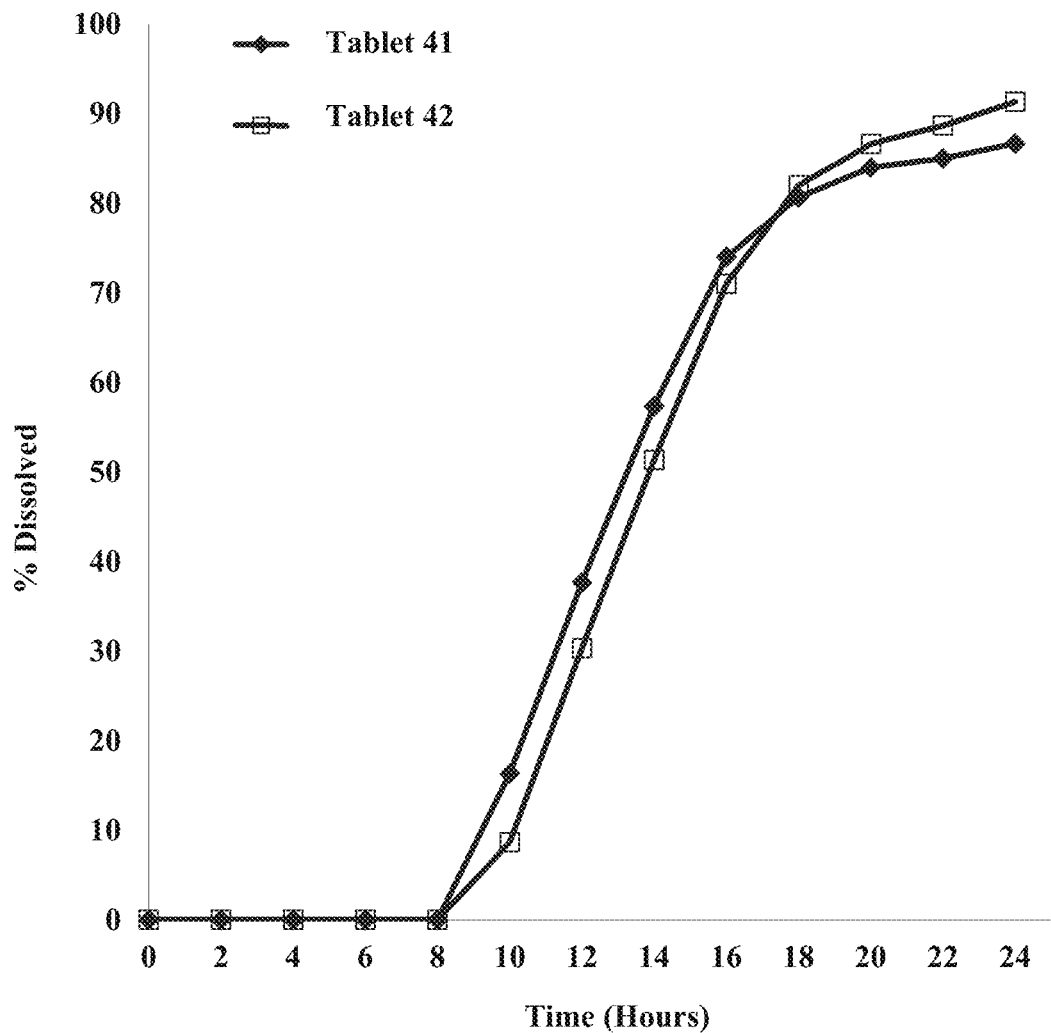

FIG. 17 shows the effect of the push layer amount on lag time in Tablets 41 and 42, placed in about 900 ml of about 0.01N HCl for up to 24 hours, using USP Apparatus II (Sinkers), at 50 rpm and 37° C. Percentage drug dissolved is plotted over time (hours). The figure demonstrates that for tablets containing POLYOX® 1105 in the placebo layer and with a drug:polymer weight ratio of about 40:60 in the active layer, an increase in push layer amount, from about 26 wt % to about 28 wt %, based on the total weight of the uncoated tablet core, improves drug recovery without affecting the lag time.

Figure 18:
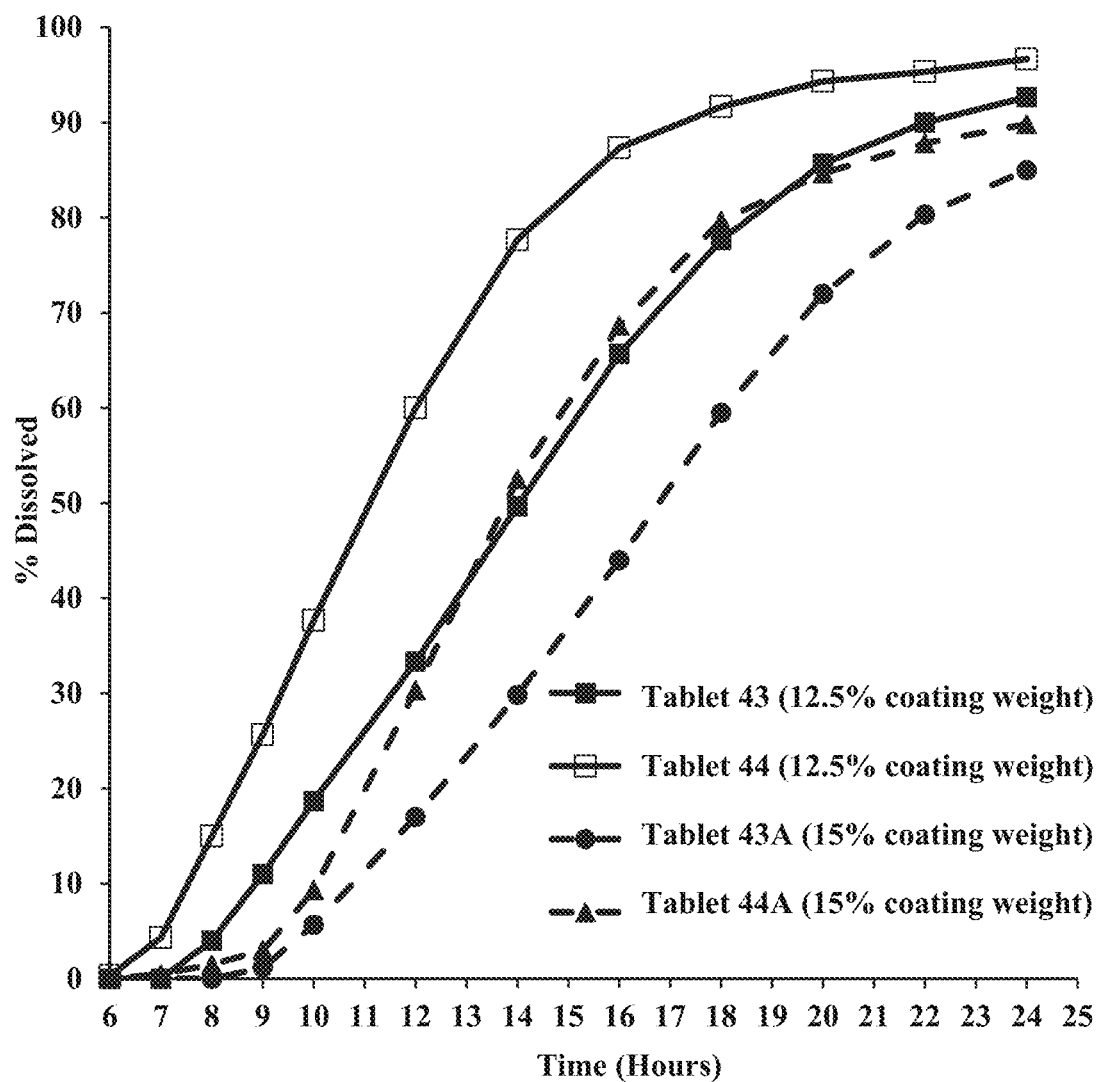

FIG. 18 shows effect of polymer amount in the placebo layer and coating weight gain/coating level on lag time of Tablets 43 and 44, containing a drug:polymer weight ratio of about 40:60, placed in about 900 ml of about 0.01N HCl for up to 24 hours, using USP Apparatus II (Sinkers), at 50 rpm and 37° C. Percentage drug dissolved is plotted over time (hours). The Figure demonstrates that higher placebo layer amounts and higher coating level on tablet increases lag time.

Figure 19:
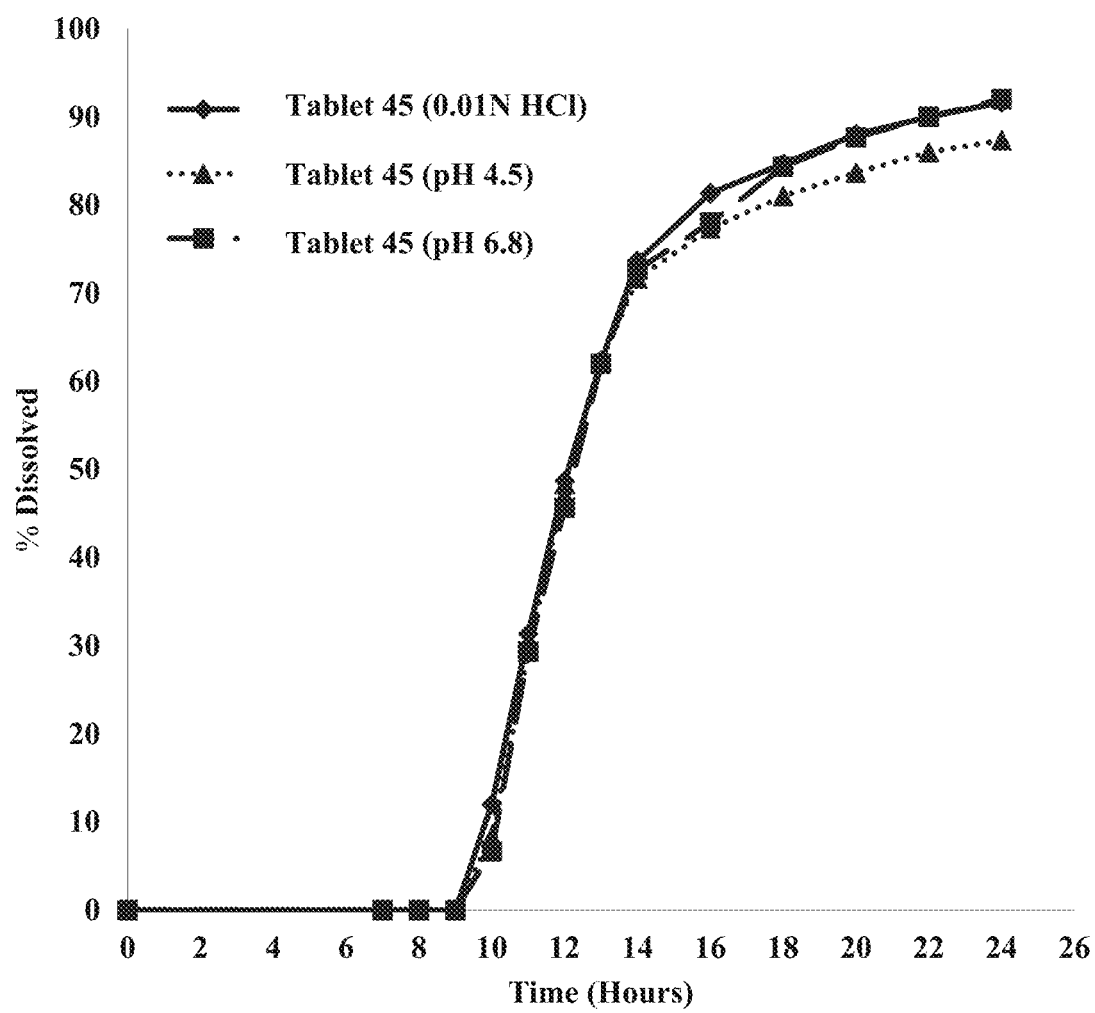

FIG. 19 shows the effect of pH on lag time of Tablet 40, placed in about 900 ml of about 0.01N HCl, pH 4.5 acetate buffer, and in pH 6.8 phosphate buffer. Percent drug dissolved is plotted over time (hours). The figure demonstrates that there is no substantial change in lag time with changing pH of the dissolution medium.

Figure 20:
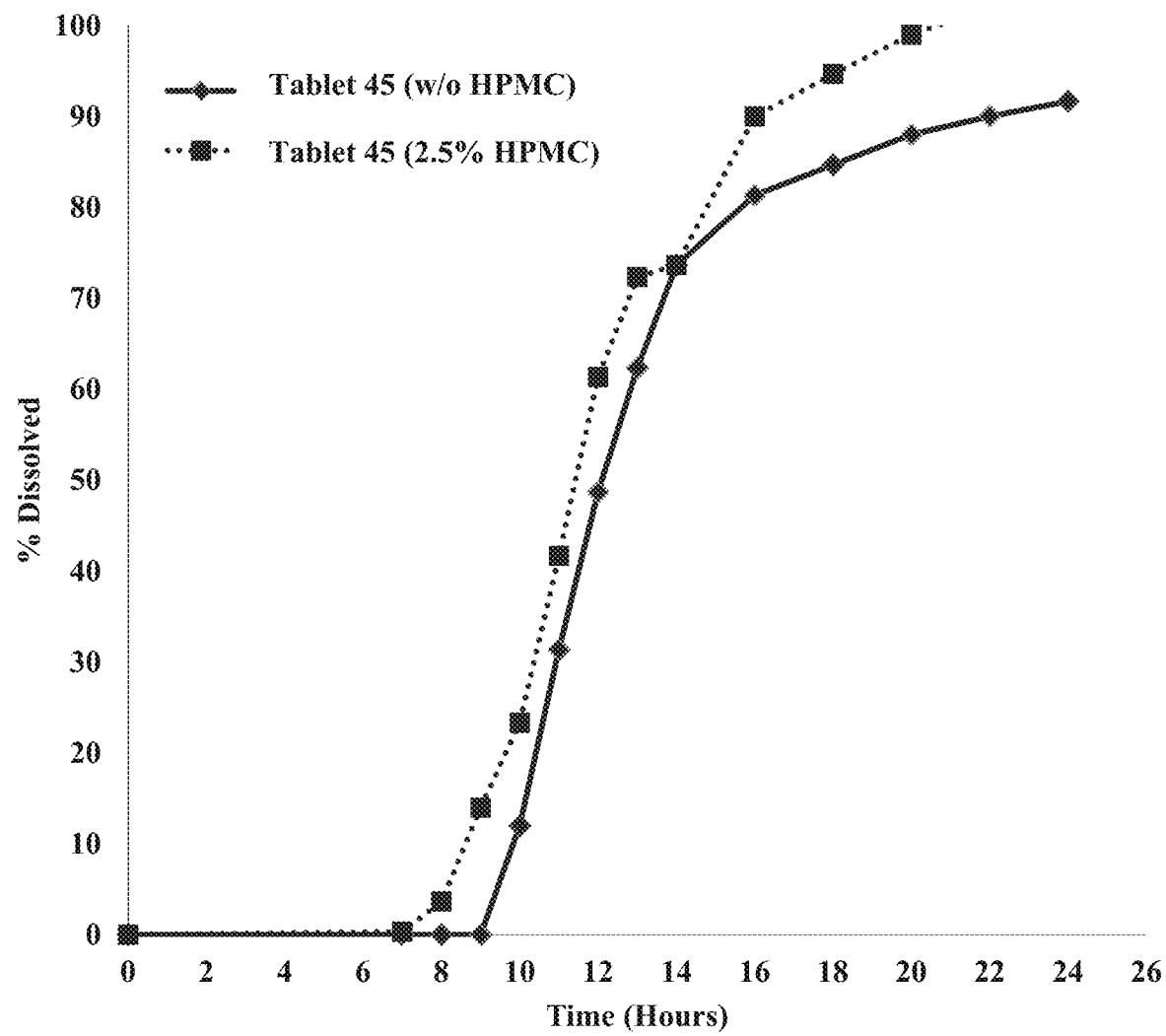

FIG. 20 shows the effect of viscosity of the dissolution medium on lag time of Tablet 45, placed in dissolution mediums with different viscosities, e.g., with and without HPMC. Percent dissolved is plotted over time (hours). The Figure demonstrates there is no substantial change in lag time with changing viscosity of the dissolution medium.

Figure 21:
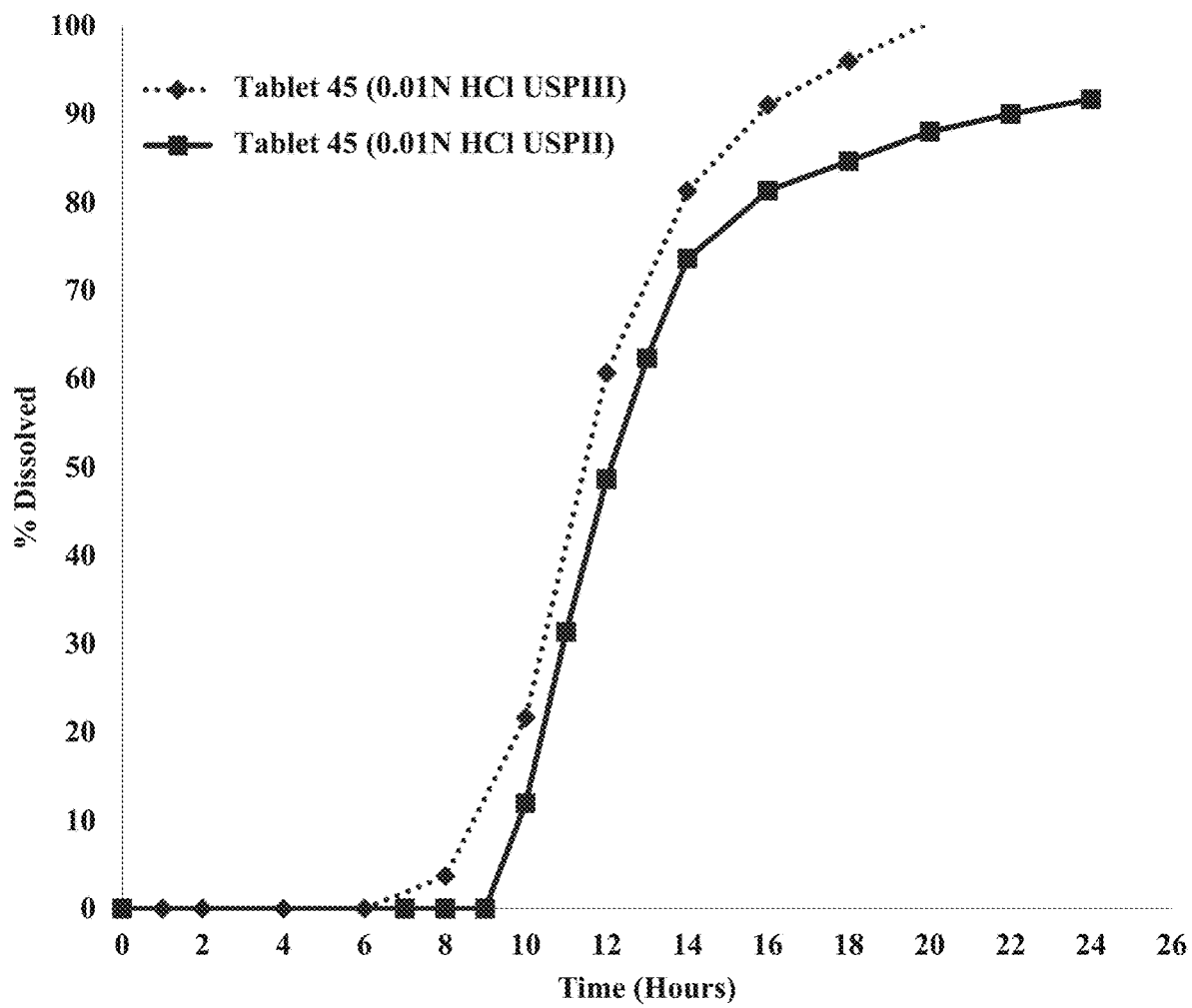

FIG. 21 shows the effect of changing hydrodynamics of the dissolution medium on lag time of Tablet 45, placed in about 900 ml of about 0.01N HCl for up to 24 hours, using USP Apparatus II (Sinkers), at 50 rpm and 37° C. Percentage drug dissolved is plotted over time (hours). Tablet 45 contains a drug:polymer weight ratio of about 40:60. The Figure demonstrates that there is no substantial change in lag time with changing hydrodynamics of the dissolution medium.

Figure 22:
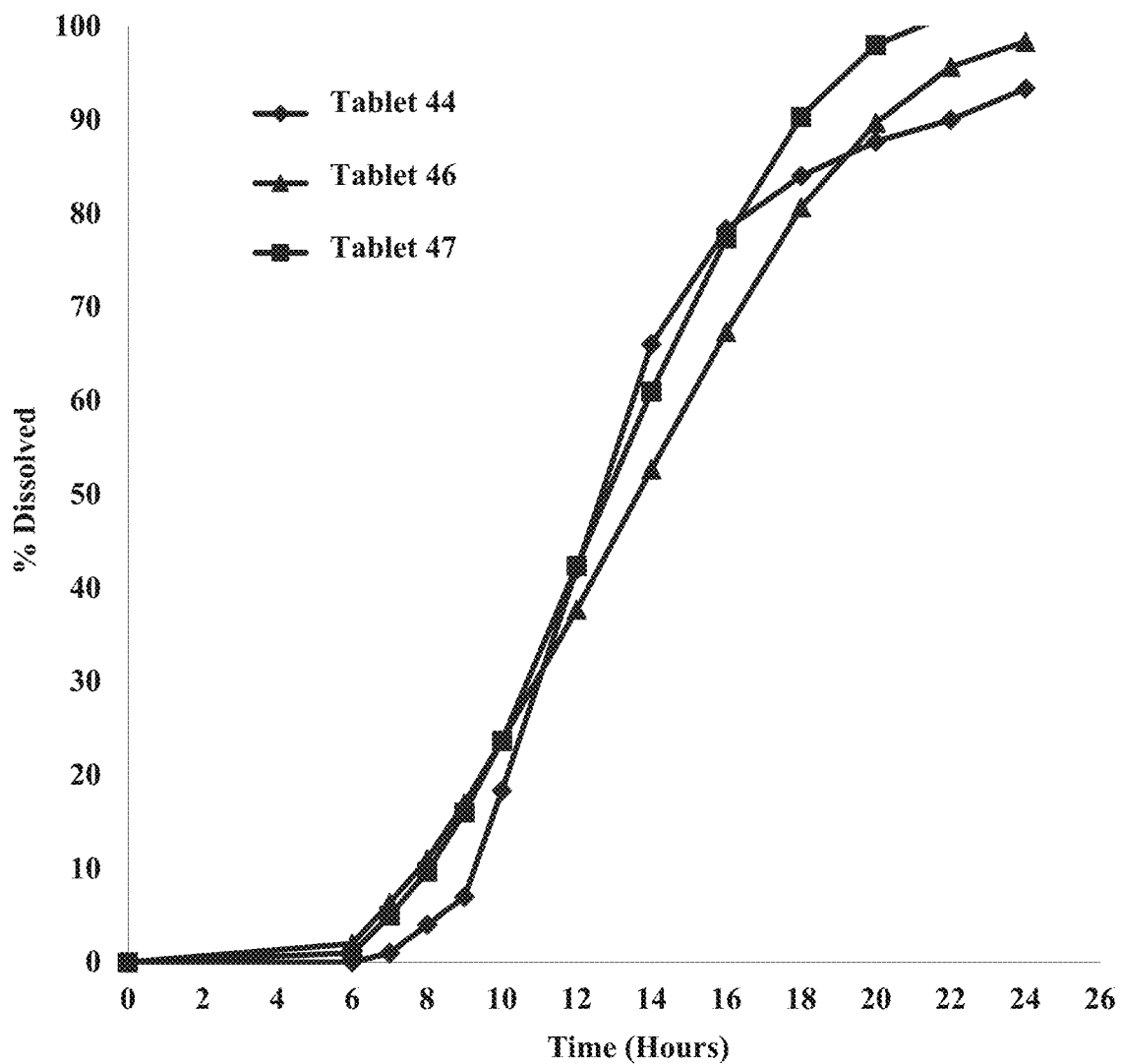

FIG. 22 shows effect of sodium chloride in placebo layer on lag time of Tablets 44, 46, and 47, placed in about 900 ml of about 0.01N HCl of tablets for up to 24 hours, using USP Apparatus II (Sinkers), at 50 rpm and 37° C. Percentage drug dissolved is plotted over time (hours). Tablet 44 contains 0% sodium chloride, Tablet 46 contains about 5% sodium chloride, and Tablet 47 contains about 10% sodium chloride in the placebo layer, based on the total weight of the placebo layer. The Figure demonstrates that presence of sodium chloride in placebo layer has negligible effect on lag time and release rate.

Figure 23:
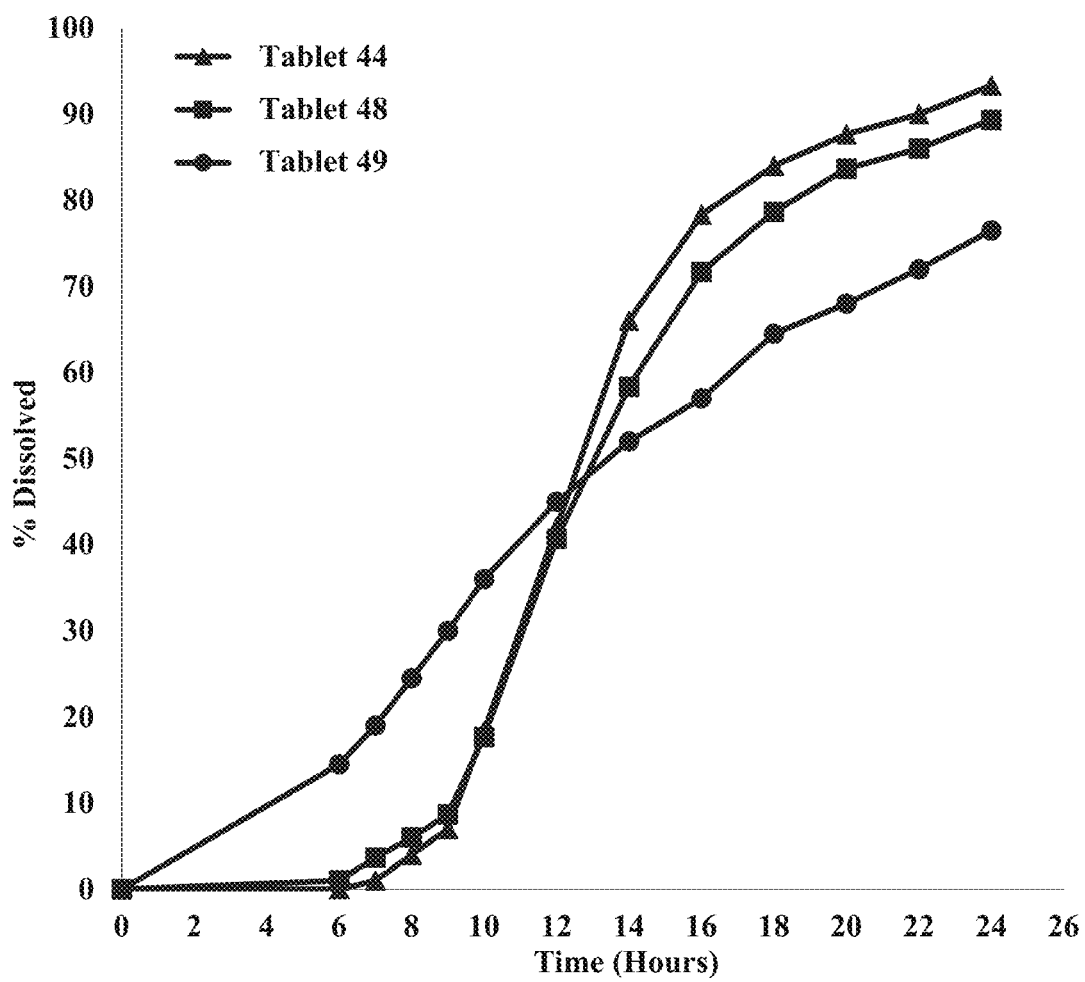

FIG. 23 shows the effect of POLYOX® grade in placebo layer on lag time of Tablets 44, 48, and 49, placed in about 900 ml of about 0.01N HCl for up to 24 hours, using USP Apparatus II (Sinkers), at 50 rpm and 37° C. Percentage drug dissolved is plotted over time (hours). Tablet 44 contains POLYOX® 1105 in the placebo layer; Tablet 48 contains POLYOX® N750 in the placebo layer; and Tablet 49 contains POLYOX® N80 in the placebo layer. The Figure demonstrates that the average molecular weight of POLYOX® in the placebo layer should be at least about 300K to provide a lag time of at least about 6 hours.

Figure 24:
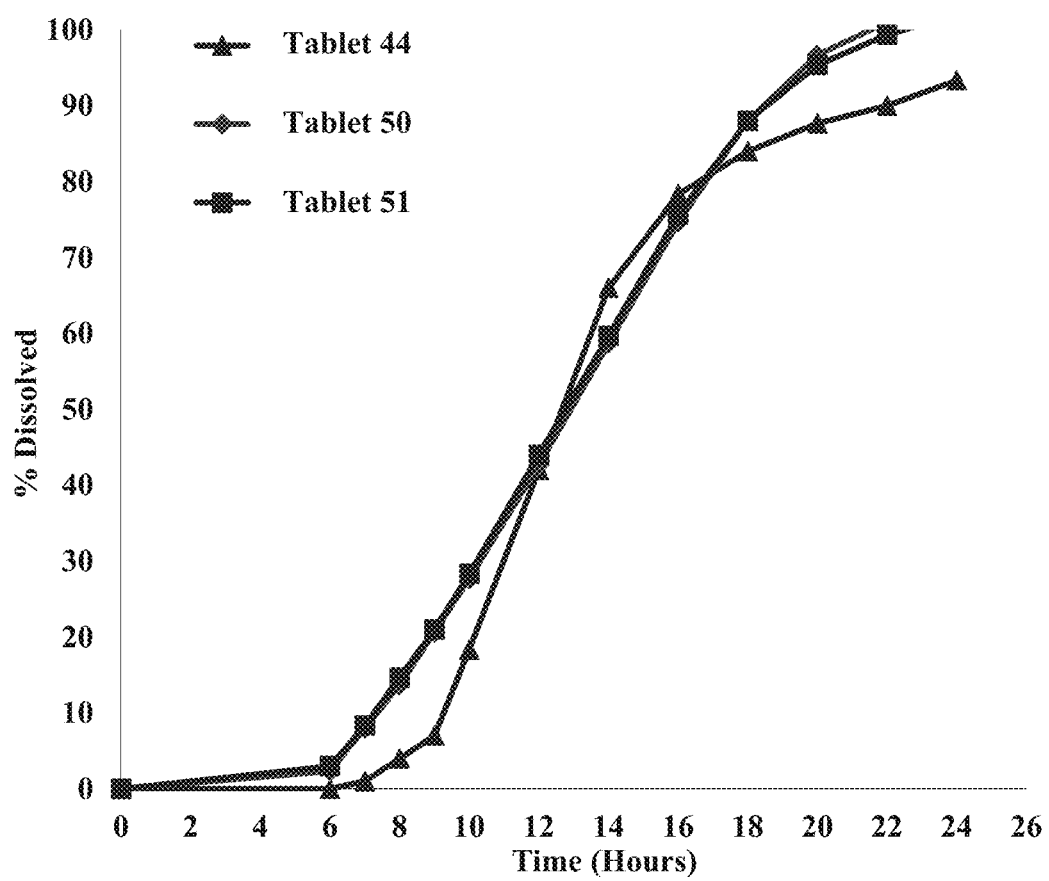

FIG. 24 shows the effect of POLYOX® grade/average molecular weight in push layer on release rate and drug recovery of Tablets 44, 50, and 51, placed in about 900 ml of about 0.01N HCl for up to 24 hours, using USP Apparatus II (Sinkers), at 50 rpm and 37° C. Percentage drug dissolved is plotted over time (hours). The figure compares release rate and drug recovery in compositions containing POLYOX® WSR 303 (7M), POLYOX® WSR 301 (3M), and POLYOX® WSR Coagulant (5M) in push layer. The figure demonstrates that compositions containing POLYOX® N750 in the placebo layer and POLYOX® WSR 301 in the push layer or compositions containing POLYOX® N80 in the placebo layer and POLYOX® WSR Coagulant in the push layer provide higher drug recovery, compared to compositions containing POLYOX® 1105 in the placebo layer and POLYOX® WSR 303 in the push layer.

Figure 25:
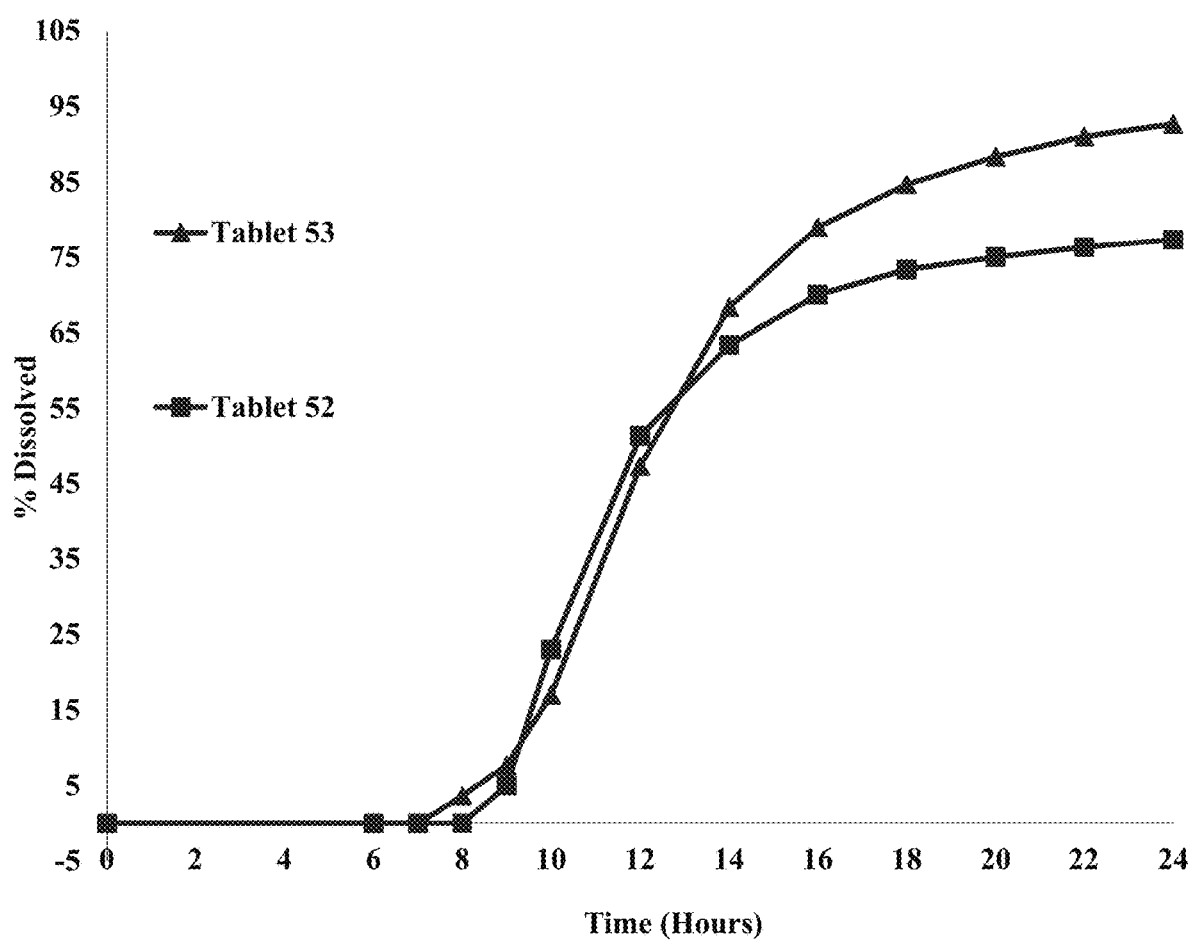

FIG. 25 shows the effect of the presence of a wicking agent and an osmogen in the placebo layer on lag time of Tablets 52 and 53, placed in about 900 ml of about 0.01N HCl, using USP Apparatus II (Sinkers), at 50 rpm and 37° C. Percentage drug dissolved is plotted over time (hours). The Figure demonstrates that addition of a wicking agent and sodium chloride in the placebo layer reduces the drug recovery without substantially affecting lag time.

Figure 26:
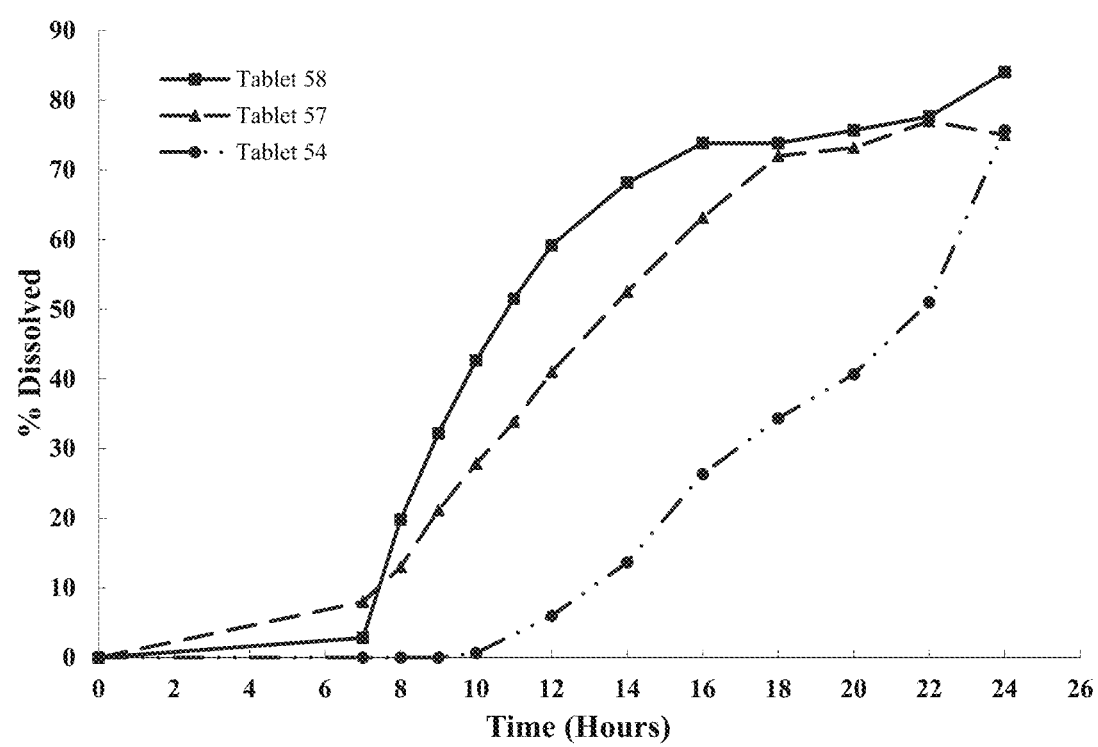

FIG. 26 provides dissolution profiles of Tablets 54, 57, and 58 in 5 ml of pH 6.8 buffer, using USP Apparatus II (Sinkers), at 5 rpm and 37° C. (low-volume, low-RPM condition). FIG. 26 demonstrates that Tablet 54, with about 10% coating weight gain, provides an improved release rate and improved drug recovery compared to Tablets 57 and 58, with about 12.5% coating weight gain. FIG. 26 further demonstrates that tablets with higher amount of pore former (Polyethylene glycol present in OPADRY® CA clear (90:10)) in the coating layer (e.g., Tablet 57), provide faster drug release compared to tablets containing less amount of pore former in OPADRY® CA clear (95:5) in the coating layer (e.g., Tablet 58), at a same coating weight gain. FIG. 26 also demonstrates that tablets containing POLYOX® 1105 in placebo layer and POLYOX® WSR 303 in push layer (Tablet 58) provided longer lag time compared to tablets containing POLYOX® 205 in placebo layer and POLYOX® WSR coagulant in the push layer (Tablets 54 and 57).

Figure 27:
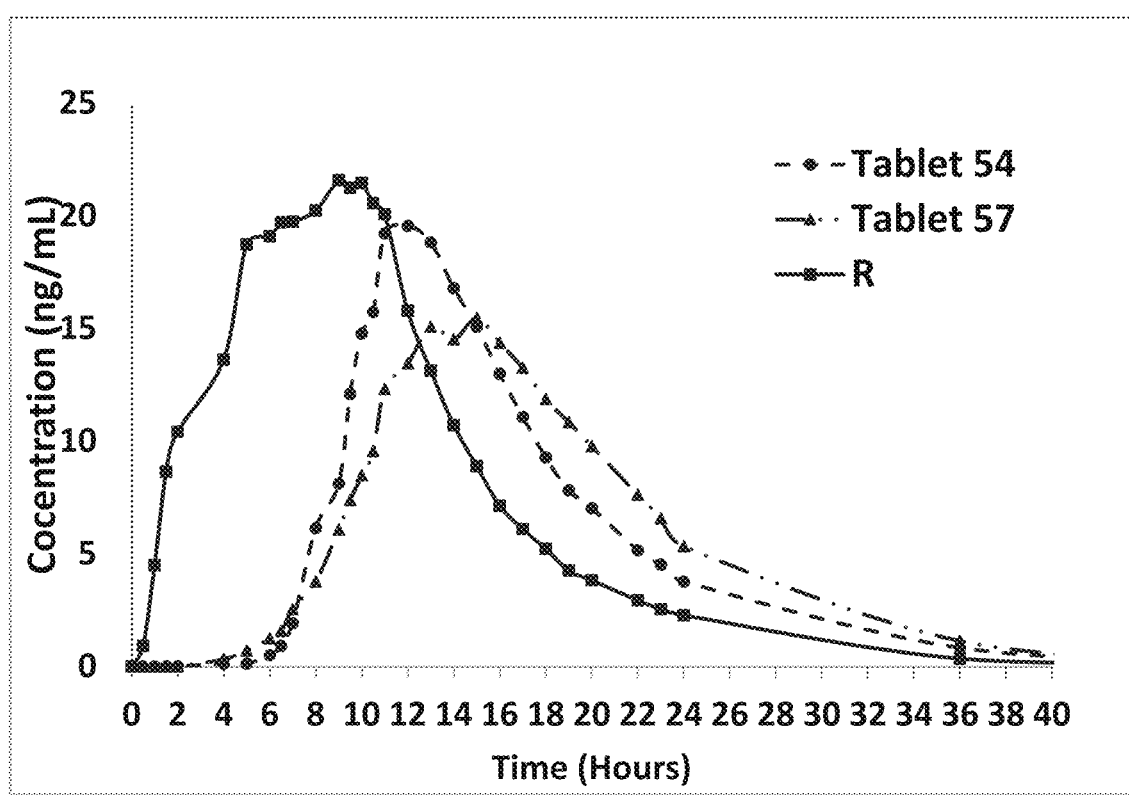

FIG. 27 compares pharmacokinetic performance of extended release compositions of the disclosure with marketed extended release methylphenidate product. FIG. 27 demonstrates that the compositions of the disclosure provide a lag time of about 7 hours and a $C_{max}$ of about 22 ng at 12 hours post administration.

6. DETAILED DESCRIPTION

The present disclosure is directed to delayed release methylphenidate compositions, amongst other things.

6.1. Definitions

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

The terminology used in the present disclosure is for the purpose of describing particular embodiments only and is not intended to be limiting.

As used herein, the use of the word "a" or "an" when used in conjunction with the term "comprising" in the claims and/or when used in the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 15%, up to 10%, up to 5%, up to 1%, up to 0.5%, or even up to 0.1% of a given value.

As used herein, a "therapeutically effective," "therapeutic," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject.

As used herein, the term "drug recovery" refers to percentage of the total amount of drug present in the dosage form that is released in a dissolution medium. The term "complete drug recovery" refers to release of about 90% to about 105% of the drug present in the dosage form.

The term "bioavailability" refers to the fraction of an administered dose of unchanged drug that reaches the systemic circulation.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

The term "chrono release" refers to drug release in a sequential order of time. In particular, the term "chrono release" means timed or programmed release of one or more drugs at a rhythm that matches the human circadian rhythm of a condition's symptoms and/or of the individual being treated in the application of the therapy to optimize the therapeutic outcome and minimize side effects. In certain embodiments, the term "chrono release" comprises immediate release of a drug followed by an extended release of the same or different drug.

The term "pulsatile release" means rapid release of discrete portions of drug in pulses that are separated by a well-defined lag time(s).

The term "lag time" means the time for which release of a drug is delayed from the time of administration/ingestion of the composition. Not more than about 20% of the maximum plasma concentration ($C_{max}$) of the drug is released during the lag time.

The term "release rate" refers to the quantity of drug released per unit time, e.g., mg of drug released per hour (mg/hour), from a dosage form. Drug release rates are calculated under in vitro dosage form dissolution testing conditions known in the art.

The term "delayed release" means release of a discrete portion(s) of a drug at a time(s) other than immediately after administration/ingestion.

The term "immediate release" means substantially complete release of a drug within a time period of about 1 hour or less, preferably within 30 minutes or less, post-administration.

The term "immediate release drug layer" means an immediate release coating layer comprising a drug and at least one pharmaceutically acceptable carrier. The immediate release drug layer dissolves rapidly upon administration and provides an immediate release dose of the drug.

The term "controlled release" means drug release that is controlled to alter the timing and/or rate of release of the drug substance from that of a conventional immediate release dosage form. The controlled release dosage forms of the disclosure can include modified release dosage forms providing delayed release (DR), extended release (ER), target release (TR), pulsatile release, chrono release, or any combination thereof, of drug substance.

The term "extended release" refers to modified release dosage forms or compositions that are formulated to allow the drug to be available over an extended period of time after administration, thereby allowing a reduction in dosing frequency, as compared to a drug presented as an immediate release dosage form.

The terms "gastric medium," "simulated gastric fluid," "simulated intestinal fluid," "intestinal medium," and the like, as used herein, refer to media occurring in stomach and in intestines, correspondingly, or to the solutions that are used to mimic their chemical environment in vitro.

As used herein, the term "dissolution medium" refers to a medium used to mimic pH of gastric fluid in fed or fasted state of an individual. In certain embodiments, the medium used to mimic fed state of an individual includes pH 6.8 acetate buffer; and the medium used to mimic fasted state of an individual includes 0.01 N HCl.

The term "solubility" is defined in terms of ability to dissolve in water. The term "highly soluble" includes drugs with a solubility of greater than 100 mg/ml of water; the term "moderately soluble" includes drugs with a solubility of between 100 mg/ml and 1 mg/ml of water; the term "sparingly soluble" includes drugs with a solubility of between 1 mg/ml and 0.1 mg/ml of water.; and the term "insoluble" includes drugs with a solubility of less than 0.1 mg/ml of water.

The term "osmosis" refers to a spontaneous movement of a solvent from a solution of lower solute concentration to a solute or a solution of higher solute concentration through a semipermeable membrane, wherein the membrane is permeable to the solvent and impermeable to the solute.

The term "osmotic pressure" refers to a pressure exerted on a higher solvent concentration side of the dosage form to inhibit solvent flow into the dosage form.

The term "substantially free", as used herein, refers to excluding any functional (e.g., noncontaminating) amount, i.e., any amount that contributes or has an effect on release profile or lag time of the composition.

The term "semipermeable membrane", as used herein, refers to a membrane or film that is substantially impermeable to the passage of solutes, e.g., a drug and other excipients, and substantially permeable to passage of fluids. As used herein, the terms functional coat and semipermeable membrane are used interchangeably.

The term "coating weight gain", as used herein, refers to coating weight gain with respect to the weight of the uncoated tablet. For example, a coating weight gain of 15% refers to a 15 wt % increase in tablet weight during coating with respect to the uncoated tablet weight.

The terms "pore former" and the like, as used herein, refer to water-soluble polymers and/or water-soluble small molecules that will form pores or channels (i.e., behave as a channeling agent) in a semipermeable membrane to improve permeability of the membrane.

The terms "shear" and "shear effect," as used interchangeably herein, refer to peristaltic waves, particularly under fed conditions, moving from the mid-corpus of the stomach to the pylorus. Dissolution of compositions using USP Apparatus II (Sinkers) at 50 rpm and 37° C. and using USP Apparatus III (Biodis) at 25 dpm and 37° C., mimics the effects of stomach shear on the dissolution rate of the composition.

The terms "orifice," "hole", and "delivery port," as used interchangeably herein, refer to an opening/exit means in coatings, e.g., in the semipermeable membrane coat, the seal coat, and/or the overcoat, of an osmotic-controlled composition facing the placebo layer. The appropriate opening can be formed by any means, e.g., by manual or laser drilling of the membrane. In certain embodiments, the semipermeable membrane facing the top of the placebo layer is completely removed to provide an orifice comprising an optimum diameter that is equivalent to the diameter of the top of the placebo layer end of the multilayer core. In certain embodiments, the optimum orifice diameter is from about 0.6 mm and about 1.5 mm.

The term "osmotic agent" as used herein, refers to swellable hydrophilic polymers, and osmogens/ionic compounds consisting of inorganic salts.

The term "wicking agent" as used herein, refers to a material with the ability to draw water into the porous network of the osmotic composition. The wicking agent helps to increase the contact surface area of the drug with the incoming aqueous fluid.

The term "patient" or "subject," as used herein, refers to a human or nonhuman mammal that is in need or may be in need to receive an osmotic dosage form of the present disclosure.

The terms "drug," "active agent," "active ingredient," and "active pharmaceutical ingredient/agent" are used interchangeably herein and include compounds that will elicit a therapeutically useful response in a subject; such terms include all polymorphs, prodrugs, solvates, hydrates, pharmaceutically acceptable salts, esters, and functionally equivalent chemical compounds.

The terms "methylphenidate" and "methylphenidate hydrochloride" are used interchangeably herein. The term "methylphenidate" includes all pharmaceutically acceptable salts, polymorphs, solvates, hydrates, esters, and functionally equivalent chemical compounds.

The terms "clonidine" and "clonidine hydrochloride" are used interchangeably herein. The term "clonidine" includes all pharmaceutically acceptable salts, esters, and functionally equivalent chemical compounds.

6.2 Multi-layer Osmotic Tablet Core

The present disclosure provides programmable osmotic-controlled oral compositions comprising a multilayer core (e.g., a multilayer tablet core) comprising a drug, wherein the core is coated with a semipermeable membrane comprising an orifice and, optionally, an immediate release coating comprising a drug for immediate release, over the semipermeable membrane. The multilayered tablet core comprises a pull layer containing the drug and a push layer. The pull layer comprises at least two layers: a placebo layer, for providing a desired lag time for drug release; and an active layer containing the drug and providing a delayed controlled release of the drug. In certain embodiments, the orifice is present on the placebo layer side of the multilayer tablet core. In certain embodiments, the delayed controlled release is a delayed extended release. In certain embodiments, the tablets are vertically compressed producing a capsule-shaped product. In certain embodiments, such shape ensures complete extrusion of drug from the orifice.

For any of the dosage forms, compositions, and methods of the disclosure, the push layer is present in an amount that expands in volume to a size that pushes the entire drug solution or suspension in the pull layer, e.g., the placebo and active layers, out of the tablet through a delivery port/orifice, providing, e.g., complete drug recovery from the dosage form. In certain embodiments, the pull layer and the push layer are present in a ratio of about 2:1, about 1.5:1, about 1:1, or any intermediate values therein. In certain embodiments, the weight of the placebo layer, the active layer, or the push layer is from about 10 wt % to about 60 wt %, based on the total weight of the trilayer core. In certain embodiments, the weight of the placebo layer is from about 10 wt % to about 50 wt %, based on the total weight of the trilayer core. In certain embodiments, the weight of the active layer is from about 10 wt % to about 60 wt %, based on the total weight of the trilayer core. In certain embodiments, the weight of the push layer is from about 10 wt % to about 50 wt %, based on the total weight of the trilayer core. Furthermore, each of the layers, i.e., the active layer, the placebo layer, and the push layer, can comprise polyethylene oxide (e.g., POLYOX®).

In certain embodiments, the placebo layer and the push layer are free of any active pharmaceutical ingredient. In certain embodiments, the active pharmaceutical ingredient contained in the active layer does not leach/migrate into the placebo layer or the push layer during the in vitro drug release test. In certain embodiments, less that about 20 wt %, less than about 15 wt %, less than about 10 wt %, less than about 5 wt %, or less than about 1 wt % of the total weight of the active pharmaceutical ingredient is released along with the placebo layer. In certain embodiments, less that about 20 wt %, less than about 15 wt %, less than about 10 wt %, less than about 5 wt %, less than about 4 wt %, less than about 3 wt %, less than about 2 wt %, or less than about 1 wt % of the active pharmaceutical ingredient, based on the total weight of the active pharmaceutical agent in the dosage form, is released between about 2 hours and about 10 hours, between about 2 hours and about 8 hours, between about 2 hours and about 7 hours, or between about 2 hours and about 6 hours following administration of the dosage form, thereby providing a lag time.

Placebo Layer

In certain embodiments, the placebo layer/placebo layer blend, is located adjacent to and continuity with the orifice in the semipermeable membrane. In certain embodiments, the placebo layer blend comprises a swellable hydrophilic polymer, e.g., POLYOX® with an average molecular weight of from about 300,000 Da to about 900,000 Da, a binder, a lubricant, and a glidant. In certain embodiments, the placebo layer further comprises a color pigment. In certain embodiments, the placebo layer blend is substantially free of any active pharmaceutical ingredient. In certain embodiments, the placebo layer contains less than about 30 wt %, less than about 25 wt %, less than about 20 wt %, less than about 15 wt %, less than about 10 wt %, less than about 5 wt %, less than 4 wt %, less than about 3 wt %, less than 2 wt %, less than 1 wt %, or any intermediate values therein, of the active pharmaceutical ingredient, based on the total weight of the core.

In certain embodiments, the placebo layer blend further includes a stabilizer to prevent degradation of polyethylene oxide polymer, e.g., POLYOX®. In certain embodiments, the placebo layer blend further includes at least one osmogen and/or at least one wicking agent. In certain embodiments, placebo layer blend includes granules and extragranular excipients. In certain embodiments, the granules comprise a swellable hydrophilic polymer, a binder, an osmogen, a stabilizer, and a color pigment. In certain embodiments, granules further include a wicking agent. In certain embodiments, glidant and lubricant are present as extragranular excipients in the placebo layer. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 60:40 and about 99:1. In certain embodiments, the placebo layer blend is made by dry granulation/slugging. In certain embodiments, the placebo layer is made by direct compaction In certain embodiments, the molecular weight/grade of the POLYOX® in the placebo layer affects drug recovery, lag time, and/or release profile, of the composition. In certain embodiments, the POLYOX® has an average molecular weight of < about 1M, e.g., about 100K (POLYOX® N-10), about 200K (POLYOX® N-80), about 300K (POLYOX® N-750), about 600K (POLYOX® N-205), about 900K (POLYOX® N-1105), or intermediate values thereof.

In certain embodiments, the viscosity of the placebo layer can be adjusted to provide a desired and consistent lag time. In certain embodiments, the viscosity of the placebo layer depends upon the average molecular weight of the POLYOX® present in the placebo layer. In certain embodiments, the placebo layer contains POLYOX® 205 or POLYOX® 1105. In certain embodiments, the placebo layer contains POLYOX® 1105. In certain embodiments, the placebo layer contains POLYOX® 205. In certain embodiments, the POLYOX® is present in an amount of from about 50 wt % to about 99 wt %, from about 50 wt % to about 95 wt %, from about 50 wt % to about 90 wt %, from about 50 wt % to about 85 wt %, from about 50 wt % to about 80 wt %, from about 50 wt % to about 75 wt %, from about 50 wt % to about 70 wt %, from about 50 wt % to about 65 wt %, from about 50 wt % to about 60 wt %, from about 55 wt %, to about 99 wt %, from about 60 wt % to about 99 wt %, from about 65 wt % to about 99 wt %, from about 70 wt % to about 99 wt %, from about 75 wt % to about 99 wt %, from about 80 wt % to about 99 wt %, from about 85 wt % to about 99 wt %, from about 90 wt % to about 99 wt %, from about 95 wt % to about 99 wt %, from about 55 wt % to about 95 wt %, from about 60 wt % to about 85 wt %, from about 65 wt % to about 80 wt %, or from about 70 wt % to about 75 wt %, based on the total weight of the placebo layer. In certain embodiments, the POLYOX® is present in an amount of about 50 wt %, about 55 wt %, about 60 wt %, about 65 wt %, about 70 wt %, about 75 wt %, about 80 wt %, about 81 wt %, about 82 wt %, about 83 wt %, about 84 wt %, about 85 wt %, about 86 wt %, about 87 wt %, about 88 wt %, about 89 wt %, about 90 wt %, about 91 wt %, about 92 wt %, about 93 wt %, about 94 wt %, about 95 wt %, about 96 wt %, about 97 wt %, about 98 wt %, about 99 wt %, or any intermediate values therein, based on the total weight of the placebo layer.

In certain embodiments, the placebo layer comprises binders comprising, but not limited to, povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, pegylated polyvinyl alcohol, or any combination thereof. In certain embodiments, the binder is povidone. In certain embodiments, the binders are present in an amount of about 0.5 wt % to about 50 wt % of the placebo layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, about 50 wt %, or any intermediates values therein, based on the total weight of the placebo layer.

In certain embodiments, the placebo layer includes at least one stabilizer to prevent/slow the degradation of POLYOX®. In certain embodiments, the stabilizer comprises antioxidants including ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the antioxidant is BHT. In certain embodiments, the stabilizer is present in an amount of about 0.01 wt % to about 0.5 wt % of the placebo layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.10 wt %, about 0.2 wt %, about 0.3 wt %, about 0.4 wt %, about 0.5 wt %, or any intermediate values therein, based on the total weight of the placebo layer.

In certain embodiments, the placebo layer comprises at least one lubricant including magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combination thereof. In certain embodiments, the lubricant is magnesium stearate or steric acid. In certain embodiments, the placebo layer comprises at least one lubricant as an extragranular excipient. In certain embodiments, the lubricant is present in an amount of about 0.5 wt % to about 2 wt %, based on the total weight of the placebo layer. In certain embodiments, the lubricant is present in an amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the placebo layer.

In certain embodiments, the placebo layer comprises at least one glidant, including talc, colloidal silicon dioxide, magnesium trisilicate, powdered cellulose, starch, tribasic calcium phosphate, or any combinations thereof. In certain embodiments, the glidant is colloidal silicon dioxide. In certain embodiments, the placebo layer comprises at least one glidant as an extragranular excipient. In certain embodiments, the glidant is present in an amount of from about 0.05 wt % to about 5 wt %, from about 0.1 wt % to about 5 wt %, from about 0.5 wt % to about 5 wt %, from about 1 wt % to about 5 wt %, from about 1.5 wt % to about 5 wt %, from about 2 wt % to about 5 wt %, from about 2.5 wt % to about 5 wt %, from about 3 wt % to about 5 wt %, from about 3.5 wt % to about 5 wt %, from about 4 wt % to about 5 wt %, from about 4.5 wt % to about 5 wt %, from about 0.05 wt % to about 4.5 wt %, from about 0.05 wt % to about 4.0 wt %, from about 0.05 wt % to about 3.5 wt %, from about 0.05 wt % to about 3.0 wt %, from about 0.05 wt % to about 2.5 wt %, from about 0.05 wt % to about 2.0 wt %, from about 0.05 wt % to about 1.5 wt %, from about 0.05 wt % to about 1.0 wt %, from about 0.05 wt % to about 0.5 wt %, from about 0.05 wt % to about 0.1 wt %, from about 0.1 wt % to about 4.5 wt %, from about 1 wt % to about 4 wt %, or from about 1.5 wt % to about 3 wt %, based on the total weight of the placebo layer. In certain embodiments, the glidant is present in an amount of about 0.05 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the placebo layer.

In certain embodiments, the placebo layer includes at least one color pigment. In certain embodiments, the color pigment in the placebo layer is useful for distinguishing the placebo layer from the active layer. In certain embodiments, the color pigment comprises iron oxide or lake-based colors. In certain embodiments, the pigment is a lake-based color. In certain embodiments, the pigment is an iron oxide pigment, e.g., oxide pigment red or oxide pigment black. In certain embodiments, the pigment is present in an amount of about 0.01 wt % to about 0.5 wt %, based on the total weight of the placebo layer.

In certain embodiments, the placebo layer further comprises osmogens, any disintegrants or water-entraining agents/wicking agents.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of from about 5 wt % to about 40 wt %, based on the total weight of the placebo layer. In certain embodiments, the osmogen is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the placebo layer.

In certain embodiments, the placebo layer comprises at least one wicking agent selected from the group comprising crospovidone, croscarmellose sodium, carmellose calcium, polyvinyl pyrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 5 wt % to about 40 wt %, based on the total weight of the placebo layer. In certain embodiments, the wicking agent is present in an amount of 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the placebo layer.

In certain embodiments, the relative weight percentage of the placebo layer, based on the total weight of the uncoated trilayer core, can be between about 10 wt % and about 60 wt %, between about 10 wt % and about 55 wt %, or between about 10 wt % and about 50 wt %.

Active Layer

In certain embodiments, the active layer is located between (and adjacent to) and in contact with the placebo layer and the push layer. In certain embodiments, the active layer/active layer blend includes an active agent, a swellable hydrophilic polymer, a binder, an osmogen, and a lubricant. In certain embodiments, the active layer/active layer blend further includes a glidant and/or a stabilizer. In certain embodiments, active layer blend includes granules containing an active agent, a swellable hydrophilic polymer, a binder, an osmogen, a stabilizer, and a color pigment. In certain embodiments, granules further include a surfactant and/or a wicking agent. In certain embodiments, the glidants and the lubricants are present as extragranular excipients in the active layer blend.

In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying weight ratios. In certain embodiments, the granulation solvent is a hydroalcoholic solvent containing dehydrated alcohol:water weight ratio of between about 60:40 and about 99:1. In certain embodiments, the placebo layer blend is made by dry granulation/slugging. In certain embodiments, the placebo layer is made by direct compaction In certain embodiments, the swellable hydrophilic polymers include polyethylene oxide, carbopols, polyacrylamides, acrylate polymer polysaccharide composed of condensed glucose units, crospovidone, carboxymethyl cellulose, and poly(alkalicarboxymethylcellulose), Methocel™ K100LVCR (methylcellulose and hydroxypropyl methyl cellulose), and any combinations thereof. In certain embodiments, the swellable hydrophilic polymers comprise polyethylene oxide polymers with an average molecular weight of from about 100,000 Da to about 600,000 Da. In certain embodiments, the polyethylene oxide polymer has an average molecular weight of about 100,000 Da (POLYOX® N-10), about 200,000 Da (POLYOX® N-80), about 300,000 Da (POLYOX® N-750), or about 600.00 Da. In certain embodiments, the average molecular weight of POLYOX® is about 200,000 Da.

In certain embodiments, the viscosity of the active layer is adjusted to provide a desired and consistent release profile. In certain embodiments, the viscosity of active layer depends upon the average molecular weight/grade of the POLYOX® present in the active layer. In certain embodiments, the active layer contains POLYOX® N-80 (200K). In certain embodiments, the POLYOX® is present in an amount of from about 30 wt % to about 80 wt %, from about 35 wt % to about 80 wt %, from about 40 wt % to about 80 wt %, from about 45 wt %, to about 80 wt %, from about 50 wt % to about 80 wt %, from about 55 wt % to about 80 wt %, from about 60 wt % to about 80 wt %, from about 65 wt % to about 80 wt %, from about 70 wt % to about 80 wt %, from about 75 wt % to about 80 wt %, from about 50 wt % to about 75 wt %, from about 50 wt % to about 70 wt %, from about 50 wt % to about 65 wt %, from about 50 wt % to about 60 wt %, from about 50 wt % to about 55 wt %, from about 55 wt % to about 75 wt %, or from about 60 wt % to about 70 wt % of the active layer. In certain embodiments, the POLYOX® is present in an amount of about 40 wt %, about 45 wt %, about 50 wt %, about 55 wt %, about 60 wt %, about 65 wt %, about 70 wt %, about 75 wt %, about 80 wt %, or intermediate values therein, based on the total weight of the active layer.

In certain embodiments, drug to POLYOX® weight ratio, in the active layer, affects the lag time, release rate, and drug recovery of the composition. In certain embodiments, release rate and drug recovery from the composition increases with increasing the drug to POLYOX® weight ratio. In certain embodiments, lag time decreases with increasing drug to POLYOX® weight ratio. In certain embodiments, the ratio of the drug and POLYOX® is between about 10:90 and about 90:10. In certain embodiments, the weight ratio of the drug and POLYOX® is about 10:90, about 20:80, about 30:70, about 40:60, about 50:50, about 60:40, about 70:30, about 80:20, about 90:10, or intermediate values therein. In certain embodiments, the drug:POLYOX® weight ratio is from about 20:80 and about 70:30.

In certain embodiments, the active layer further includes low viscosity hypromellose or hypromellose acetate succinate as a wicking agent to enhance wettability of drugs with low aqueous solubility. In certain embodiments, the low viscosity hypromellose or povidone are used as binders, and stearic acid is used as a lubricant.

In certain embodiments, the active layer comprises binders including povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide, polyethylene glycol, alginates, pegylated polyvinyl alcohol, or any combination thereof. In certain embodiments, the binder is povidone. In certain embodiments, the binders are present in an amount of about 0.5 wt % to about 30 wt %, 0.5 wt % to about 29 wt %, from about 0.5 wt % to about 28 wt %, from about 0.5 wt % to about 27 wt %, from about 0.5 wt % to about 26 wt %, from about 0.5 wt % to about 25 wt %, from about 0.5 wt % to about 24 wt %, from about 0.5 wt % to about 23 wt %, from about 0.5 wt % to about 22 wt %, from about 0.5 wt % to about 21 wt %, from about 0.5 wt % to about 20 wt %, from about 0.5 wt % to about 19 wt %, from about 0.5 wt % to about 18 wt %, from about 0.5 wt % to about 17 wt %, from about 0.5 wt % to about 16 wt %, from about 0.5 wt % to about 15 wt %, from about 0.5 wt % to about 14 wt %, from about 0.5 wt % to about 13 wt %, from about 0.5 wt % to about 12 wt %, from about 0.5 wt % to about 11 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, from about 1 wt % to about 20 wt %, from about 2 wt %, to about 20 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the active layer.

In certain embodiments, the active layer comprises osmogens and/or any disintegrants or water-entraining agents/wicking agents. In certain embodiments, the active layer comprises at least one osmogen. In certain embodiments, the osmogen includes ionic compounds of inorganic salts that provide a concentration differential for osmotic flow of liquid into the composition. In certain embodiments, the osmogen comprises an ionic compound including sodium chloride, potassium chloride, potassium sulfate, lithium sulfate, sodium sulfate, a lactose and sucrose combination, a lactose and dextrose combination, sucrose, dextrose, mannitol, dibasic sodium phosphate, and any combination thereof. In certain embodiments, the osmogen is sodium chloride. In certain embodiments, the osmogen is present in an amount of from about 2 wt % to about 40 wt %, from about 2 wt % to about 35 wt %, from about 2 wt % to about 30 wt %, from about 2 wt % to about 25 wt %, from about 2 wt % to about 20 wt %, from about 2 wt % to about 19 wt %, from about 2 wt % to about 18 wt %, from about 2 wt % to about 17 wt %, from about 2 wt % to about 16 wt %, from about 2 wt % to about 15 wt %, from about 2 wt % to about 14 wt %, from about 2 wt % to about 13 wt %, from about 2 wt % to about 12 wt %, from about 2 wt % to about 11 wt %, from about 2 wt % to about 10 wt %, from about 2 wt % to about 9 wt %, from about 2 wt % to about 8 wt %, from about 2 wt % to about 7 wt %, from about 2 wt % to about 6 wt %, from about 2 wt % to about 5 wt %, from about 2 wt % to about 4 wt %, from about 2 wt % to about 3 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the active layer. In certain embodiments, the osmogen is present in an amount of about 2 wt %, about 3 wt %, about 4 wt %, about 5 wt %, about 6 wt %, about 7 wt %, about 8 wt %, about 9 wt %, about 10 wt %, about 15 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the active layer.

In certain embodiments, the active layer comprises at least one wicking agent selected from the group comprising crospovidone, croscarmellose sodium, carmellose calcium, polyvinyl pyrolidone, low-substituted hydroxypropyl celluloses, sodium starch glycolate, alginic acid and alginates, acrylic acid derivatives, corn starch, maize starch, modified starches, and combinations thereof. In certain embodiments, the wicking agent is crospovidone. In certain embodiments, the wicking agent is present in an amount of from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 20 wt %, from about 15 wt % to about 20 wt %, or from about 10 wt % to about 15 wt %, based on the total weight of the active layer. In certain embodiments, the wicking agent is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the active layer.

In certain embodiments, the active layer includes at least one stabilizer to prevent/reduce the degradation of POLYOX®. In certain embodiments, the stabilizer comprises an antioxidant and/or a pH modifying agent. In certain embodiments, the pH modifying agent is an acid or a base. In certain embodiments, the stabilizer is an antioxidant and a pH modifying agent. In certain embodiments, the stabilizer comprises an antioxidant including one or more of ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, and propyl gallate. In certain embodiments, the antioxidant is BHT. In certain embodiments, additional stabilizers, e.g., pH modifiers, can be added to stabilize the active agent. In certain embodiments, the stabilizer is present in an amount of about 0.01 wt % to about 0.5 wt %, from about 0.1 wt % to about 0.5 wt %, from about 0.2 wt % to about 0.5 wt %, from about 0.3 wt % to about 0.5 wt %, from about 0.4 wt % to about 0.5 wt %, from about 0.01 wt % to about 0.5 wt %, from about 0.01 wt % to about 0.4 wt %, from about 0.01 wt % to about 0.3 wt %, from about 0.01 wt % to about 0.2 wt %, from about 0.01 wt % to about 0.1 wt %, or from about 0.05% to about 0.3 wt %, based on the total weight of the active layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, based on the total weight of the active layer.

In certain embodiments, the active layer further includes surfactants to modulate the solubility of the active agent. In certain embodiments, the surfactant comprises one or more of esters of fatty acids; sorbitan fatty acid esters ethoxylated with from about 2 to about 30 moles of ethylene oxide; polyethylene glycol fatty acid esters; polyethylene glycol esters and polyethylene glycol ethers; and polyethoxylated carboxylic acids, PEG-7 hydrogenated castor oil, and PEG-30 dipolyhydroxystearate; block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; and polyoxyl 40 stearate.

In certain embodiments, the active layer comprises lubricants including magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, or any combination thereof. In certain embodiments, the lubricant is present in an amount of about 0.01 wt % to about 2 wt %, from about 0.01 wt % to about 1.5 wt %, from about 0.01 wt % to about 1.0 wt %, from about 0.01 wt % to about 0.5 wt %, from about 0.01 wt % to about 0.1 wt %, from about 0.1 wt % to about 2 wt %, from about 1.0 wt % to about 2.0 wt %, from about 1.5 wt % to about 2.0 wt %, from about 0.1 wt % to about 1.0 wt %, or from about 0.5 wt % to about 1.5 wt % based on the total weight of the active layer. In certain embodiments, the lubricant is present in an amount of about 0.01 wt %, about 0.02 wt %, about 0.03 wt %, about 0.04 wt %, about 0.05 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the active layer.

In certain embodiments, the active layer comprises glidants including talc, colloidal silicon dioxide, magnesium trisilicate, powdered cellulose, starch, tribasic calcium phosphate, or a mixture thereof. In certain embodiments, the glidant is colloidal silicon dioxide. In certain embodiments, the glidant is present in an amount of about 0.05 wt % to about 5 wt %, from about 0.05 wt % to about 4 wt %, from about 0.05 wt % to about 3 wt %, from about 0.05 wt % to about 2 wt %, from about 0.05 wt % to about 1.0 wt %, from about 0.05 wt % to about 0.5 wt %, from about 0.1 wt % to about 5 wt %, from about 1.0 wt % to about 5 wt %, from about 1.5 wt % to about 5 wt %, from about 2.0 wt % to about 5 wt %, from about 2.5 wt % to about 5 wt %, from about 3.0 wt % to about 5 wt %, from about 3.5 wt % to about 5 wt %, from about 4.0 wt % to about 5 wt %, from about 4.5 wt % to about 5 wt %, from about 0.1 wt % to about 4.5 wt %, from about 1 wt % to about 4 wt %, or from about 1.5 wt % to about 3 wt %, based on the total weight of the active layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the active layer.

In certain embodiments, the relative weight percentage of the active layer, based on the total weight of the uncoated trilayer core, can be between about 10 wt % and about 60 wt %, between about 15 wt % and about 50 wt %, between about 20 wt % and about 45 wt %, between about 25 wt % and about 40 wt %, or about 30 wt %.

Push Layer

In certain embodiments, the push layer is located adjacent to the active layer. In certain embodiments, the push layer/push layer blend includes a swellable hydrophilic polymer, a binder, an osmogen, a lubricant, and a color pigment. In certain embodiments, the push layer/push layer blend further includes a glidant and/or a stabilizer. In certain embodiments, the push layer blend includes granules containing a swellable hydrophilic polymer, a binder, an osmogen, a stabilizer, and a color pigment. In certain embodiments, the glidants and the lubricants are present as extragranular excipients in the push layer blend. In certain embodiments, the granulating solvent for making granules comprises alcoholic solvent comprising absolute alcohol. In certain embodiments, the granulation solvent comprises a hydroalcoholic solvent comprising absolute alcohol and deionized water in varying weight ratios. In certain embodiments, the granulation solvent is a hydroalcoholic solvent containing absolute alcohol:water weight ratio of between about 60:40 and about 99:1. In certain embodiments, the push layer blend is made by dry granulation/slugging. In certain embodiments, the push layer is made by direct compaction.

In certain embodiments, the push layer does not include any drug. In certain embodiments, the swellable hydrophilic polymer is a polyethylene oxide polymer having an average molecular weight of greater than or equal to 1000,000 Da.

In certain embodiments, the average molecular weight of the polyethylene oxide polymer in the push layer is about 1000,000 Da (POLYOX® WSR N 12K), about 2000,000 Da (POLYOX® WSR N 60K), about 4000,000 Da (POLYOX® WSR 301), about 5000,000 Da (POLYOX® WSR coagulant), about 7000,000 Da (POLYOX® WSR 303), or any intermediate values therein. In certain embodiments, swelling of POLYOX® WSR coagulant (5M) can be enhanced by mixing with a portion of POLYOX® WSR 303 (7M). In certain embodiments, swelling of POLYOX® coagulant can be reduced by mixing with a portion of POLYOX® WSR 301 (4M). In certain embodiments, the POLYOX® is present in an amount of about 40 wt % to about 80 wt %, from about 40 wt % to about 75 wt %, from about 40 wt % to about 70 wt %, from about 40 wt % to about 65 wt %, from about 40 wt % to 60 wt %, from about 40 wt % to 55 wt %, from about 40 wt % to 50 wt %, from about 40 wt % to 45 wt %, from about 45 wt % to about 80 wt %, from about 50 wt % to about 80 wt %, from about 55 wt % to about 80 wt %, from about 60 wt % to about 80 wt %, from about 65 wt % to about 80 wt %, from about 70 wt % to about 80 wt %, from about 75 wt % to about 80 wt %, from about 45 wt % to about 75 wt %, from about 50 wt % to about 70 wt %, or from about 55 wt % to about 65 wt %, based on the total weight of the push layer. In certain embodiments, the POLYOX® is present in an amount of about 45 wt %, about 50 wt %, about 55 wt %, about 60 wt %, about 65 wt %, about 70 wt %, about 75 wt %, about 80 wt %, or any intermediate values therein, based on the total weight of the push layer.

In certain embodiments, the amount and grade of the POLYOX® present in the push layer affects the release profile of the drug from the dosage form, i.e., an increase in the molecular weight or amount of POLYOX® in the push layer will increase the force exerted on the pull layer for fast and complete drug recovery. In certain embodiments, the grade of POLYOX® is selected to provide desired lag time, release rate, and complete drug recovery in about 22 hours from the time of administration of the dosage form.

In certain embodiments, the push layer comprises at least one osmogen. In certain embodiments, the presence of osmogen in the push layer is essential for uniform swelling of the tablet core. In certain embodiments, the osmogen provides a concentration gradient for osmotic flow of liquid into the composition. The rate at which the polyethylene oxide polymer in the push layer absorbs water depends on the osmotic pressure generated by the osmogen present in the push layer, and the permeability of the semipermeable membrane/functional coat. As the polyethylene oxide polymer present in the push layer absorbs water, it expands in volume, which pushes the drug solution or suspension in the pull layer out of the tablet through the orifice/hole in the membrane. The compositions release drug at a rate, which is independent of pH and hydrodynamics of the dissolution medium.

In certain embodiments, the osmogen is an ionic compound comprising, but not limited to, sodium chloride, potassium chloride, potassium sulfate, lithium sulfate, sodium sulfate, lactose-sucrose, lactose-dextrose, mannitol-dextrose, mannitol-lactose, lactose-fructose, dextrose-fructose, sucrose, dextrose, mannitol, sorbitol, xylitol, dibasic sodium phosphate, and combinations thereof. In certain embodiments, the osmogen is sodium chloride. In certain embodiments, the osmogen is present in an amount of about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, from about 10 wt % to about 30 wt %, from about 15 wt % to about 30 wt %, from about 20 wt % to about 30 wt %, from about 25 wt % to about 30 wt %, or from about 10 wt % to about 25 wt %, or from about 15 wt % to about 20 wt %, based on the total weight of the push layer. In certain embodiments, the osmogen is present in an amount of about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, or any intermediate values therein, based on the total weight of the push layer. In certain embodiments, the osmogen is present in an amount of from about 10 wt % to about 30 wt %, based on the total weight of the push layer.

In certain embodiments, the push layer includes at least one binder selected from the group consisting of, but not limited to, povidone (e.g., medium molecular weight KOLLIDON® 30 LP), hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide, polyethylene glycol, alginates, pegylated polyvinyl alcohol, and any combination thereof. In certain embodiments, the binder is povidone. In certain embodiments, the binders are present in an amount of about 0.5 wt % to about 30 wt %, from about 0.5 wt % to about 29 wt %, from about 0.5 wt % to about 28 wt %, from about 0.5 wt % to about 27 wt %, from about 0.5 wt % to about 26 wt %, from about 0.5 wt % to about 25 wt %, from about 0.5 wt % to about 24 wt %, from about 0.5 wt % to about 23 wt %, from about 0.4 wt % to about 22 wt %, from about 0.5 wt % to about 21 wt %, from about 0.5 wt % to about 20 wt %, from about 0.5 wt % to about 19 wt %, from about 0.5 wt % to about 18 wt %, from about 0.5 wt % to about 17 wt %, from about 0.5 wt % to about 16 wt %, from about 0.5 wt % to about 15 wt %, from about 0.5 wt % to about 14 wt %, from about 0.5 wt % to about 13 wt %, from about 0.5 wt % to about 12 wt %, from about 0.5 wt % to about 11 wt %, from about 0.5 wt % to about 10 wt %, from about 0.5 wt % to about 9 wt %, from about 0.5 wt % to about 8 wt %, from about 0.5 wt % to about 7 wt %, from about 0.5 wt % to about 6 wt %, from about 0.5 wt % to about 5 wt %, from about 0.5 wt % to about 4 wt %, from about 0.5 wt % to about 3 wt %, from about 0.5 wt % to about 2 wt %, from about 0.5 wt % to about 1 wt %, from about 1 wt % to about 20 wt %, from about 2 wt %, to about 20 wt %, from about 3 wt % to about 20 wt %, from about 4 wt % to about 20 wt %, from about 5 wt % to about 20 wt %, from about 6 wt % to about 20 wt %, from about 7 wt % to about 20 wt %, from about 8 wt % to about 20 wt %, from about 9 wt % to about 20 wt %, from about 10 wt % to about 20 wt %, from about 11 wt % to about 20 wt %, from about 12 wt % to about 20 wt %, from about 13 wt % to about 20 wt %, from about 14 wt % to about 20 wt %, from about 15 wt % to about 20 wt %, from about 16 wt % to about 20 wt %, from about 17 wt % to about 20 wt %, from about 18 wt % to about 20 wt %, from about 19 wt % to about 20 wt %, from about 5 wt % to about 15 wt %, from about 5 wt % to about 10 wt %, or from about 10 wt % to about 15 wt %, based on the total weight of the push layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 25 wt %, about 26 wt %, about 27 wt %, about 28 wt %, about 29 wt %, about 30 wt %, or any intermediates values therein, based on the total weight of the push layer.

In certain embodiments, the push layer includes at least one stabilizer to prevent/reduce degradation of POLYOX®. In certain embodiments, the stabilizer comprises, but is not limited to, ascorbic acid, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the stabilizer is BHT. In certain embodiments, the stabilizer is present in an amount of about 0.01 wt % to about 0.5 wt %, from about 0.1 wt % to about 0.5 wt %, from about 0.2 wt % to about 0.5 wt %, from about 0.3 wt % to about 0.5 wt %, from about 0.4 wt % to about 0.5 wt %, from about 0.01 wt % to about 0.4 wt %, from about 0.01 wt % to about 0.3 wt %, from about 0.01 wt % to about 0.2 wt %, from about 0.01 wt % to about 0.1 wt %, or from about 0.05% to about 0.3 wt %, based on the total weight of the push layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, based on the total weight of the push layer.

In certain embodiments, the push layer includes lubricants comprising, but not limited to, magnesium stearate, glyceryl monostearates, palmitic acid, talc, carnauba wax, calcium stearate sodium, sodium or magnesium lauryl sulfate, calcium soaps, zinc stearate, polyethylene oxide, polyethylene glycols, polyoxyethylene monostearates, calcium silicate, silicon dioxide, hydrogenated vegetable oils and fats, stearic acid, or any combination thereof. In certain embodiments, the lubricant is present in an amount of about 0.1 wt % to about 2 wt %, from about 0.1 wt % to about 1.5 wt %, from about 0.1 wt % to about 1.0 wt %, from about 0.1 wt % to about 0.5 wt %, from about 0.5 wt % to about 2 wt %, from about 1.0 wt % to about 2.0 wt %, from about 1.5 wt % to about 2.0 wt %, or from about 1.0 wt % to about 1.5 wt %, based on the total weight of the push layer. In certain embodiments, the lubricant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the push layer.

In certain embodiments, the push layer includes at least one glidant comprising, but not limited to, talc, colloidal silicon dioxide, magnesium trisilicate, powdered cellulose, starch, and tribasic calcium phosphate. In certain embodiments, the glidant is colloidal silicon dioxide. In certain embodiments, the glidant is present in an amount of about 0.05 wt % to about 5 wt %, from about 0.1 wt % to about 1.5 wt %, from about 0.1 wt % to about 1.0 wt %, from about 0.1 wt % to about 0.5 wt %, from about 0.5 wt % to about 2 wt %, from about 1.0 wt % to about 2.0 wt %, from about 1.5 wt % to about 2.0 wt %, or from about 1.0 wt % to about 1.5 wt %, based on the total weight of the push layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, based on the total weight of the push layer.

In certain embodiments, the push layer includes at least one color pigment for identifying the push layer in the multilayer tablet core. In certain embodiments, the push layer and the placebo layer include the same color pigment. In certain embodiments, the placebo layer contains less amount of color pigment than the push layer. In certain embodiments, the push layer is darker in color than the placebo layer, which helps in identifying the placebo layer side while drilling a orifice in the membrane on the placebo layer side of the multilayer core. In certain embodiments, the push layer includes at least one pigment comprising iron oxide or lake-based colors. In certain embodiments, the pigment is a lake-based color. In certain embodiments, the pigment is an iron oxide pigment, e.g., oxide pigment red, and oxide pigment black. In certain embodiments, the pigment is present in an amount of about 0.5 wt % to about 2 wt % of the push layer.

In certain embodiments, the amount of push layer, based on the total weight of the uncoated core, can be between about 10 wt % and about 60 wt %, between about 20 wt % and about 55 wt %, between about 25 wt % and about 50 wt %, or between about 30 wt % and about 40 wt %.

Semipermeable Membrane

In certain embodiments, the trilayer tablet core is coated with a semipermeable membrane. In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the orifice into the core, and not too small to build hydrostatic pressure within the core.

In certain embodiments, the orifice is made via manual or laser drilling. In certain embodiments, the optimum orifice diameter is less than about 2.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

In certain embodiments, the coating composition and/or coating weight gain of the semipermeable membrane determines the lag time provided by the composition. In certain embodiments, the coating weight gain of the semipermeable membrane ranges from about 1 wt % to about 50 wt %, from about 5 wt % to about 45 wt %, from about 5 wt % to about 40 wt %, from about 5 wt % to about 35 wt %, from about 5 wt % to about 30 wt %, from about 5 wt % to about 25 wt %, from about 5 wt % to about 20 wt %, from about 5 wt % to about 15 wt %, from about 5 wt % to about 10 wt %, or any intermediate ranges therein, based on the total weight of the uncoated tablet core weight. In certain embodiments, the coating weight gain is about 10 wt %, about 12.5 wt %, or about 15 wt %, based on the total weight of the uncoated tablet core.

In certain embodiments, the semipermeable membrane coat over the multilayered tablet core is substantially impermeable to drugs and excipients present in the programmable osmotic-controlled oral composition. In certain embodiments, the semipermeable membrane is permeable to solvents, e.g., water, GI fluid, and simulated GI fluid. In certain embodiments, the semipermeable membrane doesn't react with gastric fluid regardless of the pH. In certain embodiments, the semipermeable membrane maintains the integrity of the composition to provide constant osmotic pressure during drug delivery. In certain embodiments, the semipermeable membrane comprises one or more pH-independent water-insoluble polymers that are permeable to water and substantially impermeable to solutes, e.g., drugs and excipients. Polymers suitable for inclusion in the semipermeable membrane comprise cellulose esters, e.g., cellulose acetate, cellulose diacetate, cellulose triacetate, cellulose propionate, cellulose acetate butyrate, and combinations thereof. In certain embodiments, the semipermeable membrane comprises cellulose acetate. In certain embodiments, the permeability of the semipermeable membrane can be enhanced by increasing the acetyl content in cellulose acetate. In certain embodiments, the semipermeable membrane comprises cellulose acetate with at least about 30% acetyl content. In certain embodiments, the semipermeable membrane comprises cellulose acetate with about 32% acetyl content, about 35% acetyl content, about 38% acetyl content, about 39% acetyl content, or about 39.8% acetyl content. In certain embodiments, permeability of the semipermeable membrane is enhanced by addition of water-soluble pore formers to the membrane composition. In certain embodiments, the water-soluble pore formers comprise, but are not limited to, of polyethylene glycol (PEG 400, PEG 1000, PEG 1450, PEG 3350), hydroxypropyl cellulose, polyvinyl pyrolidone (PVP), KOLLIDON® 30, KOLLICOAT® IR, sucrose, glucose, fructose, lactose, mannose, mannitol, sorbitol, methyl cellulose (METHOCEL™ E3, METHOCEL™ E5, METHOCEL™ E6), poloxamers, e.g., poloxamer 188, triethyl citrate, triacetin, hydroxypropyl methylcellulose, polyhydric alcohols such as glycerol, and combinations thereof. In certain embodiments, the semipermeable membrane comprises cellulose acetate and a pore former comprising polyethylene glycol. In certain embodiments, the water-insoluble polymer is cellulose acetate and the pore former is polyethylene glycol 3350. In certain embodiments, weight ratio of cellulose acetate to polyethylene glycol is between about 80:20 and about 99.5:0.5. In certain embodiments, the ratio of cellulose acetate to poloxamer is between about 80:20 and about 99.5:0.5. In certain embodiments, weight ratio of cellulose acetate and pore former affects variability in lag time. In certain embodiments, variability in lag time decreases with increasing the amount of pore former in the membrane. In certain embodiments, lag time decreases with increasing the amount of pore former in the membrane. In certain embodiments, the weight ratio of cellulose acetate and pore former is optimized to obtain a desired lag time with minimal variability. In certain embodiments, the weight ratio of cellulose acetate and pore former is about 80:20, about 85:15, about 90:10, about 95:5, about 96:4, about 97:3, about 98:2, about 99:1, about 99.5:0.5, or any intermediate values therein.

In certain embodiments, the semipermeable membranes include one or more plasticizers. Plasticizers play a significant role in adjusting flexibility and permeability of the semipermeable membrane. Plasticizers change the viscoelastic behavior and permeability of the polymer present in the semipermeable membrane. Plasticizers can convert a hard and brittle polymer into a softer and more pliable material that has more mechanical strength. Plasticizers used in the semipermeable membranes comprise polyethylene glycols, triethyl citrate, triacetin, diethyl tartrate, dibutyl sebacate, and combinations thereof. In certain embodiments, coating solvents used for coating comprise, but are not limited to, methylene chloride, carbon tetra chloride, acetone, methanol, ethanol, water, and/or any mixtures thereof. In certain embodiments, the coating solvent is a mixture of acetone and water. In certain embodiments, the acetone:water weight ratio is between 80:20 and 95:5. In certain embodiments, the acetone:water weight ratio is about 80:20, about 85:15, about 90:10, about 95:5, or any intermediate values therein.

In certain embodiments, the programmable osmotic-controlled oral compositions of the disclosure include an aesthetic coat over the semipermeable membrane. In certain embodiments, the aesthetic coat comprises colors, flavors, and sweeteners. In certain embodiments, the aesthetic coat is the outermost coat comprising OPADRY® II for pigmentation or OPADRY® clear for final glossiness. In certain embodiments, the aesthetic coat further comprises wax to improve flow for packaging.

Active Pharmaceutical Agents

In certain embodiments, the programmable osmotic-controlled oral compositions of the disclosure are suitable for drugs/active pharmaceutical agents comprising any level of aqueous solubilities.

In certain embodiments, drugs suitable for the programmable osmotic-controlled composition of the disclosure include CNS-acting drugs, cardiovascular-acting drugs, anti-infectives, analgesics, anesthetics, antiarthritics, antiasthmatics, anticonvulsants, antidepressants, antidiabetics, antidiarrheals, antihistamines, anti-inflammatories, antimigraines, antineoplastics, antiparkinson drugs, antipruritics, antipsychotics, antipyretics, antispasmodics, anticholinergics, sympathomimetics, calcium channel blockers, beta blockers, antiarrhythmics, antihypertensives, ACE inhibitors, diuretics, vasodilators, decongestants, hormones, hypnotics, immunosuppresives, parasympathomimetics, prostaglandins, proteins, peptides, sedatives and tranquilizers.

In certain embodiments, drugs suitable for delayed release include amphetamines, methylphenidate, diltiazem, carbamazepine, metoprolol, oxprenolol, nifedipine, albuterol, phenylpropanolamine, pseudoephedrine, chlorpheniramine maleate, prazosin, doxazosin, verapamil, oxybutynin chloride, isradipine, hydromorphone, paliperidone, modafinil, armodafinil, liothyronine, oseltamivir (Tamiflu), rifamycin, and glipzide.

In certain embodiments, compositions of the disclosure provide chrono drug release and are designed to treat, e.g., diseases in which biological rhythm(s) play a vital role in the pathophysiology of such diseases to avoid degradation of bioactive agents. In certain embodiments, the compositions of the disclosure are used to treat conditions that require chrono drug release, e.g., attention disorders, asthma, arthritis, congestive heart failure, myocardial infarction, stroke, cancer, peptic ulcer, epilepsy, migraine, pain, etc., wherein the risk and symptoms of the disease vary predictably over time.

In certain embodiments, chrono release compositions of the disclosure include antibiotics such as gentamycin, tobramycin, and amikacin; antihypertensives such as nifedipine, oral nitrates, propranolol, and atenolol; antiepileptic drugs such as valproic acid; anti-inflammatory drugs such as indomethacin and ketoprofen; anti-asthmatic drugs such as theophylline and beta sympathomimetics; anti-ulcer drugs such as ranitidine, cimetidine, and famotidine; anticancer drugs; NSAIDs for treating arthritis; antihyperlipidemic drugs, such as statins; opioid analgesics such as tramadol;

antimigraine drugs such as sumatriptan; immunosuppressants such as cyclosporine; local anesthetics such as lidocaine, ropivacaine, mepivacaine, and betoxycaine; and general anesthetics such as barbiturates.

In certain embodiments, immediate release sedatives suitable for the programmable osmotic-controlled compositions of the disclosure include clonidine, diphenhydramine, guanfacine, and/or melatonin.

6.3. Embodiments of the Dosage Form

In certain embodiments, additional programmable osmotic-controlled compositions containing additional pull layers, IR coatings, etc. are contemplated. A nonlimiting set of exemplary osmotic-controlled compositions follows.

In certain embodiments, the programmable osmotic-controlled compositions of the disclosure provide delayed extended release of a drug. In certain embodiments, the programmable osmotic-controlled compositions of the disclosure comprise a multilayer tablet core coated with a semipermeable membrane containing at least one orifice. In certain embodiments, the tablet core comprises multiple layers in the following order: a placebo layer facing the at least one orifice present in the semipermeable membrane, a delayed extended release layer containing a drug for delayed extended release, and a push layer, wherein the push layer is away (e.g., furthest away) from the orifice in the semipermeable membrane. In certain embodiments, the number of orifices in the semipermeable membrane can be two, three, or four. In certain embodiments, the optimum orifice diameter is about 0.6 mm, about 0.7 mm, about 0.8 mm, about 0.9 mm, about 1.0 mm, about 1.1 mm, or about 1.2 mm. In certain embodiments, the semipermeable membrane facing the top of the placebo layer is completely removed to provide an orifice comprising an optimum diameter that is equivalent to the diameter of the top of the placebo layer end of the multilayer core.

In certain embodiments, the programmable osmotic-controlled composition of the disclosure comprises a combination composition providing an immediate release of a drug, e.g., sedative and a delayed extended release of a different drug, e.g., a stimulant. In certain embodiments, the programmable osmotic-controlled composition of the disclosure comprises a multilayer tablet core coated with a semipermeable membrane containing at least one an orifice, and a coating of a sedative for immediate release, over the semipermeable membrane. In certain embodiments, the tablet core comprises multiple layers in the following order: a placebo layer in facing the orifice in the semipermeable membrane, a delayed extended release layer containing a stimulant, and a push layer, wherein the push layer is away (e.g., furthest away) from the orifice in the semipermeable membrane.

In certain embodiments, the programmable osmotic-controlled composition of the disclosure is a combination composition providing an extended release of a drug, e.g., a sedative and a delayed extended release of a different drug, e.g., a stimulant. In certain embodiments, the programmable osmotic-controlled composition of the disclosure comprises an IR coat containing a sedative, a seal coat below the IR sedative coat, an ER coat containing a sedative and below the seal coat, a cellulose acetate coat containing an orifice below the ER sedative coat, a "placebo" layer facing the orifice, a delayed extended release layer containing a stimulant and placed below the placebo layer, and a push layer placed below the delayed extended release layer and facing away from the orifice.

In certain embodiments, the programmable osmotic-controlled composition of the disclosure comprises a combination composition providing immediate release of a drug, e.g., a sedative and a chrono release of a different drug, e.g., a stimulant. In certain embodiments, the composition comprises a multilayer tablet core coated with a semipermeable membrane containing an orifice, and a coating of a drug for immediate release over the semipermeable membrane. In certain embodiments, the multilayered tablet core comprises a push layer, and a pull layer comprising a placebo layer and an active layer containing a stimulant, wherein the active layer comprises an immediate release layer and an extended release layer for providing chrono release of the stimulant. In certain embodiments, the tablet core comprises multiple layers in the following order: a placebo layer facing the orifice in the semipermeable membrane, a delayed immediate release layer containing a stimulant, a delayed extended release layer containing a stimulant, and a push layer, wherein the push layer is furthest away from the orifice in the semipermeable membrane. In certain embodiments, the delayed immediate release layer and the delayed extended release layer contain the same stimulant.

In certain embodiments, the programmable osmotic-controlled composition of the disclosure comprises a combination composition providing an immediate release of a drug, e.g., a sedative and a delayed chrono release of a different drug, e.g., a stimulant, wherein the immediate release sedative is present as an immediate release layer in the tablet core. In certain embodiments, the tablet core comprises multiple layers in the following order: an immediate release layer containing a sedative and facing the orifice in the semipermeable membrane, a placebo layer, a delayed immediate release layer, containing a stimulant, a delayed extended release layer containing a stimulant, and a push layer facing away from the orifice. In certain embodiments, the delayed immediate release layer and the delayed extended release layer contain the same stimulant.

In certain embodiments, the programmable osmotic-controlled composition of the disclosure provides pulsatile release of a drug. In certain embodiments, the composition comprises a multilayer tablet core coated with an IR coat comprising a drug, and a coating of a semipermeable membrane containing an orifice below the IR coat. In certain embodiments, the tablet core comprises multiple layers in the following order: a placebo layer facing the orifice in the semipermeable membrane, a delayed immediate release layer comprising the drug, and a push layer, to provide pulsatile release of a drug in two pulses. In certain embodiments, the tablet core comprises a first placebo layer facing the orifice in the semipermeable membrane, a first delayed immediate release layer comprising a stimulant, a second placebo layer, a second delayed immediate release layer, and a push layer, to provide a pulsatile release of a drug in three pulses.

In certain embodiments, the programmable osmotic-controlled composition of the disclosure comprises a combination composition providing an immediate release of a drug, e.g., a sedative and a delayed increasing (gradient) release of a different drug, e.g., a stimulant. In certain embodiments, the composition comprises a multilayer tablet core coated with a semipermeable membrane containing an orifice. In certain embodiments, the tablet core comprises multiple layers in the following order: a placebo layer facing the orifice in the semipermeable membrane, at least two delayed release layers comprising a stimulant for delayed release, and a push layer, wherein the at least two delayed release layers release the stimulant over a period of at least two successive intervals, wherein more stimulant is released in the second interval compared to the first interval.

In certain embodiments, the programmable osmotic-controlled compositions of the disclosure comprise a multilayer tablet core coated with a semipermeable membrane containing at least one orifice. In certain embodiments, the tablet core comprises multiple layers in the following order: a placebo layer facing at least one orifice present in the semipermeable membrane, a delayed release layer containing a drug, and a push layer, wherein the push layer is away (e.g., furthest away) from the orifice in the semipermeable membrane. In certain embodiments, the number of orifices in the semipermeable membrane can be two, three, or four. In certain embodiments, the optimum orifice diameter is about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, from about 0.6 mm to about 1.2 mm, from about 0.6 mm to about 1.1 mm, from about 0.6 mm to about 1.0 mm, from about 0.6 mm to about 0.9 mm, from about 0.6 mm to about 0.8 mm, from about 0.7 mm to about 1.2 mm, from about 0.8 mm to about 1.2 mm, from about 0.9 mm to about 1.2 mm, from about 1.0 mm to about 1.2 mm, from about 1.1 mm to about 1.2 mm, from about 0.7 mm to about 1.1 mm, or from about 0.8 mm to about 1.0 mm. In certain embodiments, the semipermeable membrane facing the top of the placebo layer is completely removed to provide an orifice comprising an optimum diameter that is equivalent to the diameter of the top of the placebo layer end of the multilayer core.

In certain embodiments, the viscosity of the placebo layer, the active layer, and the push layer, and the drug to polymer ratio in the active layer determine the release rate of the drug as an immediate release portion or an extended release portion. In certain embodiments, an immediate release layer will comprise a higher drug to polymer ratio compared to an extended release layer containing the same drug and the polymer.

In certain embodiments, the dosage form of the disclosure comprises an immediate release coat and an extended release coat of the sedative, and the two coats are separated by a seal coat.

In certain embodiments, the seal coat comprises hydroxypropyl methyl cellulose (HPMC), hydroxypropyl cellulose, hydroxyethyl cellulose, or povidone. In certain embodiments, the seal coat is present in an amount of between about 1 wt % to about 20 wt %, about 5 wt % to about 20 wt %, or about 5 wt % to about 15 wt % of the tablet core weight without seal coat.

In certain embodiments, the exemplary clinical situation described herein involves treatment of ADHD/ADD with an immediate release sedative and delayed release stimulant therapy.

6.4. Features of the Dosage Form

The present disclosure provides programmable osmotic-controlled oral compositions that provide delayed controlled release of a drug, and can be programmed to release drug at a desired time and for a desired duration, e.g., at a rhythm that matches the requirements for treatment in a sleep/wake cycle, or at a rhythm that matches the human circadian rhythm of a condition's symptom and/or of the individual being treated in the application of the therapy, with complete drug recovery. The osmotic-controlled oral compositions of the disclosure can be programmed to control lag time during the delay period and release drug at a desired rate after the delay period. In certain embodiments, the osmotic-controlled oral compositions are programmed to provide a precise lag time of at least about 4, 5, 6, 7, 8, 9, 10, 11, 12 hours, or intermediate time periods within the range. In certain embodiments, the programmable osmotic-controlled oral compositions of the disclosure provide delayed extended release, delayed chrono release, delayed pulsatile release, and pulsatile release of drugs with various doses and solubilities, and can be programmed to release drug at a rate that matches the human circadian rhythm of a condition's symptom and/or of the individual being treated in the application of the therapy. The programmable osmotic-controlled oral compositions of the disclosure provide pH-independent drug release at an osmotically determined rate for an extended time period, even as the dosage form transits the GI tract and encounters variable hydrodynamic environments of the GI tract, as well as microenvironments with significantly different pH values. In certain embodiments, the programmable osmotic-controlled oral compositions of the disclosure provide delayed controlled release of a drug, with minimum variability in lag time in response to varying pH and hydrodynamic conditions of a dissolution medium or the human GI tract. In certain embodiments, the minimal variability in lag time comprises variability of not more than 30%, not more than 29%, not more than 28%, not more than 27%, not more than 26%, not more than 25%, not more than 24%, not more than 23%, not more than 22%, not more than 21%, not more than 20%, not more than 19%, not more than 18%, not more than 17%, not more than 16%, not more than 15%, not more than 14%, not more than 13%, not more than 12%, not more than 11%, not more than 10%, not more than 9%, not more than 8%, not more than 7%, not more than 6%, not more than 5%, not more than 4%, not more than 3%, not more than 2%, not more than 1%, or any intermediate values therein, with variations in pH, presence or absence of food, gastric motility, or viscosity of dissolution medium.

In certain embodiments, the programmable osmotic-controlled oral compositions of the disclosure provide an immediate release of a drug and delayed extended release of the same or a different drug. The programmable osmotic-controlled oral compositions of the disclosure can comprise a multilayer tablet core comprising a drug, wherein the core is coated with a semipermeable membrane comprising at least one orifice and, optionally, an immediate release drug layer coating/immediate release drug layer, comprising a drug for immediate release, over the semipermeable membrane. In certain embodiments, the immediate release drug layer coating includes therapeutically effective doses of two or more pharmaceutically active ingredients or pharmaceutically effective salts thereof. In certain embodiments, the multilayered tablet core comprises a push layer and a pull layer. In certain embodiments, the pull layer comprises a placebo layer and an active layer. In certain embodiments, the active layer comprises a drug for delayed extended release. In certain embodiments, the drug in the immediate release drug layer coating and the drug in the active layer are different. In certain embodiments, the delayed extended release is a delayed chrono release comprising a delayed immediate release and a delayed extended release. In certain embodiments, the placebo layer is facing the orifice.

In certain embodiments, the programmable osmotic-controlled oral compositions of the disclosure provide an immediate release of a sedative and delayed extended release of methylphenidate hydrochloride. In certain embodiments, the timing of administration of the composition (e.g., in the evening) is titrated to optimize the tolerability and efficacy of the dose, as seen during, e.g., the next morning and throughout the day. In certain embodiments, the osmotic-controlled oral compositions of the active agent (e.g., methylphenidate) are programmed to provide drug release as follows: a lag time of at least about, e.g., 6-8 hours, a controlled release comprising about 20% of drug release in about 1-4 hours after the lag time, and an extended release of the drug with about 100% drug recovery in about 10-15 hours after the lag time (or about 22 hours from the time of administration of the composition). In certain embodiments, the disclosure provides programmable osmotic-controlled oral compositions of, e.g., methylphenidate that can be programmed to limit the amount of methylphenidate in plasma to less than about 20% of the maximum concentration ($C_{max}$) during the lag time to avoid side effects, e.g., insomnia.

In certain embodiments, the disclosure provides programmable osmotic-controlled oral compositions providing pulsatile release of a drug. In certain embodiments, the programmable osmotic-controlled oral compositions of the disclosure comprise a multilayered tablet core comprising layers in the following order: a placebo layer facing the orifice in the semipermeable membrane, an active layer, a (second) placebo layer, an (second) active layer, and a push layer, wherein the push layer is away (e.g., furthest away) from the orifice in the semipermeable membrane. In certain embodiments, the pulsatile release comprises pulses of drug release separated by a well-defined lag time(s). In certain embodiments, the pulsatile release is a delayed pulsatile release.

In certain embodiments, the programmable osmotic-controlled oral compositions of the disclosure are programmed to obtain a desired lag time by adjusting the composition of the placebo layer and/or the push layer, e.g., the amount and/or molecular weight/grade of the polyethylene oxide polymer (e.g., POLYOX®) in the placebo layer and/or the push layer, the coating composition of the semipermeable membrane, and/or the coating level of the semipermeable membrane.

In certain embodiments, the amount and/or molecular weight of the POLYOX® in the placebo layer can affect lag time. In certain embodiments, the placebo layer provides a desired lag time by delaying the release of the active pharmaceutical ingredient/drug in the environment of use. In certain embodiments, the lag time depends upon the amount/volume of the placebo layer that must be displaced by the expanding push layer. In certain embodiments, the lag time depends upon the molecular weight/grade of the POLYOX® (e.g., POLYOX® grade) present in the placebo layer. In certain embodiments, the lag time increases with increasing the molecular weight/grade of the POLYOX® present in the placebo layer. In certain embodiments, the volume of the placebo layer depends upon the amount of POLYOX® present in the placebo layer. In certain embodiments, the average molecular weight of the POLYOX® present in the placebo layer affects lag time. FIG. 14 shows the effect of average molecular weight of the POLYOX® present in the placebo layer on lag time and drug recovery of Tablets 35, 36, and 37, placed in about 900 ml of about 0.01N HCl for up to 24 hours, using USP Apparatus II (Sinkers), at 50 rpm and 37° C. FIG. 14 demonstrates that Tablet 35 containing POLYOX® 205 in the placebo layer provides shorter lag time compared to Tablet 36 containing POLYOX® 1105 in the placebo layer. The figure further demonstrates that for Tablets with less coating weight gain (Tablet 35) provide shorter lag time compared with higher coating level (Tablet 36).

In certain embodiments, the average molecular weight of the POLYOX® in the placebo layer should be at least about 300,000 Da to provide a lag time of at least about 6 hours. FIG. 23 shows the effect of POLYOX® grade in placebo layer on lag time of Tablets 44, 48, and 49, placed in about 900 ml of about 0.01N HCl for up to 24 hours, using USP Apparatus II (Sinkers), at 50 rpm and 37° C. Tablet 44 contains POLYOX® 1105 in the placebo layer; Tablet 48 contains POLYOX® N750 in the placebo layer; and Tablet 49 contains POLYOX® N80 in the placebo layer. The Figure demonstrates that the average molecular weight of POLYOX® in the placebo layer should be at least about 300K to provide a lag time of at least about 6 hours.

In certain embodiments, the lag time increases with increasing placebo layer amount and coating level. FIG. 18 shows effect of polymer amount in the placebo layer and coating weight gain/coating level on lag time of Tablets 43 and 44, containing a drug:polymer weight ratio of about 40:60, placed in about 900 ml of about 0.01N HCl for up to 24 hours, using USP Apparatus II (Sinkers), at 50 rpm and 37° C. Percentage drug dissolved is plotted over time (hours). The Figure demonstrates that higher placebo layer amounts and higher coating level on tablet increases lag time.

In certain embodiments, the placebo layer amount does not affect lag time. FIG. 7 shows the effect of the amount of placebo layer amount on dissolution profile of Tablets 20 and 21, placed in about 900 ml of about 0.01N HCl, using USP II (sinkers) at about 50 rpm and about 37° C. FIG. 7 demonstrates that compositions containing POLYOX® 1105 in the placebo layer exhibit higher dissolution rate and higher drug recovery, without affecting lag time, with increasing placebo layer amount.

In certain embodiments, the presence of osmogen in placebo layer has negligible effect on lag time and release rate. FIG. 22 shows effect of sodium chloride in placebo layer on lag time of Tablets 44, 46, and 47, placed in about 900 ml of about 0.01N HCl of tablets for up to 24 hours, using USP Apparatus II (Sinkers), at 50 rpm and 37° C. Tablet 44 contains 0% sodium chloride, Tablet 46 contains about 5% sodium chloride, and Tablet 47 contains about 10% sodium chloride in the placebo layer, based on the total weight of the placebo layer. The Figure demonstrates that presence of sodium chloride in placebo layer has negligible effect on lag time and release rate.

In certain embodiments, the presence of a wicking agent and an osmogen in the placebo layer affects drug recovery. FIG. 25 shows the effect of the presence of a wicking agent and an osmogen in the placebo layer on lag time of Tablets 52 and 53, placed in about 900 ml of about 0.01N HCl, using USP Apparatus II (Sinkers), at 50 rpm and 37° C. The Figure demonstrates that addition of a wicking agent and sodium chloride in the placebo layer reduces the drug recovery without substantially affecting lag time.

In certain embodiments, the drug:polymer weight ratio in the active layer affects lag time. FIG. 9 shows the effect of drug:polymer weight ratio on lag time and drug recovery of Tablets 23 and 24, placed in about 900 ml of about 0.01N HCl for up to 24 hours, using USP Apparatus II (Sinkers), at 50 rpm and 37° C. The figure demonstrates that increasing drug:polymer weight ratio in the active layer reduces lag time. The figure further demonstrates that tablets with the drug to polymer weight ratio of about 30:70 provide higher drug recovery compared to tablets with drug to polymer weight ratio of about 20:80.

In certain embodiments, the presence of an osmogen in the active layer improves drug recovery. FIG. 10 shows the effect of presence of sodium chloride in the active layer on dissolution profile of Tablets 25 and 26, placed in about 900 ml of about 0.01N HCl using USP Apparatus II (Sinkers), at 50 rpm and 37° C. Tablet 25 contains sodium chloride in the active layer and Tablet 26 does not contain sodium chloride in the active layer. The figure demonstrates that Tablet 25 containing NaCl in the active layer exhibits higher drug recovery compared to Tablet 26 containing no amount of sodium chloride in the active layer. Further, FIG. 13 shows the effect of coating weight gain, and presence of sodium chloride in the active layer, on lag time and drug recovery of Tablets 32, 32A, 33, and 34, placed in about 900 ml of about 0.01N HCl for up to 24 hours, using USP Apparatus II (Sinkers), at 50 rpm and 37° C. The Figure demonstrates that the tablet with a higher coating level (Tablet 32A) exhibits reduced drug recovery and increased lag time compared to Tablet 32. The Figure further compares drug recovery between coated tablets at same coating weight gain, with and without sodium chloride in active layer. The Figure demonstrates that tablets containing sodium chloride in active layer exhibit improved drug recovery compared to tablets without sodium chloride in the active layer, both tablets at a same coating weight gain. The Figure further shows that a decrease in amount of POLYOX® 205 in placebo layer improves drug recovery.

In certain embodiments, the push layer amount affects lag time and drug recovery. FIG. 15 shows the effect of push layer amount on lag time of Tablets 38 and 39, placed in about 900 ml of about 0.01N HCl for up to 24 hours, using USP Apparatus II (Sinkers), at 50 rpm and 37° C. The Figure demonstrates that for tablets containing POLYOX® 205 in the placebo layer, the lag time decreases with increase in push layer amount from about 17 wt % to about 22 wt %, based on the total weight of the uncoated trilayer tablet.

In certain embodiments, presence of an osmogen in the push layer reduces lag time and improves release rate and drug recovery. FIG. 11 shows the effect of presence of sodium chloride in the push layer on dissolution profile of Tablets 24, 27, 28, and 29, placed in about 900 ml of about 0.01N HCl for up to 24 hours, using USP Apparatus II (Sinkers), at 50 rpm and 37° C. The figure demonstrates that the presence of sodium chloride in the push layer reduces lag time and improves release rate and drug recovery at 24 hours. The figure further demonstrates that increasing the amount of sodium chloride in the push layer reduces lag time.

In certain embodiments, the average molecular weight of the POLYOX® present in the push layer affects release rate and drug recovery. FIG. 24 shows the effect of POLYOX® grade/average molecular weight in push layer on release rate and drug recovery of Tablets 44, 50, and 51, placed in about 900 ml of about 0.01N HCl for up to 24 hours, using USP Apparatus II (Sinkers), at 50 rpm and 37° C. The figure compares release rate and drug recovery in compositions containing POLYOX® WSR 303 (7M), POLYOX® WSR 301 (3M), and POLYOX® WSR Coagulant (5M) in push layer. The figure demonstrates that compositions containing POLYOX® N750 in the placebo layer and POLYOX® WSR 301 in the push layer or compositions containing POLYOX® N80 in the placebo layer and POLYOX® WSR Coagulant in the push layer provide higher drug recovery, compared to compositions containing POLYOX® 1105 in the placebo layer and POLYOX® WSR 303 in the push layer.

In certain embodiments, the ratio of cellulose acetate and polyethylene glycol in the semipermeable membrane affects lag time and drug recovery. FIG. 12 shows the effect of CA to PEG ratio in the membrane on lag time and drug recovery of the Tablets 30 and 31, with 15% coating weight gain, placed in about 900 ml of about 0.01N HCl for up to 24 hours, using USP Apparatus II (Sinkers), at 50 rpm and 37° C. The Figure demonstrates that increasing amount of cellulose acetate in the membrane increases lag time and reduces drug recovery from the membrane coated tablets.

In certain embodiments, the lag time and release rate of the osmotic-controlled oral compositions of the disclosure does not substantially depend upon the pH of the dissolution medium. FIG. 16 shows effect of pH on lag time for Tablet 40 with a drug to polymer weight ratio of about 30:70. The figure compares lag time and dissolution profiles of Tablet 40 in about 900 ml of about 0.01N HCl, pH 4.5 acetate buffer, and pH 6.8 phosphate buffer, using USP II (sinkers) at 50 rpm and 37° C. The figure demonstrates that the tablets exhibit minimal variability in lag time with variations in pH of the dissolution medium. Similarly, FIG. 19 compares the dissolution profiles of Tablet 45 in about 0.01 N HCl, in a pH 4.5 acetate buffer, and in a pH 6.8 phosphate buffer, using USP II (sinkers) at 50 rpm and 37° C. The figure demonstrates that the tablets exhibit minimal variability in lag time with variations in pH of the dissolution medium.

In certain embodiments, the lag time does not change with the viscosity of the dissolution medium. FIG. 20 shows the effect of viscosity of the dissolution medium on lag time of Tablet 45, placed in dissolution mediums with different viscosities, e.g., with and without HPMC. The Figure demonstrates there is no substantial change in lag time with changing viscosity of the dissolution medium.

In certain embodiments, the lag time does not change with changing hydrodynamics of the dissolution medium. FIG. 21 shows the effect of changing hydrodynamics of the dissolution medium on lag time of Tablet 45, placed in about 900 ml of about 0.01N HCl for up to 24 hours, using USP Apparatus II (Sinkers), at 50 rpm and 37° C. Tablet 45 contains a drug:polymer weight ratio of about 40:60. The Figure demonstrates that there is no substantial change in lag time with changing hydrodynamics of the dissolution medium.

In certain embodiments, the size and number of orifices affects % relative standard deviation (% RSD) among tablets. Example 27/Table 27 provides % relative standard deviation (% RSD) for Tablet 54A containing a coating with one orifice with 0.6 mm diameter; Tablet 54B containing a coating with two orifices, each with 0.6 mm diameter; and Tablet 54C containing a coating with one orifice with 1.2 mm diameter. The table shows that Tablet 54B containing two orifices, each with 0.6 mm diameter; and Tablet 54C containing one orifice with 1.2 mm diameter show significantly reduced % RSD among a set of three tablets, compared to Tablet 54A containing one orifice with 0.6 mm diameter.

6.5. Methods of Treatment

In certain embodiments, the programmable osmotic-controlled compositions of the disclosure delay the release of a drug and/or release drug at a rhythm that matches the human circadian rhythm of a condition's symptoms and/or of the individual being treated in the application of the therapy to optimize therapeutic outcome and minimize side effects. In certain embodiments, the programmable osmotic-controlled compositions of the disclosure can be used for treating conditions that require release of drug following circadian rhythm of the conditions, e.g., central nervous system (CNS) disorders, asthma, arthritis, congestive heart failure, myocardial infarction, stroke, cancer, peptic ulcer, narcolepsy, epilepsy, migraine, pain, etc., wherein the risks and symptoms of the disease vary predictably over time. In certain embodiments, the composition can be administered at night (e.g., before bedtime, e.g., about 8.00 pm) and the drug release is delayed to provide a precise lag time for about 4 to about 10 hours or longer, followed by an extended release, pulsatile release, or a chrono drug release. In certain embodiments, the compositions of the disclosure exhibit minimal variability in the lag time.

In certain embodiments, the programmable osmotic-controlled compositions of the disclosure provide delayed release of a stimulant used for the treatment of ADHD/ADD. Treatment of ADHD/ADD with stimulants helps to improve symptoms of ADHD, as well as to improve self-esteem, cognition, and social and family interactions of the patient.

The most commonly prescribed medications for ADHD include mixed amphetamines and methylphenidate. These medications have calming and focusing effects on an individual suffering from ADHD. Mixed amphetamines suitable for use in the programmable osmotic-controlled compositions of the disclosure include dextroamphetamine, d,l amphetamines, and pharmaceutically acceptable salts thereof, for example a mixture of amphetamine aspartate, amphetamine sulfate, dextroamphetamine sulfate, and dextroamphetamine saccharate.

Methylphenidate is a CNS stimulant approved by the FDA in 1955 for hyperactivity. Methylphenidate can be prescribed in a racemic mixture of dextro and levo conformations or as a pure dextro isomer. The use of pharmaceutically acceptable salts of methylphenidate, such as methylphenidate hydrochloride, is also contemplated in the present disclosure.

In certain embodiments, the disclosure provides therapeutic compositions and methods for treatment of attention deficit disorder (ADD), attention deficit hyperactive disorder (ADHD), or other attention disorder conditions responsive to central nervous system (CNS) stimulants. In certain embodiments, the disclosure provides a method of treating attention disorders in children, comprising administering to a child in need thereof a programmable osmotic-controlled composition of the disclosure providing an immediate release of a sedative, and a delayed release of a CNS stimulant, e.g., methylphenidate. The immediate release of a therapeutic amount of sedative helps the child sleep during the night, and a delayed and extended release of a therapeutic amount of a CNS stimulant keeps the child alert throughout the active periods of the day, including when the child is waking up. In certain embodiments, the release of stimulant is delayed for at least about 6 hours followed by an extended release or a chrono release of the stimulant. In certain embodiments, the delayed release of the stimulant is delayed chrono release. In certain embodiments, the delayed chrono release is delayed immediate release and a delayed extended release of the stimulant. In certain embodiments, the sedative is clonidine, diphenhydramine, guanfacine, or melatonin. In certain embodiments, the CNS stimulant is methylphenidate hydrochloride. In certain embodiments, the composition is administered before the child goes to bed. In particular, for pediatric patients with ADHD/ADD, once daily doses of such osmotic-controlled oral compositions of the disclosure at bedtime providing an immediate release of a sedative, e.g., clonidine, guanfacine, diphenhydramine, melatonin, for promoting sedation during nighttime, followed by delayed extended release or chrono release of a CNS stimulant, e.g., methylphenidate, that starts working in the morning and lasts during the daytime, addresses problems of insomnia during night, while keeping the child alert and attentive during the day when the child is in school or engaged in activities. In certain embodiments, the release of the stimulant is delayed for at least about 4 hours, at least about 5 hours, at least about 6 hours, at least about 7 hours, at least about 8 hours, at least about 9 hours, at least about 10 hours, at least about 11 hours, at least about 12 hours, or any intermediate periods. The composition provides a suitable lag time such that the sedative is effective during the sleep time of the patient, and the stimulant is effective during the day.

In certain embodiments, the disclosure provides programmable osmotic-controlled methylphenidate compositions providing improved patient compliance and convenience. The compositions provide clinical benefits of delivering methylphenidate hydrochloride in a delayed and extended manner, independent of drug chemical properties, patient physiological factors, and food. In certain embodiments, the disclosed compositions provide a timed, prolonged therapeutic effect when taken once a day. The programmable osmotic-controlled methylphenidate compositions of the disclosure provide food-independent delayed release that can avoid early morning dosing of methylphenidate hydrochloride stimulant to children suffering from ADHD/ADD. The compositions can be administered, with or without food, at night, before bedtime, e.g., about 8:00 pm (although other dosing times are contemplated), and provide delayed controlled release of a stimulant, e.g., methylphenidate. In certain embodiments, the osmotic-controlled compositions of methylphenidate avoid insomnia by limiting residual amount of methylphenidate hydrochloride in plasma to less than about 20% of the maximum concentration ($C_{max}$) during the lag time (e.g., the daily lag time).

In certain embodiments, the disclosure provides programmable osmotic-controlled compositions for treating diseases or conditions comprising attention deficit disorder (ADD), attention deficit hyperactive disorder (ADHD), narcolepsy, excessive daytime sleepiness, adrenal insufficiency, major depressive disorder, bipolar disorder, bipolar depression, negative symptoms in schizophrenia, chronic fatigue, or a binge-eating disorder.

In certain embodiments, the disclosure provides programmable osmotic-controlled compositions to improve wakefulness in adult patients with excessive sleepiness associated with obstructive sleep apnea, narcolepsy, or shift work disorder. In certain embodiments, the disclosure provides programmable osmotic-controlled compositions comprising armodafinil. In certain embodiments, the armodafinil compositions are administered at night to provide delayed extended release of armodafinil throughout the day.

Typically, stimulant-based medications for ADHD/ADD are dosed two hours prior to beginning an early morning routine, with an onset of treatment effect usually about two hours after administration. Such medications require twice-daily administration and cause compliance issues. The compositions of the disclosure avoid the need of early morning dosing that requires an onset time of about two hours and improve the symptoms of a condition in the early morning and throughout the day. Early morning symptom control, including getting the children ready for school, is a major challenge for parents and caregivers of children suffering from ADHD/ADD. The programmable osmotic-controlled compositions of the disclosure provide a convenient method of administration in that a single dose can be taken (typically in the evening prior to going to bed, or at whatever time of the day one retires for an extended period of sleep) and the release of drug is delayed for at least about 4 hours, e.g., about 6-12 hours.

In certain embodiments, the programmable osmotic-controlled compositions of the disclosure provide delayed release, with precise lag time, of hydrocortisone for the treatment of endometriosis.

The present disclosure provides compositions that can improve the symptoms of a condition in the early morning and throughout the day, without the need for early morning dosing that requires an onset time of about two hours. The present disclosure provides programmable osmotic-controlled oral compositions comprising drugs that usually require early morning dosing. Such compositions address the long-felt need of providing food-independent delayed release that can avoid burdensome early morning dosing of drugs to the patients. The compositions of the disclosure provide a desired lag time that is independent of the presence or absence of food, type of food, pH, gastric emptying, gastric motility, and volume of fluid in the GI tract. The compositions can be administered, with or without food, at night, before bedtime (e.g., at about 8 pm), and provide delayed controlled release of the active agents.

In certain embodiments, the methylphenidate/mixed amphetamine compositions of the disclosure provide an immediate release of a sedative, e.g., clonidine, diphenhydramine, guanfacine or melatonin, and a delayed controlled release of a CNS stimulant, e.g., methylphenidate or mixed amphetamine salts. In certain embodiments, the compositions of the disclosure do not include any sedative. The compositions can be administered, with or without food, at night, before bedtime and provide a delayed release of the stimulant. In certain embodiments, the compositions of the disclosure provide minimal variability in lag time in various hydrodynamic conditions and pH (both conditions and regions) of the GI tract. In certain embodiments, the timing of administration is titrated to optimize the tolerability and efficacy the next morning and throughout the day. In certain embodiments, the compositions of the disclosure avoid insomnia by limiting the residual amount of methylphenidate in plasma to less than about 20 wt % of the maximum concentration ($C_{max}$) during the determined/planned lag time. In certain embodiments, the compositions of the disclosure limit the residual amount of methylphenidate in plasma to less than about 15 wt %, less than about 10 wt %, less than about 5 wt %, less than about 4 wt %, less than about 3 wt %, less than about 2 wt %, or less than about 1 wt % of the maximum concentration ($C_{max}$).

In certain embodiments, the disclosure provides programmable osmotic-controlled compositions providing delayed pulsatile release of a drug, e.g., osmotic-controlled pulsatile release compositions.

In certain embodiments, the osmotic-controlled pulsatile release compositions of the disclosure contain drugs that undergo rapid first-pass metabolism and/or require colonic drug delivery.

In certain embodiments, the compositions of the disclosure provide plasma peak concentration at an optimal time, based on circadian rhythm of a condition, and reduce the number of required doses per day by saturating the first-pass metabolism.

6.6. Methods of Manufacture

In certain embodiments, the pull layer and the push layer in the multilayer programmable osmotic-controlled compositions of the disclosure comprise granules made by wet granulation. In certain embodiments, wet granulation comprises mixing of intragranular ingredients into a pre-blend, addition of liquid to the pre-blend for wetting of the pre-blend and formation of granules, milling for deagglomeration of granules, and drying and screening of the resulting granules.

In certain embodiments, the placebo layer comprises a placebo layer blend comprising placebo layer granules and extragranular excipients. In certain embodiments, the placebo layer granules comprise a swellable hydrophilic polymer, a binder, an osmogen, a stabilizer, and a color pigment. In certain embodiments, granules further include a wicking agent. In certain embodiments, glidant and lubricant are present as extragranular excipients in the placebo layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 60:40 and about 99:1 by weight. In certain embodiments, granules are dried, milled, blended with extragranular excipients, and compressed into the placebo layer blend. In certain embodiments, the placebo layer is made by dry granulation/slugging. In certain embodiments, the placebo layer is made by direct compaction In certain embodiments, active layer blend comprises active layer granules and extragranular excipients. In certain embodiments, the active layer granules comprise an active agent, a swellable hydrophilic polymer, a binder, an osmogen, a stabilizer, and a color pigment. In certain embodiments, granules further include a surfactant and/or a wicking agent. In certain embodiments, glidant and lubricant are present as extragranular excipients in the active layer blend. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 60:40 and about 99:1 by weight. In certain embodiments, granules are dried, milled, blended with extragranular excipients, and compressed into the active layer blend. In certain embodiments, the placebo layer is made by dry granulation/slugging. In certain embodiments, the placebo layer is made by direct compaction.

In certain embodiments, the push layer blend comprises push layer granules and extragranular excipients. In certain embodiments, the push layer granules comprise a swellable hydrophilic polymer, a binder, an osmogen, a stabilizer, and a color pigment. In certain embodiments, the granulating solvent for making granules comprises alcoholic solvent comprising dehydrated alcohol. In certain embodiments, the granulation solvent comprises a hydroalcoholic solvent comprising dehydrated alcohol and deionized water in varying ratios. In certain embodiments, the granulation solvent is a hydroalcoholic solvent containing dehydrated alcohol:water ratio of between about 60:40 and about 99:1 by weight. In certain embodiments, granules are dried, milled, blended with extragranular excipients, and compressed into the push layer blend. In certain embodiments, the push layer is made by dry granulation/slugging. In certain embodiments, the push layer is made by direct compaction.

In certain embodiments, the placebo layer blend, the active layer blend, and the push layer blend are filled into a tablet dye and compressed into a trilayer tablet core. The resulting tablet core is coated with a semipermeable membrane coat followed by laser drilling of an orifice in the coating, and, optionally, coating of an immediate release drug layer/coat over the semipermeable membrane layer/coat. In certain embodiments, the semipermeable membrane coat includes a water-soluble pore former. In certain embodiments, the water-soluble pore former is a water-soluble plasticizer, e.g., PEG 400, PEG 1000, PEG 1450, PEG 3350. In certain embodiments, the immediate release layer is further coated with an over coat. In certain embodiments, there is a seal coat between the semipermeable membrane and the immediate release drug layer comprising drug for immediate release. In certain embodiments, coating solvents used for coating comprise, but are not limited to, methylene chloride, carbon tetra chloride, acetone, methanol, ethanol, water, and/or any mixtures thereof. In certain embodiments, the coating solvent is a mixture of acetone and water. In certain embodiments, the acetone:water weight ratio is between 80:20 and 95:5. In certain embodiments, the acetone:water weight ratio is about 80:20, about 85:15, about 90:10, about 95:5, or any intermediate values therein. In certain embodiments, the solvents used for coating the semipermeable membrane include a mixture of acetone and water, wherein the film porosity increases with increasing water content.

For water-sensitive drugs, wet granulation is performed using organic solvents including methylene chloride, ethanol, isopropyl alcohol, butyl alcohol, ethyl acetate, cyclohexane, and carbon tetrachloride. In certain embodiments, wet granulation can be low shear, high shear, or fluid bed granulation. In certain embodiments, the fluid bed granulation comprises top spray granulation or rotor granulation.

In certain embodiments, the programmable osmotic-controlled compositions of the disclosure comprising active drugs with low drug loading, good flow, and compressibility are made by dry granulation comprising roller compaction or slugging. In such embodiments, it is important to match particle size of the drug and the swellable hydrophilic polymer, e.g. POLYOX®. In certain embodiments, compositions containing water-sensitive active drugs are made by a dry granulation process.

In certain embodiments, the dry granulation process includes slugging. In certain embodiments, slugging comprises blending of active drug and excipients into a uniform blend, optional milling of the resulting blend to break down agglomerates and disperse the active drug, compacting the blend into large slugs, milling of the slugs into granules with desired particle size, and compressing the granules with extragranular excipients into tablets.

In certain embodiments, dry granulation includes roller compaction, wherein densification of dry powder comprising active drug and excipients into a compact is obtained by controlled feeding of the powder through a set of directly opposed counter rotating rollers.

In certain embodiments, the disclosure provides making a multilayered tablet core for providing delayed controlled release of a drug. The multilayered tablet core comprises a push layer and a pull layer. The pull layer comprises granules made by roller compaction or wet granulation, and the push layer comprises granules made by direct compaction/slugging. In certain embodiments, the push layer comprises granules made by wet granulation. In certain embodiments, the pull layer comprises an active layer and a placebo layer.

In certain embodiments, the trilayer tablet core is coated with a semipermeable membrane. In certain embodiments, the semipermeable membrane is a polymeric film coating containing at least one orifice/hole/delivery port for drug release. In certain embodiments, size of the orifice must be optimized to control drug release from the dosage form. The size of orifice should not be too large to allow solute diffusion from the orifice into the core, and not too small to build hydrostatic pressure within the core.

In certain embodiments, the orifice is made via manual or laser drilling. In certain embodiments, the optimum orifice diameter is less than about 2.0 mm. In certain embodiments, the optimum orifice diameter is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, or any intermediate values therein. In certain embodiments, the optimum orifice diameter is equivalent to the diameter of the top of placebo layer end of the tablet core coated with the semipermeable membrane. In certain embodiments, it is important that the semipermeable membrane is adequately perforated with an orifice without compromising the integrity of the tablet core.

In certain embodiments, the programmable osmotic-controlled compositions of the disclosure provide delayed extended release of drugs that are prone to degradation and often have stability and shelf-life problems. Addition of a stabilizing agent, e.g., a pH-adjusting agent, to the composition decreases undesired degradation and improves product stability. In certain embodiments, the stabilizing agent comprises succinic acid, potassium phosphate, sodium phosphate, fumaric acid, citric acid, tartaric acid, malic acid, hydrochloric acid, aspartic acid, glutamic acid, oxalic acid, lactic acid, malonic acid, glyceric acid, ascorbic acid, and any combination thereof.

7. EXAMPLES

The following examples illustrate the disclosure in a nonlimiting manner. Unless indicated to the contrary, the numerical parameters set forth herein can vary depending upon the desired properties sought to be obtained by the present disclosure.

Example 1: Preparation of Delayed Release Methylphenidate Tablet Compositions The present Example provides various formulations for delayed release methylphenidate tablets as outlined in Table 1 and Table 2. Six different tablets were prepared.

TABLE 1

Delayed Extended Release Methylphenidate HCl Tablets

| Composition | Tablet 1 mg/dose | Tablet 2 mg/dose | Tablet 3 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 54.00 | 54.00 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.00 |
| Polyethylene oxide (POLYOX ® N80) | 149.0 | 149.0 | 207.0 |
| Povidone (KOLLIDON ® 30 LP) | 7.00 | 7.00 | 8.00 |
| Succinic acid | 3.00 | 3.00 | 3.00 |
| Stearic acid | 0.75 | 0.75 | 0.90 |
| Butylated hydroxytoluene | 0.05 | 0.05 | 0.10 |
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red Pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |

TABLE 1-continued

Delayed Extended Release Methylphenidate HCl Tablets

| Composition | Tablet 1 mg/dose | Tablet 2 mg/dose | Tablet 3 mg/dose |
|---|---|---|---|
| Acetone* | NA | NA | NA |
| Purified water* | NA | NA | NA |
| Total Weight | 584.10 | 584.10 | 584.10 |

*Removed during process

TABLE 2

Delayed Extended Release Methylphenidate HCl Tablets

| Composition | Tablet 4 mg/dose | Tablet 5 mg/dose | Tablet 6 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 37.24 | 37.24 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.0 |
| Polyethylene oxide (POLYOX ® N80) | 216.0 | 216.0 | 270.0 |
| Povidone (KOLLIDON ® 30 LP) | 7.0 | 7.0 | 8.0 |
| Succinic acid | 3.0 | 3.0 | 3.0 |
| Stearic acid | 0.75 | 0.75 | 0.90 |
| Butylated hydroxytoluene | 0.05 | 0.05 | 0.10 |
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red Pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |
| Acetone* | NA | NA | NA |
| Purified water* | NA | NA | NA |
| Total Weight | 634.34 | 634.34 | 647.1 |

*Removed during process

Tablets 1, 2, 4, and 5 contained two active layers, whereas Tablet 3 and Tablet 6 contained only one active layer. Tablets 1 and 2, contained different POLYOX® grade in placebo layer compared to Tablets 4 and 5. The tablets were made according to the following manufacturing procedure.

Manufacturing Procedure:

Separate blends of placebo layer, active layer 1, active layer 2, and push layer were made as per Tablets 1-6, using the following manufacturing procedure.

1. Preparation of placebo blend: Povidone and BHT were added to dehydrated alcohol in a suitable stainless-steel container and mixed to obtain a clear solution; the resulting solution was sprayed onto polyethylene oxide taken in a high shear mixer; the resulting granules were dried at a temperature of about 40° C. in a forced air oven, and screened through screen #20; the resulting screened granules were taken in a V-blender containing succinic acid (pre-screened through screen #30) and mixed for 7 minutes at 25 RPM, followed by addition of stearic acid (prescreened through screen #30) and further mixing for about 3 minutes at 25 RPM.

2. Preparation of active layer 1 and active layer 2 blend: Povidone and BHT were added to dehydrated alcohol in a suitable stainless-steel container and mixed to obtain a clear solution; the resulting solution was sprayed onto a blend of methylphenidate HCl and polyethylene oxide taken in a high shear mixer; the resulting granules were dried at a temperature of about 40° C. in a forced air oven, and screened through screen #20; the resulting screened granules were taken in a V-blender containing succinic acid (prescreened through screen #30) and mixed for 7 minutes at 25 RPM, followed by addition of stearic acid (prescreened through screen #30) and further mixing for about 3 minutes at 25 RPM.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing stearic acid (prescreened through screen #30) and mixed for about 3 minutes at 25 RPM.

4. Required amount of each blend was filled into the die, in the order as per Tables 1 and 2, and then compressed into tetra-layer tablet compositions as outlined in Tables 1 and 2.

5. Cellulose acetate was added to a stainless-steel container charged with acetone and mixed to obtain a clear solution.

6. Polyethylene glycol 3350 was added to the solution from step #5, followed by the addition of water, and mixed for about 30 minutes.

7. The tablets from step #4 were taken in a coating pan and coated with the solution from step #6 until the target % weight gain is attained, and then cured at a product temperature of 40° C. for one hour.

8. A hole/orifice of about 0.3 mm is drilled into the coating, at the placebo layer end of the tablet.

Example 2: Preparation of Composition Providing Immediate Release of Clonidine and Delayed Extended Release of Methylphenidate HCl The present Example provides various formulations for delayed extended release methylphenidate HCL tablets that comprise clonidine HCl IR coating. The components of the clonidine HCl IR coating are provided in Table 3 below.

TABLE 3

Clonidine HCl IR coating

| Composition | Tablets 7-12 mg/dose |
|---|---|
| Clonidine HCl | 0.3 |
| Hypromellose (METHOCEL ™ E5 LV) | 2.5 |
| Talc | 0.5 |
| Ethanol* | NA |
| Purified water* | NA |

*Removed during process

The clonidine HCl IR coating is added to Tablets 1-6 of the Example 1 according to the procedure detailed below.

Manufacturing Procedure:

1. Hypromellose is added to ethanol taken in a stainless-steel container and mixed until it is uniformly dispersed. Purified water is slowly added and mixed until a clear solution is formed.

2. To the solution from step #1, clonidine HCl is added and mixed until dissolved.

3. Talc is added to the solution from step #2 and mixed until it is uniformly dispersed.

4. Methylphenidate HCl tablets (Tablets 1-6) are taken in a coating pan and coated with the dispersion from step #3.

Example 3: Preparation of Delayed Extended Release Mixed Amphetamine Tablet Compositions Comprising Two Active Layers The present Example provides three different delayed extended release mixed amphetamine tablet compositions. The components of the different tablets are outlined below in Table 4.

TABLE 4

Mixed Amphetamine Tablet Compositions

| Composition | Tablet 13 mg/dose | Tablet 14 mg/dose | Tablet 15 mg/dose |
|---|---|---|---|
| Placebo Layer | | | |
| Polyethylene oxide (POLYOX ® N80) | NA | 6.750 | NA |
| Polyethylene oxide (POLYOX ® 750) | 6.750 | NA | 6.750 |
| Povidone (KOLLIDON ® 30 LP) | 0.720 | 0.720 | 0.720 |
| Succinic acid | 0.270 | 0.270 | 0.270 |
| Stearic acid | 0.081 | 0.081 | 0.081 |
| Butylated hydroxytoluene | 0.009 | 0.009 | 0.009 |
| Active Layer 1 | | | |
| Mixed amphetamine salts (base equivalence) | 1.000 | 1.000 | NA |
| Polyethylene oxide (POLYOX ® N80) | 3.35 | 3.35 | NA |
| Povidone (KOLLIDON ® 30 LP) | 0.360 | 0.360 | NA |
| Succinic acid | 0.099 | 0.099 | NA |
| Stearic acid | 0.004 | 0.004 | NA |
| Butylated hydroxytoluene | 0.0045 | 0.0045 | NA |
| Active Layer 2 | | | |
| Total amphetamine base equivalence | 4.000 | 4.000 | 5.000 |
| Polyethylene oxide (POLYOX ® N80) | 19.44 | 19.44 | 24.3 |
| Povidone (KOLLIDON ® 30 LP) | 0.630 | 0.630 | 0.720 |
| Succinic acid | 0.270 | 0.270 | 0.270 |
| Stearic acid | 0.0675 | 0.0675 | 0.081 |
| Butylated hydroxytoluene | 0.0045 | 0.0045 | 0.009 |
| Push Layer | | | |
| Polyethylene oxide (POLYOX ® 303) | 12.150 | 12.150 | 12.150 |
| Povidone (KOLLIDON ® 30 LP) | 3.285 | 3.285 | 3.285 |
| Sodium Chloride | 0.823 | 0.823 | 0.823 |
| Stearic acid | 0.45 | 0.45 | 0.45 |
| Butylated hydroxytoluene | 0.0405 | 0.0405 | 0.0405 |
| Red Pigment blend | 0.162 | 0.162 | 0.162 |
| Functional Coating Layer | | | |
| Cellulose Acetate | 3.663 | 3.663 | 3.663 |
| Polyethylene Glycol 3350 | 0.036 | 0.036 | 0.036 |
| Acetone* | NA | NA | NA |
| Purified water* | NA | NA | NA |
| Total Weight | 57.67 | 57.67 | 58.819 |

*Removed during process

Tablets 13 and 15 contain POLYOX® 750 in the placebo layer; and Tablet 14 contain POLYOX® N80 in the placebo layer. Tablet 13 and Tablet 14 contain two active layers, and Tablet 15 contain one active layer. The tablets are made according to the following manufacturing procedure.

Manufacturing Procedure:

Tablets 13-15 comprise two active layers, Active layer 1 and Active layer 2, to provide delayed chrono drug release. Separate blends of placebo layer, active layer 1, active layer 2, and push layer are made as per Tablets 13-15.

Preparation of placebo blend: Povidone and BHT are added to dehydrated alcohol in a suitable stainless-steel container and mixed to obtain a clear solution; the resulting solution is sprayed onto polyethylene oxide taken in a high shear mixer; the resulting granules are dried at a temperature of about 40° C. in a forced air oven, and screened through screen #20; the resulting screened granules were taken in a V-blender containing succinic acid (prescreened through screen #30) and mixed for 7 minutes at 25 RPM, followed by addition of stearic acid (prescreened through screen #30) and further mixing for about 3 minutes at 25 RPM.

1. Preparation of active layer 1 and active layer 2 blend: Povidone and BHT are added to dehydrated alcohol in a suitable stainless-steel container and mixed to obtain a clear solution; the resulting solution is sprayed onto a blend of mixed amphetamine base, and polyethylene oxide taken in a high shear mixer; the resulting granules are dried at a temperature of about 40° C. in a forced air oven, and screened through screen #20; the resulting screened granules are taken in a V-blender containing succinic acid (prescreened through screen #30) and mixed for 7 minutes at 25 RPM, followed by addition of stearic acid (prescreened through screen #30) and further mixing for about 3 minutes at 25 RPM.

2. Preparation of push layer blend: Povidone and BHT are added to dehydrated alcohol in a suitable stainless-steel container and mixed to obtain a clear solution; the resulting solution is sprayed onto a blend of polyethylene oxide, sodium chloride, and red pigment blend taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

3. Required amount of each blend is filled into the die, in the order as per

Table 4, and then compressed as tetra-layer tablet compositions.

4. Cellulose acetate is added to a stainless-steel container charged with acetone and mixed to obtain a clear solution.

5. Polyethylene glycol 3350 is added to the solution from step #5, followed by the addition of water, and mixed for about 30 minutes.

6. The tablets from step #4 are taken in a coating pan and coated with the solution from step #6 until the target % weight gain is attained and then cured at a product temperature of 40° C. for one hour.

7. A hole/orifice of about 0.3 mm is drilled into the coating, at the placebo layer end of the tablet.

Example 4: Preparation of Pulsatile Release Composition Comprising Two Active Layers Separated by a Placebo Layer The present Example provides a formulation for pulsatile release methylphenidate HCl tablet. The components of the tablet are outlined below in Table 5.

TABLE 5

Pulsatile Release Methylphenidate HCl Tablet

| Composition | Tablet 16 mg/dose |
|---|---|
| Placebo Layer | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |
| Active Layer 1 | |
| Methylphenidate HCl | 27.00 |
| Polyethylene oxide (POLYOX ® N80) | 81.00 |
| Povidone (KOLLIDON ® 30 LP) | 4.00 |
| Stearic acid | 0.05 |
| Butylated hydroxytoluene | 0.05 |
| Placebo Layer | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |
| Active Layer 2 | |
| Methylphenidate HCl | 27.00 |
| Polyethylene oxide (POLYOX ® N80) | 81.0 |
| Povidone (KOLLIDON ® 30 LP) | 4.00 |
| Stearic acid | 0.05 |
| Butylated hydroxytoluene | 0.05 |
| Push Layer | |
| Polyethylene oxide (POLYOX ® 303) | 135.0 |
| Povidone (KOLLIDON ® 30 LP) | 36.50 |
| Sodium Chloride | 9.15 |
| Stearic acid | 0.45 |
| Butylated hydroxytoluene | 0.10 |
| Red Pigment blend | 1.80 |
| Functional Coating Layer | |
| Cellulose Acetate | 40.70 |
| Polyethylene Glycol 3350 | 0.40 |
| Acetone* | NA |
| Purified water* | NA |
| Total Weight | 616.30 |

*Removed during Process

Tablet 16 contains two placebo layers and two active layers disposed alternately. The composition further includes a push layer and a functional coating layer. Tablet 16 is made according to the procedure detailed below.

Manufacturing Procedure:

Separate blends of placebo layers, active layer 1, active layer 2, and push layer are made as per Tablet 16.

1. Preparation of placebo blend: Povidone and BHT are added to dehydrated alcohol in a suitable stainless-steel container and mixed to obtain a clear solution; the resulting solution is sprayed onto polyethylene oxide taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

2. Preparation of active layer 1 and active layer 2 blend: Povidone and BHT are added to dehydrated alcohol in a suitable stainless-steel container and mixed to obtain a clear solution; the resulting solution is sprayed onto a blend of methylphenidate HCL, and polyethylene oxide taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

3. Preparation of push layer blend: Povidone and BHT are added to dehydrated alcohol in a suitable stainless-steel container and mixed to obtain a clear solution; the resulting solution is sprayed onto a blend of polyethylene oxide, sodium chloride, and red pigment blend taken in a high shear mixer; the resulting granules are dried at a temperature of about 40° C. in a forced air oven, and screened through screen #20; the resulting screened granules are taken in a V-blender containing stearic acid (prescreened through screen #30) and mixed for about 3 minutes at 25 RPM.

4. Required amount of each blend is filled into the die, in the order as per Table 5, and then compressed into pentalayer tablet compositions.

5. Cellulose acetate is added to a stainless-steel container charged with acetone and mixed to obtain a clear solution.

6. Polyethylene glycol 3350 is added to the solution from step #5, followed by the addition of water, and mixed for about 30 minutes.

7. The tablets from step #4 are taken in a coating pan and coated with the solution from step #6 until the target % weight gain is attained and then cured at a product temperature of 40° C. for one hour.

8. A hole/orifice of about 0.3 mm is drilled into the coating, at the placebo layer end of the tablet.

Example 5 Clonidine HCl IR Coating

The present Example provides a formulation for pulsatile release methylphenidate HCl tablet that comprises clonidine HCl IR coating. The components of the clonidine HCl IR coating are provided in Table 6 below.

TABLE 6

Clonidine HCl IR Coating

| Composition | Tablet 17 mg/dose |
|---|---|
| Clonidine Hydrochloride | 0.3 |
| Hypromellose (METHOCEL E5LV) | 2.5 |
| Talc | 0.5 |
| Ethanol* | NA |
| Purified water* | NA |

*Removed during Process

The clonidine HCl IR coating is added to Tablet 16 of the Example 4 according to the procedure detailed below.

Manufacturing Procedure:

1. Hypromellose is added to ethanol taken in a stainless-steel container and mixed until it is uniformly dispersed. Purified water is slowly added and mixed until a clear solution is formed.
2. To the solution from step #1, clonidine hydrochloride is added and mixed until dissolved.
3. Talc is added to the solution from step #2 and mixed until it is uniformly dispersed.
4. The methylphenidate HCl tablets (Tablet 16) are taken in a coating pan and coated with the dispersion from step #3.

Example 6: Preparation of Delayed Extended Release Methylphenidate HCl Tablet Compositions Containing One Active Layer The present Example provides two different delayed extended release methylphenidate HCl tablet compositions. The components of the different tablets are outlined below in Table 7.

TABLE 7

Extended Release Methylphenidate HCl Tablet Compositions

| Composition | Tablet 18 mg/dose | Tablet 19 mg/dose |
|---|---|---|
| Placebo Layer | | |
| Polyethylene oxide (POLYOX ® WSR 1105) | 100.31 | 100.31 |
| Povidone (KOLLIDON ® 30 LP) | 5.22 | 5.22 |
| Stearic acid | 1.00 | 1.00 |
| Butylated hydroxytoluene | 0.13 | 0.13 |
| Red pigment blend | 0.07 | 0.07 |
| Cab-O-Sil ® (fumed silica) | 0.27 | 0.27 |
| Dehydrated alcohol* | q.s. | q.s. |
| Active Layer | | |
| Methylphenidate HCl | 54.00 | 54.00 |
| Polyethylene oxide (POLYOX ® N80) | 81.00 | 81.00 |
| Sodium chloride | 10.00 | 10.00 |
| Povidone (KOLLIDON ® 30 LP) | 7.60 | 7.60 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 88.00 | 88.00 |
| Sodium chloride | 22.00 | 22.00 |
| Povidone (KOLLIDON ® 30 LP) | 11.50 | 11.50 |
| Stearic acid | 0.50 | 0.50 |
| Butylated hydroxytoluene (BHT) | 0.20 | 0.20 |
| Red pigment blend | 1.50 | 1.50 |
| Cab-O-Sil ® | 0.30 | 0.30 |
| Dehydrated alcohol* | q.s. | q.s. |
| Total Core Weight | 384.6 | 384.6 |
| Functional Coating Layer | | |
| OPADRY ® CA clear (95:5) | 48.13 | 57.75 |
| Total Tablet Weight | 432.73 | 442.35 |

*Removed during process

Tablet 18 and Tablet 19 include different amounts of OPADRY® CA with CA:PEG ratio of about 95:5. The tablets were made according to the following manufacturing procedure.

Manufacturing Procedure

Separate blends of placebo layer, active layer, and push layer were made as per Tablets 18 and 19.

1. Preparation of placebo blend: Povidone and BHT were added to dehydrated alcohol in a suitable stainless-steel container and mixed to obtain a clear solution; the resulting solution was sprayed onto a blend of polyethylene oxide and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and mixing for 3 minutes.

2. Preparation of active layer blend: Povidone and BHT were added to dehydrated alcohol in a suitable stainless-steel container and mixed to obtain a clear solution; the resulting solution was sprayed onto a blend of methylphenidate HCl, polyethylene oxide and sodium chloride taken in a high shear mixer; the resulting granules were dried at a temperature of about 40° C. in a forced air oven, and screened through screen #20; the resulting screened granules are taken in a V-blender containing stearic acid (prescreened through screen #30) and mixed for about 3 minutes at 25 RPM.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

4. Required amount of each blend (as per Tablets 18 and 19) was filled into the die and then compressed as tri-layer tablet composition.

5. OPADRY® CA was added to a stainless-steel container charged with acetone and water (about 92:8) and mixed for not less than 60 minutes to obtain a clear solution.

6. The tablets from step #4 were taken in a coating pan and coated with the solution from step #5 until the target % weight gain was obtained and cured at a product temperature of 40° C. for one hour.

7. A hole/orifice of about 0.3 mm was drilled into the coating, at the placebo layer end of the tablet.

Example 7: Dissolution Profiles of Tablets Containing Different Amounts of POLYOX® WSR 1105 in the Placebo Layer The present Example provides two different delayed extended release methylphenidate HCl tablets with various amounts of POLYOX® WSR 1105 in the placebo layer. The components of the two tablets are outlined below in Table 8. 9.

TABLE 8

| Composition | Tablet 20 mg/dose | Tablet 21 mg/dose |
|---|---|---|
| Placebo Layer | | |
| Polyethylene oxide (POLYOX ® WSR 1105) | 150.0 | 75.0 |
| Povidone (KOLLIDON ® 30 LP) | 8.0 | 4.0 |
| Stearic acid | 1.6 | 0.8 |
| Butylated hydroxytoluene | 0.20 | 0.10 |
| Dehydrated alcohol* | q.s. | q.s. |

TABLE 8-continued

| Composition | Tablet 20 mg/dose | Tablet 21 mg/dose |
|---|---|---|
| Active Layer | | |
| Methylphenidate HCl | 54.0 | 54.0 |
| Polyethylene oxide (POLYOX® N80) | 135.0 | 135.0 |
| Povidone (KOLLIDON® 30 LP) | 4.0 | 4.0 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX® WSR 303) | 88.00 | 88.00 |
| Sodium chloride | 22.00 | 22.00 |
| Povidone (KOLLIDON® 30 LP) | 12.0 | 12.0 |
| Stearic acid | 0.50 | 0.50 |
| Butylated hydroxytoluene (BHT) | 0.20 | 0.20 |
| Red pigment | 1.50 | 1.50 |
| Dehydrated alcohol* | q.s. | q.s. |
| Total Core Weight | 478.0 | 398.1 |
| Functional Coating Layer | | |
| OPADRY® CA clear (95:5) | 71.7 | 59.7 |
| Total Weight | 549.7 | 457.8 |

*Removed during process

Tablet 20 contained 150 mg of POLYOX® WSR 1105 in the placebo layer; and Tablet 21 contained 75.0 mg of POLYOX® WSR 1105 in the placebo layer. Tablet 20 contained about 34 wt % of placebo layer, based on the total weight of the uncoated tablet core. Tablet 21 contained about 20 wt % of placebo layer, based on the total weight of the uncoated tablet core. Tablets 20 and 21 contained 15 wt % of coating, based on the total weight of the uncoated tablet core. Trilayer methylphenidate tablets were made according to the procedure as per Example 5.

Tablets 20 and 21 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 7 shows the effect of placebo layer amount on lag time and dissolution profile of the tablet. The figure demonstrates that tablets with higher amount of placebo layer exhibit higher dissolution rate and higher drug recovery compared to tablets with lesser amounts of placebo layer. The figure further demonstrates that the POLYOX® WSR 1105 amount in the placebo layer, and weight % of placebo layer, based on the total weight of the uncoated tablet core, does not affect lag time.

Example 8: Effect of Average Molecular Weight of POLYOX® Present in Placebo Layer on Lag Time, Release Rate, and Drug Recovery The present Example provides two delayed release methylphenidate tablets comprising different grades of POLYOX® in the placebo layer. The components of the two tablets are outlined below in Table 9.

TABLE 9

| Composition | Tablet 22 mg/dose | Tablet 20 mg/dose |
|---|---|---|
| Placebo Layer | | |
| Polyethylene oxide (POLYOX® 205) | 150.0 | — |
| Polyethylene oxide (POLYOX® 1105) | — | 150.0 |

TABLE 9-continued

| Composition | Tablet 22 mg/dose | Tablet 20 mg/dose |
|---|---|---|
| Povidone (KOLLIDON® 30 LP) | 8.0 | 8.0 |
| Stearic acid | 1.6 | 1.6 |
| Butylated hydroxytoluene | 0.20 | 0.10 |
| Dehydrated alcohol* | q.s. | q.s. |
| Active Layer | | |
| Methylphenidate HCl | 54.0 | 54.0 |
| Polyethylene oxide (POLYOX® N80) | 135.0 | 135.0 |
| Povidone (KOLLIDON® 30 LP) | 4.0 | 4.0 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX® WSR 303) | 88.00 | 88.00 |
| Sodium chloride | 22.00 | 22.00 |
| Povidone (KOLLIDON® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 478.0 | 478.0 |
| Functional Coating Layer | | |
| OPADRY® CA clear (95:5) | 71.7 | 71.7 |
| Total Weight | 549.7 | 549.7 |

*Removed during process

Trilayer methylphenidate tablets were made according to the procedure as per Example 5. Tablets 20 and 22 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 8 shows the effect of average molecular weight of the POLYOX®, present in the placebo layer, on dissolution rate of the tablet. The Figure demonstrates an improvement in dissolution rate and reduction in drug recovery, and no change in lag time, with increasing the average molecular weight of POLYOX®, present in the placebo layer, from about 600K (POLYOX® 205) to about 900K (POLYOX® 1105).

Example 9: Effect of Drug to Polymer Ratio in the Active Layer on Lag Time of the Dosage Form The present Example provides two delayed release methylphenidate tablets comprising active layers with varying drug to polymer ratios. The components of the two tablets are outlined below in Table 10.

TABLE 10

| Composition | Tablet 23 mg/dose | Tablet 24 mg/dose |
|---|---|---|
| Placebo Layer | | |
| Polyethylene oxide (POLYOX® WSR 1105) | 150.0 | 150.0 |
| Povidone (KOLLIDON® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |

TABLE 10-continued

| Composition | Tablet 23 mg/dose | Tablet 24 mg/dose |
|---|---|---|
| Active Layer | | |
| Methylphenidate HCl | 54.0 | 54.0 |
| Polyethylene oxide (POLYOX ® N80) | 207.0 (20:80) | 135.0 (28:72) |
| Povidone(KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 98.00 | 98.00 |
| Sodium chloride | 12.00 | 12.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total core Weight | 550.0 | 478.0 |
| Functional Coating Layer | | |
| OPADRY ® CA clear (95:5) | 82.5 | 71.7 |
| Total Weight | 632.5 | 549.7 |

*Removed during process

Trilayer methylphenidate tablets were made according to the procedure as per Example 5. Tablets 23 and 24 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 9 shows the effect of drug to polymer ratio in the active layer on lag time of the tablet. The figure demonstrates that increasing drug:polymer weight ratio in the active layer reduces lag time. Tablet 24 with drug to polymer weight ratio of about 30:70 provides a lag time of about 9 hours, Tablet 23 with a drug to polymer weight ratio of about 20:80 provides a lag time of about 10 hours. The figure further demonstrates that tablets with the drug to polymer weight ratio of about 30:70 provide higher drug recovery compared to tablets with drug to polymer weight ratio of about 20:80.

Example 10: Effect of Sodium Chloride Amount in the Active Layer on Drug Recovery The present Example provides two delayed release methylphenidate tablets. Tablet 25 contains sodium chloride in the active layer, whereas Tablet 26 does not. The components of the two tablets are outlined below in Table 11.

TABLE 11

| Composition | Tablet 25 mg/dose | Tablet 26 mg/dose |
|---|---|---|
| Placebo Layer | | |
| Polyethylene oxide (POLYOX ® WSR 1105) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 125.0 | 135.0 |
| Sodium chloride | 10.0 | — |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 98.00 | 98.00 |
| Sodium chloride | 22.00 | 22.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 488.0 | 488.0 |
| Functional Coating Layer | | |
| OPADRY ® CA clear (95:5) | 71.7 | 71.7 |
| Total Weight | 559.7 | 559.7 |

*Removed during process

Tablet 25 contained sodium chloride in the active layer; and Tablet 26 did not contain any amount of sodium chloride in the active layer. Trilayer methylphenidate tablets were made according to the procedure as per Example 5. Tablets 25 and 26 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 10 compares drug recovery from tablets with and without sodium chloride in active layer. The figure demonstrates that Tablet 25 containing NaCl in the active layer exhibits higher drug recovery compared to Tablet 26 containing no amount of sodium chloride in the active layer.

Example 11: Effect of Sodium Chloride Amount in the Push Layer on Drug Recovery

The present Example provides four delayed release methylphenidate tablets comprising various amounts of sodium chloride in the push layer. The components of the two tablets are outlined below in Table 12.

TABLE 12

| Composition | Tablet 24 mg/dose | Tablet 27 mg/dose | Tablet 28 mg/dose | Tablet 29 mg/dose |
|---|---|---|---|---|
| Placebo Layer | | | | |
| Polyethylene oxide (POLYOX ® WSR 1105) | 150.0 | 150.0 | 150.0 | 150.0 |
| Povidone (KOLLIDON ® 30 LP) | 8.0 | 8.0 | 8.0 | 8.0 |
| Stearic acid | 1.6 | 1.6 | 1.6 | 1.6 |
| Butylated hydroxytoluene | 0.20 | 0.20 | 0.2 | 0.2 |
| Dehydrated alcohol* | q.s. | q.s. | q.s. | q.s. |
| Active Layer | | | | |
| Methylphenidate HCl | 54.0 | 54.0 | 54.0 | 54.0 |
| Polyethylene oxide (POLYOX ® N80) | 135.0 | 135.0 | 135.0 | 135.0 |
| Povidone (KOLLIDON ® 30 LP) | 4.0 | 4.0 | 4.0 | 4.0 |

TABLE 12-continued

| Composition | Tablet 24 mg/dose | Tablet 27 mg/dose | Tablet 28 mg/dose | Tablet 29 mg/dose |
|---|---|---|---|---|
| Stearic acid | 0.9 | 0.9 | 0.9 | 0.9 |
| Butylated hydroxytoluene | 0.10 | 0.10 | 0.10 | 0.10 |
| Dehydrated alcohol* | q.s. | q.s. | q.s. | q.s. |
| Push Layer | | | | |
| Polyethylene oxide (POLYOX ® WSR 303) | 98.00 | 80.00 | 88.0 | 110.0 |
| Sodium chloride | 12.00 | 30.00 | 22.0 | NA |
| Povidone (KOLLIDON ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Dehydrated alcohol* | q.s. | q.s. | q.s. | q.s. |
| Total Core Weight | 478.0 | 478.0 | 478.0 | 478.0 |
| Functional Coating Layer | | | | |
| OPADRY ® CA clear (95:5) | 71.7 | 71.7 | 71.7 | 71.7 |
| Total Weight | 549.7 | 549.7 | 549.7 | 549.7 |

*Removed during process

Tablet 29 did not contain any amount of sodium chloride in the push layer; Tablet 24 contained about 10 wt % of sodium chloride, based on the total weight of the push layer; Tablet 28 contained about 18 wt % of sodium chloride, based on the total weight of the push layer; and tablet 27 contained about 25 wt % of sodium chloride, based on the in push layer. Trilayer methylphenidate tablets were made according to the procedure as per Example 5. Tablets 24, 27, 28, and 29, were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 11 shows the effect of the presence and amount of sodium chloride in push layer on lag time, release rate, and drug recovery from the tablet. The figure demonstrates that the presence of sodium chloride in the push layer reduces lag time and improves release rate and drug recovery at 24 hours. The figure further demonstrates that increasing the amount of sodium chloride in the push layer reduces lag time.

Example 12: Effect of Membrane Composition on Lag Time and Drug Recovery

The present Example provides two delayed release methylphenidate tablets. Tablet 30 contains OPADRY® CA with CA:PEG ratio of about 95:5 in the functional coating layer, while Tablet 31 contains OPADRY® CA with CA:PEG ratio of about 98:2 in the functional coating layer. The components of the two tablets are outlined below in Table 13.

TABLE 13

| Composition | Tablet 30 mg/dose | Tablet 31 mg/dose |
|---|---|---|
| Placebo Layer | | |
| Polyethylene oxide (POLYOX ® N205) | 150.0 | 150.0 |
| Povidone (KOLLIDON ® 30 LP) | 8.0 | 8.0 |
| Stearic acid | 1.6 | 1.6 |

TABLE 13-continued

| Composition | Tablet 30 mg/dose | Tablet 31 mg/dose |
|---|---|---|
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 135.0 | 135.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 80.00 | 80.00 |
| Sodium chloride | 30.00 | 30.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Core Tablet Weight | 478.0 | 478.0 |
| Functional Coated Layer | | |
| OPADRY ® CA clear | 71.7 | 71.7 |
| CA:PEG Ratio | 95:5 | 98:2 |
| Total Weight | 549.7 | 549.7 |

*Removed during process

Tablet 30 contained OPADRY® CA with CA:PEG ratio of about 95:5 in the functional coating layer; and Tablet 31 contained OPADRY® CA with CA:PEG ratio of about 98:2 in the functional coating layer. Trilayer methylphenidate tablets were made according to the procedure described as per Example 5. Tablets 30 and 31 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 12 shows effect of CA to PEG ratio in the functional coating layer on lag time and drug recovery of the tablets with 15% coating weight gain. The Figure demonstrates that increasing the amount of cellulose acetate in the functional coating layer, at a same coating weight gain, increases lag time and reduces drug recovery from the functional coated tablets.

Example 13: Effect of Coating Level and Presence of Sodium Chloride in Active Layer on Lag Time and Drug Recovery The present Example provides four delayed release methylphenidate tablets. The components of the four tablets are outlined below in Table 14.

TABLE 14

| Composition | Tablet 32 mg/dose | Tablet 33 mg/dose | Tablet 34 mg/dose | Tablet 32A mg/dose |
|---|---|---|---|---|
| Placebo Layer | | | | |
| Polyethylene oxide (POLYOX ® N205) | 150.0 | 150.0 | 75.0 | 150.0 |
| Povidone (KOLLIDON ® 30 LP) | 8.0 | 8.0 | 4.0 | 8.0 |
| Stearic acid | 1.6 | 1.6 | 0.8 | 1.6 |
| Butylated hydroxytoluene | 0.20 | 0.20 | 0.1 | 0.2 |
| Dehydrated alcohol* | q.s. | q.s. | q.s. | q.s. |

TABLE 14-continued

| Composition | Tablet 32 mg/dose | Tablet 33 mg/dose | Tablet 34 mg/dose | Tablet 32A mg/dose |
|---|---|---|---|---|
| Active Layer | | | | |
| Methylphenidate HCl | 54.0 | 54.0 | 54.0 | 54.0 |
| Polyethylene oxide (POLYOX ® N80) | 125.0 | 135.0 | 135.0 | 125.0 |
| Povidone (KOLLIDON ® 30 LP) | 4.0 | 4.0 | 4.0 | 4.0 |
| Stearic acid | 0.9 | 0.9 | 0.9 | 0.9 |
| Sodium chloride | 10.0 | NA | NA | 10.0 |
| Butylated hydroxytoluene | 0.10 | 0.10 | 0.1 | 0.10 |
| Dehydrated alcohol* | q.s. | q.s. | q.s. | q.s. |
| Push Layer | | | | |
| Polyethylene oxide (POLYOX ® WSR 303) | 88.0 | 88.0 | 88.0 | 88.0 |
| Sodium chloride | 22.0 | 22.0 | 22.0 | 22.0 |
| Povidone (KOLLIDON ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.5 | 1.5 |
| Dehydrated alcohol* | q.s. | q.s. | q.s. | q.s. |
| Core Tablet Weight | 478.0 | 478.0 | 398.0 | 478.0 |
| Functional Coating Layer | | | | |
| OPADRY ® CA clear (95:5) | 71.7 | 71.7 | 59.7 | 83.65 |
| Total Weight | 549.0 | 549.0 | 457.7 | 561.65 |

*Removed during process

Tablet 32 contained 15% coating weight gain of the functional coat layer and Tablet 32A contained 17.5% coating weight gain of the functional coat layer, based on the total weight of the uncoated tablets. Tablets 32 and 32A contained sodium chloride in the active layer; and Tablets 33 and 34 did not contain any amount of sodium chloride in the active layer. Trilayer methylphenidate tablets were made according to the procedure as per Example 5. Tablets 32, 32A, the 33, and 34 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 13 shows effect of coating weight gain/coating level of the semipermeable membrane on drug recovery and lag time. The Figure demonstrates that the tablet with a higher coating level (Tablet 32A) exhibits reduced drug recovery and increased lag time. The Figure further compares drug recovery between coated tablets at same coating weight gain, with and without sodium chloride in active layer. The Figure demonstrates that tablets containing sodium chloride in active layer exhibit improved drug recovery compared to tablets without sodium chloride in the active layer, both tablets at same coating weight gain. The Figure further shows that a decrease in amount of POLYOX® 205 present in placebo layer improves drug recovery.

Example 14: Effect of POLYOX® Grade in Placebo Layer, and Amount of Sodium Chloride in Active Layer on Lag Time and Drug Recovery The present Example provides three delayed release methylphenidate tablets comprising different amounts of sodium chloride in the active layer and/or different grades of POLYOX® in the placebo layer. The components of the three tablets are outlined below in Table 15.

TABLE 15

| Composition | Tablet 35 mg/dose | Tablet 36 mg/dose | Tablet 37 mg/dose |
|---|---|---|---|
| Placebo Layer | | | |
| Polyethylene oxide (POLYOX ® N205) | 150.0 | 150.0 | — |
| Polyethylene oxide (POLYOX ® 1105) | — | — | 150.0 |
| Povidone (KOLLIDON ® 30 LP) | 8.0 | 8.0 | 8.0 |
| Stearic acid | 1.6 | 1.6 | 1.6 |
| Butylated hydroxytoluene | 0.20 | 0.20 | 0.2 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 187.0 | 197.0 | 125.0 |
| Povidone (KOLLIDON ® 30 LP) | 4.0 | 4.0 | 4.0 |
| Stearic acid | 0.9 | 0.9 | 0.9 |
| Sodium chloride | 20.0 | 10.0 | 10.0 |
| Butylated hydroxytoluene | 0.10 | 0.10 | 0.1 |
| Dehydrated alcohol* | q.s. | q.s. | q.s. |
| Push Layer | | | |
| Polyethylene oxide (POLYOX ® WSR 303) | 88.0 | 88.0 | 88.0 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.5 |
| Butylated hydroxytoluene (BHT) | 0.20 | 0.20 | 0.2 |
| Red pigment blend | 1.50 | 1.50 | 1.5 |
| Dehydrated alcohol* | q.s. | q.s. | q.s. |
| Core Tablet Weight | 550.0 | 550.0 | 550.0 |
| Functional Coating Layer | | | |
| OPADRY ® CA clear (95:5) | 82.5 | 96.3 | 82.5 |
| Total Weight | 632.5 | 646.3 | 632.5 |

*Removed during process

Tablet 35 contained 187.0 mg of POLYOX® N80 and 20 mg of NaCl in the active layer. Tablet 36 contained 197.0 mg of POLYOX® N80 and 10 mg of NaCl in the active layer. Tablet 37 contained 125.0 mg of POLYOX® N80 and 10 mg of NaCl in the active layer. Tablets 35 and 37 contained 15 wt % coating weight gain and Tablet 36 contained about 17.5 wt % coating weight gain, based on the total weight of the uncoated trilayer coat. Trilayer methylphenidate tablets were made according to the procedure as per Example 5. Tablets 35, 36, and 37 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 14 compares lag time and drug recovery between Tablets 35 and 36 containing different amounts of sodium chloride in the active layer and different coating weight gains. Tablets 35 and 36 contained POLYOX® 205® in the placebo layer. Tablet 35, containing about 20 mg of sodium chloride in the active layer and with about 15 wt % coating weight gain, provides reduced lag time and higher drug recovery compared to tablet 36, containing about 10 mg of sodium chloride in the active layer and with 17.5 wt % coating weight gain. ry. The Figure further compares dissolution profiles of Tablets 35 and 37 containing POLYOX® 205 in the placebo layer and about 20 mg of sodium chloride in the active layer; and POLYOX® 1105 in the placebo layer and about 10 mg of sodium chloride in the active layer, respectively. Tablets 35 and 37 contained a coating weight gain of about 15 wt %, based on the total weight of the uncoated trilayer tablet core. Tablet 35 containing POLYOX® 205 and about 20 mg of sodium chloride provides reduced lag time and higher drug recovery compared to Tablet 37 containing POLYOX® 1105 and about 10 mg of sodium chloride.

Example 15: Effect of Push Layer Amount on Lag Time

The present Example provides two delayed release methylphenidate tablets comprising different amounts of POLYOX® in the push layer. The components of the two tablets are outlined below in Table 16.

TABLE 16

| Composition | Tablet 38 mg/dose | Tablet 39 mg/dose |
|---|---|---|
| Placebo Layer | | |
| Polyethylene oxide (POLYOX® N205) | 150.0 | 150.0 |
| Povidone (KOLLIDON® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX® N80) | 187.0 | 187.0 |
| Povidone (KOLLIDON® 30 LP) | 4.0 | 4.0 |
| Stearic acid | 0.9 | 0.9 |
| Butylated hydroxytoluene | 0.10 | 0.10 |
| Sodium chloride | 20.0 | 20.0 |
| Dehydrated alcohol* | q.s. | q.s. |
| Push Layer | | |
| Polyethylene oxide (POLYOX® WSR 303) | 80.00 | 62.00 |
| Sodium chloride | 22.00 | 15.5 |
| Povidone (KOLLIDON® 30 LP) | 12.0 | 8.4 |
| Stearic acid | 0.50 | 0.40 |
| Butylated hydroxytoluene (BHT) | 0.20 | 0.10 |
| Red pigment blend | 1.50 | 1.10 |
| Dehydrated alcohol* | q.s. | q.s. |
| Core Tablet Weight | 542.0 | 513.3 |
| Functional Coating Layer | | |
| OPADRY® CA clear (95:5) | 82.50 | 77.1 |
| Total Weight | 624.5 | 590.04 |

*Removed during process

Tablet 38 contained 116.2 mg of push layer (about 22 wt %, based on the total weight of the uncoated trilayer tablet core). Tablet 39 contained 87.5 mg of push layer (about 17 wt %, based on the total weight of the uncoated trilayer tablet core). Tablets 38 and 39 contained POLYOX® 205 in the placebo layer. Trilayer methylphenidate tablets were made according to the procedure described per Example 5. Tablets 38 and 39 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 15 shows effect of push layer amount on lag time in a compositions with a drug:polymer weight ratio in the active layer of about 20:80. The Figure demonstrates that for tablets containing POLYOX® 205 in the placebo layer, the lag time decreases with increase in push layer amount from about 17 wt % to about 22 wt %, based on the total weight of the uncoated trilayer tablet core.

Example 16: Effect of pH on Lag Time

The present Example provides a delayed release methylphenidate tablet comprising a placebo layer, a single active layer, a push layer, and a functional coating layer. The components of the tablet are outlined below in Table 17.

TABLE 17

Delayed Extended Release Methylphenidate HCl Tablet

| Composition | Tablet 40 mg/dose |
|---|---|
| Placebo layer | |
| Polyethylene oxide (POLYOX® N205) | 150.0 |
| Povidone (KOLLIDON® 30 LP) | 8.0 |
| Stearic acid | 1.6 |
| Butylated hydroxytoluene | 0.20 |
| Dehydrated alcohol* | q.s. |
| Active layer | |
| Methylphenidate HCl | 54.0 |
| Polyethylene oxide (POLYOX® N80) | 125.0 |
| Povidone (KOLLIDON® 30 LP) | 4.0 |
| Stearic acid | 0.9 |
| Butylated hydroxytoluene | 0.10 |
| Sodium chloride | 10.0 |
| Dehydrated alcohol* | q.s. |
| Push layer | |
| Polyethylene oxide (POLYOX® WSR 303) | 88.0 |
| Sodium chloride | 22.00 |
| Povidone (KOLLIDON® 30 LP) | 12.0 |
| Stearic acid | 0.50 |
| Butylated hydroxytoluene (BHT) | 0.10 |
| Red pigment blend | 1.60 |
| Dehydrated alcohol* | q.s. |
| Core Tablet Weight | 478.0 |
| Functional Coating Layer | |
| OPADRY® CA clear (95:5) | 71.7 |
| Total Weight | 549.7 |

*Removed during process

Trilayer methylphenidate tablets were made according to the procedure as per Example 5. Tablet 40 was tested for dissolution in about 900 ml of about 0.01N HCl, pH 4.5 acetate buffer, and pH 6.8 phosphate buffer, for up to 24 hours, using USP Apparatus II (Sinkers), at 50 rpm and 37° C. Percentage dissolution of the tablet was measured at 2, 4, 6, 8, 10, 12, 14, 16, 18, 20, 22, and 24 hours. FIG. 16 shows effect of pH on lag time in a tablet with a drug to polymer ratio of about 30:70. The figure demonstrates that the tablet exhibits minimal variability in lag time with variations in pH of the dissolution medium.

Example 17: Effect of Push Layer Amount on Lag Time

The present Example provides two delayed release methylphenidate tablets with different amounts of components in the push layer and the functional coating layer. The components of the two tablets are outlined below in Table 18.

TABLE 18

Delayed Extended Release Methylphenidate HCl Tablets

| Composition | Tablet 41 mg/dose | Tablet 42 mg/dose |
|---|---|---|
| Placebo Layer | | |
| Polyethylene oxide (POLYOX ® 1105) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 81.0 | 81.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Sodium chloride | 10.0 | 10.0 |
| Dehydrated alcohol* | q.s. | q.s. |
| Push Layer | | |
| Polyethylene oxide (POLYOX ® WSR 303) | 71.00 | 88.00 |
| Sodium chloride | 17.7 | 22.0 |
| Povidone (KOLLIDON ® 30 LP) | 12.0 | 8.4 |
| Stearic acid | 0.40 | 0.50 |
| Butylated hydroxytoluene (BHT) | 0.10 | 0.10 |
| Red pigment blend | 1.3 | 1.6 |
| Dehydrated alcohol* | q.s. | q.s. |
| Core Tablet Weight | 412.3 | 430.4 |
| Functional Coating Layer | | |
| OPADRY ® CA clear (95:5) | 61.5 | 65.1 |
| Total Weight | 473.8 | 495.5 |

*Removed during process

Tablet 41 contained 108.5 mg of push layer (about 26 wt % of push layer, based on the total weight of the uncoated tablet core) and Tablet 42 contained 120.6 mg of push layer (about 28 wt % of push layer, based on the total weight of the uncoated tablet core). Tablets 41 and 42 contained POLYOX® 11'05 in the placebo layer and contained about 15 wt % of the functional coating layer, based on the total weight of the uncoated tablet core. Trilayer methylphenidate tablets were made according to the procedure as per Example 5. Tablets 41 and 42 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 17 shows effect of push layer amount on lag time in tablets with drug to polymer ratio of about 40:60. The figure demonstrates that for tablets containing POLYOX® 1105 in the placebo layer, an increase in push layer amount, from about 26 wt % to about 28 wt %, based on the total weight of the uncoated tablet core, improves drug recovery without affecting the lag time.

Example 18: Effect of Coating Level and Placebo Layer Amount on Lag Time

The present Example provides four delayed release methylphenidate tablets. The components of the four tablets are outlined below in Table 19.

TABLE 19

| Composition | Tablet 43 mg/dose | Tablet 44 mg/dose | Tablet 43A mg/dose | Tablet 44A mg/dose |
|---|---|---|---|---|
| Placebo Layer | | | | |
| POLYOX ® 1105 | 150.0 | 100.0 | 150.0 | 100.0 |
| Povidone (Kollidon ® 30 LP) | 7.8 | 5.2 | 7.8 | 5.2 |
| Stearic acid | 1.5 | 1.0 | 1.5 | 1.0 |
| Butylated hydroxytoluene | 0.20 | 0.20 | 0.20 | 0.20 |
| Cab-O-Sil ® | 0.3 | 0.2 | 0.3 | 0.2 |
| Red pigment blend | 0.2 | 0.1 | 0.2 | 0.1 |
| Dehydrated alcohol* | q.s. | q.s. | q.s. | q.s. |
| Active Layer | | | | |
| Methylphenidate HCl | 54.0 | 54.0 | 54.0 | 54.0 |
| POLYOX ® N80 | 81.0 | 81.0 | 81.0 | 81.0 |
| Povidone (Kollidon ® 30 LP) | 8.0 | 8.0 | 8.0 | 8.0 |
| Stearic acid | 0.9 | 0.9 | 0.9 | 0.9 |
| Cab-O-Sil ® | 0.4 | 0.4 | 0.4 | 0.4 |
| Butylated hydroxytoluene | 0.10 | 0.10 | 0.10 | 0.10 |
| Sodium chloride | 10.0 | 10.0 | 10.0 | 10.0 |
| Dehydrated alcohol* | q.s. | q.s. | q.s. | q.s. |
| Push Layer | | | | |
| POLYOX ® WSR 303 | 88.00 | 88.00 | 88.00 | 88.00 |
| Sodium chloride | 22.0 | 22.0 | 22.0 | 22.0 |
| Povidone (Kollidone ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.5 | 1.5 | 1.5 | 1.5 |
| Cab-O-Sil ® | 0.3 | 0.3 | 0.3 | 0.3 |
| Dehydrated alcohol* | q.s. | q.s. | q.s. | q.s. |
| Core Tablet Weight | 438.9 | 385.6 | 438.9 | 385.6 |
| Functional CoatingLayer | | | | |
| Opadry CA clear (95:5) | 54.87 | 48.16 | 65.85 | 57.75 |
| Total Weight | 493.77 | 433.76 | 504.75 | 443.35 |

*Removed during process

Tablets 43 and 43A contained about 37 wt % of placebo layers, based on the total weight of the uncoated trilayer tablet core. Tablets 44 and 44A contained about 27 wt % of placebo layers, based on the total weight of the uncoated trilayer tablet core. Tablets 43 and 44 contained about 12.5% coating weight gain, and Tablets 43A and 44A contained about 15% coating weight gain, based on the total weight of the uncoated trilayer tablet core. Trilayer methylphenidate tablets were made according to the procedure as per Example 5. All tablets were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 18 shows effect of placebo layer amount and coating weight gain/coating level of the tablet, containing a drug:polymer weight ratio of about 40:60, on lag time. The Figure demonstrates that higher placebo layer amount and higher coating level on tablet core increases lag time.

Example 19: Effect of pH and Viscosity of Dissolution Medium on Lag Time

The present Example provides a delayed release methylphenidate tablet comprising a placebo layer, a single active layer, a push layer and a functional coating layer. The components of the tablet are outlined below in Table 20.

TABLE 20

| Composition | Tablet 45 mg/dose |
|---|---|
| Placebo Layer | |
| Polyethylene oxide (POLYOX ® 1105) | 100.0 |
| Povidone (KOLLIDON ® 30 LP) | 5.2 |
| Stearic acid | 1.0 |
| Butylated hydroxytoluene | 0.20 |
| Cab-O-Sil ® | 0.3 |
| Dehydrated alcohol* | q.s. |
| Active layer | |
| Methylphenidate HCl | 54.0 |
| Polyethylene oxide (POLYOX ® N80) | 81.0 |
| Povidone (KOLLIDON ®30 LP) | 8.0 |
| Stearic acid | 0.9 |
| Cab-O-Sil ® | 0.4 |
| Butylated hydroxytoluene | 0.10 |
| Sodium chloride | 10.0 |
| Dehydrated alcohol* | q.s. |
| Push layer | |
| Polyethylene oxide (POLYOX ® WSR 303) | 88.00 |
| Sodium chloride | 22.0 |
| Povidone (KOLLIDON ® 30 LP) | 12.0 |
| Stearic acid | 0.50 |
| Butylated hydroxytoluene (BHT) | 0.20 |
| Red pigment blend | 1.5 |
| Cab-O-Sil ® | 0.3 |
| Dehydrated alcohol* | q.s. |
| Core Tablet Weight | 385.6 |
| Functional Coated Layer | |
| OPADRY ® CA (95:5) | 48.16 |
| Total Weight | 433.76 |

*Removed during process

Trilayer methylphenidate tablets were made according to the procedure as per Example 5. Tablet 45 was tested for dissolution in about 900 ml of about 0.01N HCl, about 900 ml of pH 4.5 acetate buffer, and about 900 ml of pH 6.8 phosphate buffer, for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 19 compares dissolution rate of Tablet 45 at pH about 2, pH about 4.5, and pH about 6.8. The figure demonstrates that Tablet 45 exhibits minimal variability in lag time with variations in pH of the dissolution medium. FIG. 20 provides dissolution rate of Tablet 45 in dissolution mediums with different viscosities. The figure demonstrates that Tablet 45 exhibits minimal variability in lag time with variations in viscosity of the dissolution medium.

Example 20: Effect of Discrimination Methods on Lag Time

Dissolution profiles of Tablet 45 were compared using USP Apparatus II (Sinkers) at 50 rpm and 37° C. and using USP Apparatus III (Biodis) at 25 dpm and 37° C., mimicking effect of stomach shear on dissolution rate of the composition. Tablets 45 were placed individually in about 900 ml of about 0.01N HCl for up to 24 hours, in USP Apparatus II (Sinkers) at 50 rpm and 37° C., and in about 250 ml of about 0.01 N HCl for up to 24 hours, in USP Apparatus III (Biodis) at 25 dpm and 37° C. Percentage dissolution of the tablets was measured at 2, 4, 6, 8, 10, 12, 14, 16, 18, 20, 22, and 24 hours using the two methods. FIG. 21 compares dissolution rate of Tablet 45, containing a drug:polymer weight ratio of about 40:60, using the above two methods. The Figure demonstrates that there is no substantial change in lag time with changing hydrodynamics of the dissolution medium.

Example 21: Effect of Sodium Chloride Amount in the Placebo Layer on Lag Time and Release Rate The present Example provides three delayed release methylphenidate tablets comprising different amounts of sodium chloride in the placebo layer. The components of the three tablets are outlined below in Table 21.

TABLE 21

| Composition | Tablet 44 mg/dose | Tablet 46 mg/dose | Tablet 47 mg/dose |
|---|---|---|---|
| Placebo Layer | | | |
| Polyethylene oxide (POLYOX ® 1105) | 100.0 | 100.0 | 100.0 |
| Povidone (KOLLIDON ® 30 LP) | 5.2 | 5.2 | 5.2 |
| Stearic acid | 1.0 | 1.0 | 1.0 |
| Sodium chloride | — | 5.33 | 10.67 |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.7 | 390.83 | 396.27 |
| Functional Coating Layer | | | |
| OPADRY ® CA (95:5) | 48.16 | 48.83 | 49.49 |
| Total Weight | 433.86 | 439.66 | 445.76 |

*Removed during process

Tablet 44 did not contain any amount of sodium chloride in the placebo layer; Tablet 46 contained 5.33 mg of sodium chloride in the placebo layer; and Tablet 47 contained 10.67 mg of sodium chloride in the placebo layer. Trilayer methylphenidate tablets were made according to the procedure as per Example 5. Tablets 44, 46, and 47 were tested for dissolution in about 900 ml of about 0.01N HCl for up to 24 hours, using USP Apparatus II (Sinkers), at 50 rpm and 37°

C. Percentage dissolution of the tablets was measured at 2, 4, 6, 8, 10, 12, 14, 16, 18, 20, 22, and 24 hours. FIG. 22 shows effect of sodium chloride in placebo layer on lag time and release rate. The Figure demonstrates that presence of sodium chloride in placebo layer has negligible effect on lag time and release rate.

Example 22: Effect of POLYOX® Grade in Placebo Layer on Lag Time

The present Example provides three delayed release methylphenidate tablets comprising different grades of POLYOX® in the placebo layer. The components of the three tablets are outlined below in Table 22.

TABLE 22

Delayed Extended Release Methylphenidate HCl Tablets

| Composition | Tablet 44 mg/dose | Tablet 48 mg/dose | Tablet 49 mg/dose |
|---|---|---|---|
| Placebo Layer | | | |
| Polyethylene oxide (POLYOX ® 1105) | 100.0 | — | — |
| Polyethylene oxide (POLYOX ® N750) | | 100.0 | |
| Polyethylene oxide (POLYOX ® N80) | | | 100.0 |
| Povidone (KOLLIDON ® 30 LP) | 5.2 | 5.2 | 5.2 |
| Stearic acid | 1.0 | 1.0 | 1.0 |
| Sodium chloride | — | — | — |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.6 | 385.6 | 385.6 |
| Functional Coating Layer | | | |
| OPADRY ® CA (95:5) | 48.16 | 48.16 | 48.16 |
| Total Weight | 433.76 | 433.76 | 433.76 |

*Removed during process

Tablet 44 contained POLYOX® 1105 in the placebo layer; Tablet 48 contained POLYOX® N750 in the placebo layer; and Tablet 49 contained POLYOX® N80 in the placebo layer. Trilayer methylphenidate tablets were made according to the procedure as per Example 5. Tablets 44, 48, and 49 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 23 shows the effect of POLYOX® grade in placebo layer on lag time. The Figure compares lag time in compositions containing POLYOX® 80 (200K), POLYOX® 750 (300K), and POLYOX® 1105 (900K) in placebo layer. The Figure demonstrates that the average molecular weight of POLYOX® in the placebo layer should be at least about 300K to provide a lag time of at least about 6 hours.

Example 23: Effect of POLYOX® Grade in Push Layer on Lag Time

The present Example provides three delayed release methylphenidate tablets comprising different grades of POLYOX® in the push layer. The components of the three tablets are outlined below in Table 23.

TABLE 23

| Composition | Tablet 44 mg/dose | Tablet 50 mg/dose | Tablet 51 mg/dose |
|---|---|---|---|
| Placebo Layer | | | |
| Polyethylene oxide (POLYOX ® 1105) | 100.0 | — | — |
| Polyethylene oxide (POLYOX ® N750) | | 100.0 | |
| Polyethylene oxide (POLYOX ® N80) | | | 100.0 |
| Povidone (KOLLIDON ® 30 LP) | 5.2 | 5.2 | 5.2 |
| Stearic acid | 1.0 | 1.0 | 1.0 |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | — | — |
| Polyethylene oxide (POLYOX ® WSR 301) | — | 88.0 | — |
| Polyethylene oxide (POLYOX ® WSR Coagulant) | — | — | 88.0 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.6 | 385.6 | 385.6 |

TABLE 23-continued

| Composition | Tablet 44 mg/dose | Tablet 50 mg/dose | Tablet 51 mg/dose |
|---|---|---|---|
| Functional Coating Layer | | | |
| OPADRY ® CA (95:5) | 48.16 | 48.16 | 48.16 |
| Total Weight | 433.76 | 433.76 | 433.76 |

*Removed during process

Tablet 44 contained POLYOX® 1105 in the placebo layer and POLYOX® WSR 303 in the push layer; Tablet 50 contained POLYOX® N750 in the placebo layer and POLYOX® WSR 301 in the push layer; and Tablet 51 contained POLYOX® N80 in the placebo layer and POLYOX® WSR Coagulant in the push layer. Trilayer methylphenidate tablets were made according to the procedure as per Example 5. Tablets 44, 50, and 51 were tested for dissolution in about 900 ml of about 0.01N HCl for up to 24 hours, using USP Apparatus II (Sinkers), at 50 rpm and 37° C. Percentage dissolution of the tablets was measured at 2, 4, 6, 8, 10, 12, 14, 16, 18, 20, 22, and 24 hours. FIG. 24 shows the effect of POLYOX® grade/average molecular weight in push layer on release rate and drug recovery. The figure compares release rate and drug recovery in compositions containing POLYOX® WSR 303 (7M), POLYOX® WSR 301 (3M), and POLYOX® WSR Coagulant (5M) in push layer. The figure demonstrates that compositions containing POLYOX® N750 in the placebo layer and POLYOX® WSR 301 in the push layer or compositions containing POLYOX® N80 in the placebo layer and POLYOX® WSR Coagulant in the push layer provide higher drug recovery, compared to compositions containing POLYOX® 1105 in the placebo layer and POLYOX® WSR 303 in the push layer.

Example 24: Effect of Presence of a Wicking Agent and Sodium Chloride in Placebo Layer The present Example provides two delayed release methylphenidate tablets with and without sodium chloride, sylloid and croscarmellose sodium in the placebo layer. The components of the two tablets are outlined below in Table 24.

TABLE 24

| Composition | Tablet 52 mg/dose | Tablet 53 mg/dose |
|---|---|---|
| Placebo Layer | | |
| Polyethylene oxide (POLYOX ® 1105) | 100.0 | 100.0 |
| Povidone (KOLLIDON ® 30 LP) | 5.20 | 5.20 |
| Stearic acid | 1.00 | 1.0 |
| Butylated hydroxytoluene | 0.13 | 0.13 |
| Cab-O-Sil ® | 0.27 | 0.27 |
| Red Pigment blend | 0.07 | 0.07 |
| Croscarmellose sodium | 4.00 | — |
| Sylloid | 2.60 | — |
| Sodium chloride | 19.9 | — |
| Dehydrated alcohol* | q.s. | q.s. |
| Active layer | | |
| Methylphenidate HCl | 54.0 | 54.0 |
| Polyethylene oxide (POLYOX ® N80) | 81.0 | 36 |
| Povidone (KOLLIDON ® 30 LP) | 7.60 | 5.1 |
| Stearic acid | 0.90 | 0.55 |
| Cab-O-Sil ® | 0.40 | 0.28 |
| Butylated hydroxytoluene | 0.10 | 0.07 |
| Sodium chloride | 10.0 | 6.70 |
| Dehydrated alcohol* | q.s. | q.s. |
| Push layer | | |
| Polyethylene oxide (POLYOX ® WSR Coagulant) | 88.00 | 88.0 |
| Sodium chloride | 22.0 | 22.0 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.5 | 1.5 |
| Cab-O-Sil ® | 0.3 | 0.30 |
| Dehydrated alcohol* | q.s. | q.s. |
| Core Tablet Weight | 411.67 | 333.87 |
| Functional Coating | | |
| OPADRY ® CA (95:5) | 51.46 | 41.73 |
| Total Weight | 463.13 | 375.60 |

*Removed during process

Trilayer methylphenidate tablets were made according to the procedure as per Example 5. Tablets 52 and 53 were tested for dissolution in about 900 ml of about 0.01N HCl, using USP Apparatus II (Sinkers), at 50 rpm and 37° C. Percentage dissolution of the tablet was measured at 2, 4, 6, 8, 10, 12, 14, 16, 18, 20, 22, and 24 hours. FIG. 25 compares dissolution rate of Tablet 52 and Tablet 53. The Figure demonstrates that addition of a wicking agent and sodium chloride in the placebo layer, reduces drug recovery without affecting lag time.

Example 25: Dissolution in pH 6.8 Buffer, Using USP Apparatus II (Sinkers), Under Low-Volume, Low-RPM (Revolutions Per Minute) Conditions at 37° C.

The present Example provides four different delayed extended release methylphenidate HCl tablet compositions. The components of the different tablets are outlined below in Table 25.

TABLE 25

| Composition | Tablet 54 mg/dose | Tablet 55 mg/dose | Tablet 56 mg/dose | Tablet 57 mg/dose | Tablet 58 mg/dose |
|---|---|---|---|---|---|
| Placebo Layer | | | | | |
| Polyethylene oxide (POLYOX ® WSR 205) | 100.0 | 100.0 | 80.33 | 80.33 | |
| Polyethylene oxide (POLYOX ® WSR 1105) | NA | NA | NA | NA | 100.31 |
| Povidone (KOLLIDON ® 30 LP) | 5.30 | 5.30 | 4.26 | 4.26 | 5.22 |
| Sodium chloride | 7.60 | 7.60 | 6.11 | 6.11 | NA |
| Crospovidone | 7.40 | 7.40 | 5.94 | 5.94 | NA |
| Stearic acid | 1.00 | 1.00 | 0.80 | 0.80 | 1.00 |

TABLE 25-continued

| Composition | Tablet 54 mg/dose | Tablet 55 mg/dose | Tablet 56 mg/dose | Tablet 57 mg/dose | Tablet 58 mg/dose |
| --- | --- | --- | --- | --- | --- |
| Butylated hydroxytoluene | 0.15 | 0.15 | 0.12 | 0.12 | 0.13 |
| Red pigment blend | 0.05 | 0.05 | 0.04 | 0.04 | 0.07 |
| Cab-O-Sil ® (fumed silica) | 0.50 | 0.50 | 0.40 | 0.40 | 0.27 |
| Dehydrated alcohol* | q.s. | q.s. | q.s. | q.s. | q.s. |
| Active Layer | | | | | |
| Methylphenidate HCl | 54.00 | 54.00 | 54.00 | 54.00 | 54.00 |
| Polyethylene oxide (POLYOX ® N80) | 81.00 | 81.00 | 81.00 | 81.00 | 81.00 |
| Sodium chloride | NA | NA | NA | NA | 10.00 |
| Succinic acid | 10.00 | 6.3 | 6.3 | 6.3 | NA |
| Crospovidone | 6.30 | 6.30 | 6.30 | 6.30 | NA |
| Povidone (KOLLIDON ® 30 LP) | 5.00 | 5.00 | 5.00 | 5.00 | 10.00 |
| Stearic acid | 0.90 | 0.90 | 0.90 | 0.90 | 0.90 |
| Butylated hydroxytoluene | 0.10 | 0.10 | 0.10 | 0.10 | 0.10 |
| Cab-O-Sil ® (fumed silica) | 0.40 | 0.40 | 0.40 | 0.40 | 0.40 |
| Dehydrated alcohol* | q.s. | q.s. | q.s. | q.s. | q.s. |
| Push Layer | | | | | |
| Polyethylene oxide (POLYOX ® WSR 303) | NA | 88.00 | 70.97 | NA | 88.00 |
| Polyethylene oxide (POLYOX ® WSR Coagulant) | 88.00 | NA | NA | 70.97 | NA |
| Sodium chloride | 22.00 | 22.00 | 17.74 | 17.74 | 22.00 |
| Povidone (KOLLIDON ® 30 LP) | 11.50 | 11.50 | 9.28 | 9.28 | 11.50 |
| Stearic acid | 0.50 | 0.50 | 0.40 | 0.40 | 0.50 |
| Butylated hydroxytoluene (BHT) | 0.20 | 0.20 | 0.16 | 0.16 | 0.20 |
| Red pigment blend | 1.50 | 1.50 | 1.21 | 1.21 | 1.50 |
| Cab-O-Sil ® | 0.30 | 0.30 | 0.24 | 0.24 | 0.30 |
| Dehydrated alcohol* | q.s. | q.s. | q.s. | q.s. | q.s. |
| Total Core Weight | 403.70 | 400.00 | 352.0 | 352.0 | 387.4 |
| Functional Coating Layer | | | | | |
| OPADRY ® CA clear (95:5) | | 50.00 | 35.20 | | 48.425 |
| OPADRY ® CA clear (95:5) | 40.00 | | | 44.00 | |
| Total Tablet Weight | 443.07 | 450.0 | 387.2 | 396.0 | 435.825 |

*Removed during process

Tablets 54-57 contained sodium chloride and crospovidone, as an osmogen and a wicking agent respectively, in the placebo layer; succinic acid and crospovidone, as a stabilizing agent and an osmogen, respectively, in the active layer; and sodium chloride as an osmogen in the push layer. Tablet 58 did not contain sodium chloride and crospovidone in the placebo layer, and succinic acid and crospovidone in the active layer. The tablets were made according to the following manufacturing procedure.

Manufacturing Procedure

Separate blends of placebo layer, active layer, and push layer were made as per Tablets 54-58.

1. Preparation of placebo blend: Povidone and BHT were added to dehydrated alcohol in a suitable stainless-steel container and mixed to obtain a clear solution; the resulting solution was sprayed onto a blend of polyethylene oxide, sodium chloride, crospovidone, and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

2. Preparation of active layer blend: Povidone and BHT were added to dehydrated alcohol in a suitable stainless-steel container and mixed to obtain a clear solution; the resulting solution was sprayed onto a blend of methylphenidate HCl, polyethylene oxide, succinic acid, and crospovidone taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

3. Preparation of push layer blend: Povidone and BHT were added to dehydrated alcohol in a suitable stainless-steel container and mixed to obtain a clear solution; the resulting solution was sprayed onto a blend of polyethylene oxide, sodium chloride, and red pigment blend taken in a high shear mixer; the resulting granules were dried at a temperature of about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and further mixing for 3 minutes.

4. Required amount of each blend (as per Tablets 54-58) was filled into the die and then compressed as tri-layer tablet composition, as per Table 20.

5. OPADRY® CA was added to a stainless-steel container charged with acetone and water (about 92:8) and mixed for not less than 60 minutes to obtain a clear solution. The tablets from step #4 were taken in a coating pan and coated with the solution from step #5 until the target % weight gain was obtained and cured at a product temperature of 40° C. for one hour.

6. A hole/orifice of about 0.3 mm was drilled into the coating at the placebo layer end of the tablet.

FIG. 26 provides dissolution profiles of Tablets 54, 57, and 58 in 5 ml of pH 6.8 buffer, using USP Apparatus II (Sinkers), at 5 rpm and 37° C. (low-volume, low-RPM condition). Percentage dissolution of the tablets was measured at 2, 4, 6, 8, 10, 12, 14, 16, 18, 20, 22, and 24 hours. FIG. 26 demonstrates that Tablet 54, with about 10% coating weight gain, based on the total weight of the uncoated tablet core, provides an improved release rate and improved drug recovery compared to Tablets 57 and 58, with about 12.5% coating weight gain, based on the total weight of the uncoated tablet core. The figure further demonstrates that Tablets 54 and 57 containing higher amount of pore former (Polyethylene glycol present in OPADRY® CA clear (90:10)) in the coating layer provide faster drug release compared to Tablet 58 containing less amount of pore former in OPADRY® CA clear (95:5) in the coating layer. The figure also demonstrates that Tablet 58 containing POLYOX® 1105 in the placebo layer and POLYOX® WSR 303 in the push layer provides longer lag time compared to Tablets 54 and 57 containing POLYOX® 205 in placebo layer and POLYOX® WSR coagulant in the push layer.

Example 26: Oral Bioavailability of Methylphenidate HCl from Osmotic-Controlled Compositions of the Disclosure A single dose pharmacokinetic (PK) study was conducted in healthy volunteers under fed conditions to evaluate and compare the PK performance of delayed extended release methylphenidate HCl compositions of the disclosure with a marketed extended release methylphenidate HCl product (CONCERTA®). An open label, balanced, randomized, three-treatment, six-sequence three-period, single oral dose, three-way crossover bioequivalence study of Tablets 54 and 57 with CONCERTA® (methylphenidate hydrochloride extended-release tablets), 54 mg, was conducted in normal, healthy, adult, human subjects under fed conditions.

TABLET 26

| Pharmacokinetic Parameters (units) | Mean ± SD (CV %) (N = 18) | | |
|---|---|---|---|
| | Tablet 54 | Tablet 57 | Reference Product (54 mg) |
| Cmax | 22.0 (44) | 17.4 (36) | 21.0 (35.6) |
| Tmax | 12.0 (15.6) | 14.2 (23) | 9.1 (19.5) |
| AUC0-∞ | 219.0 (51) | 222.0 (40) | 296.0 (38) |

The data from this study (Table 26/FIG. 27) demonstrates that Tablet 54 provides a lag time of about 7 hours and Cmax of about 22 ng at 12 hours post administration.

Example 27: Effect of the Number of Orifices on the Placebo Layer End of the Functional Coated Tablets on % Variability (Relative Standard Deviation)

Table 27 provides % relative standard deviation (% RSD) for Tablet 54A containing a coating with one orifice with 0.6 mm diameter; Tablet 54B containing a coating with two orifices, each with 0.6 mm diameter; and Tablet 54C containing a coating with one orifice with 1.2 mm diameter. The tablets were tested for dissolution in 900 ml of 0.01 N HCl for up to 24 hours, using USP Apparatus II (Sinkers), at 50 rpm and 37° C. The % RSD was determined based on variations in dissolution among a set of three tablets each, for Tablets 54A, 54B, and 54C, at different time points. The table shows that Tablet 54B containing two orifices, each with 0.6 mm diameter; and Tablet 54C containing one orifice with 1.2 mm diameter show significantly reduced % RSD among a set of three tablets, compared to Tablet 54A containing one orifice with 0.6 mm diameter

TABLE 27

| | Tablet 54A (10% coat-0.6 mm, 1 hole) | | Tablet 54B (10% coat-0.6 mm, 2 holes) | | Tablet 54C (10% coat-1.2 mm, 1 hole) | |
|---|---|---|---|---|---|---|
| Time (hrs) | % Dissolved | % RSD | % Dissolved | % RSD | % Dissolved | % RSD |
| 0 | 0.0 | 0.0 | 0.0 | 0.0 | 0.0 | 0.0 |
| 6 | 12.0 | 43.1 | 10.0 | 21.5 | 10.0 | 14.8 |
| 7 | 21.0 | 19.6 | 24.0 | 15.0 | 24.0 | 29.2 |
| 8 | 33.0 | 30.2 | 44.0 | 13.0 | 41.0 | 25.7 |
| 9 | 48.0 | 36.3 | 65.0 | 11.5 | 58.0 | 18.9 |
| 10 | 63.0 | 30.2 | 82.0 | 8.5 | 73.0 | 11.7 |
| 12 | 82.0 | 14.1 | 97.0 | 4.6 | 90.0 | 3.2 |

Example 28: Additional Delayed Release Compositions of the Disclosure

The present example provides 4 different delayed extended release compositions. Compositions of each of the tablets tested are shown in Table 28.

TABLE 28

| Composition | Tablet 59 mg/dose | Tablet 60 mg/dose | Tablet 61 mg/dose | Tablet 62 mg/dose |
|---|---|---|---|---|
| Placebo Layer | | | | |
| Polyethylene oxide (POLYOX ® WSR 205) | 164.00 | 164.00 | 164.00 | 82.00 |
| Povidone (KOLLIDON ® 30 LP) | 8.50 | 8.50 | 8.5 | 4.25 |
| Sodium chloride | 25.00 | 25.00 | 25.00 | 15.00 |
| Stearic acid | 1.50 | 1.50 | 1.5 | 1.00 |
| Butylated hydroxytoluene | 0.25 | 0.25 | 0.25 | 0.15 |
| Red pigment blend | 0.10 | 0.10 | 0.10 | 0.05 |
| Cab-O-Sil ® (fumed silica) | 0.75 | 0.75 | 0.75 | 0.50 |
| Active Layer | | | | |
| Methylphenidate HCl | | 54.00 | 54.00 | |
| Hydrocortisone | | | | 20 |
| Armodafinil | | | 50 | |
| Polyethylene oxide (POLYOX ® N80) | 81.00 | 33.67 | 33.67 | 33.67 |
| Succinic acid | 10.00 | 4.09 | 10.00 | — |
| Crospovidone | 6.30 | 4.09 | 6.30 | 4.09 |
| Povidone (KOLLIDON ® 30 LP) | 5.00 | 3.25 | 5.00 | 3.25 |
| Stearic acid | 0.90 | 0.58 | 0.90 | 0.58 |
| Butylated hydroxytoluene | 0.10 | 0.06 | 0.10 | 0.06 |
| Cab-O-Sil ® (fumed silica) | 0.40 | 0.26 | 0.40 | 0.26 |

TABLE 28-continued

| Composition | Tablet 59 mg/dose | Tablet 60 mg/dose | Tablet 61 mg/dose | Tablet 62 mg/dose |
|---|---|---|---|---|
| Push Layer | | | | |
| Polyethylene oxide (POLYOX ® WSR Coagulant) | 88.00 | 88.00 | 88.00 | 88 |
| Sodium chloride | 22.00 | 22.00 | 22.00 | 22.00 |
| Povidone (KOLLIDON ® 30 LP) | 11.50 | 11.50 | 11.50 | 11.50 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Cab-O-Sil ® | 0.30 | 0.30 | 0.30 | 0.30 |
| Total Core Weight | 481.80 | 424.10 | 430.17 | 288.86 |
| Functional Coating Layer | | | | |
| OPADRY ® CA clear (90:10) | 48.18 | 42.41 | 43.10 | 28.86 |
| Total Tablet Weight | 529.98 | 466.51 | 473.27 | 317.72 |

Trilayer Tablet 59 and Tablet 60 were made by following the procedure as outlined in Example 25. Trilayer Tablet 61 and Tablet 62 are made by following the procedure as outlined in Example 25.

The present disclosure is not to be limited in scope by the specific embodiments described herein. Indeed, various modifications of the disclosure in addition to those described herein will become apparent to those skilled in the art from the foregoing description. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions, and protocols are cited throughout this application, the disclosures of which are incorporated herein by reference in their entireties for all purposes.

What is claimed is:

1. An oral pharmaceutical composition providing delayed release of a of a drug, the composition comprising:
   a) a multilayer core comprising a placebo layer, an active layer, and a push layer, wherein:
      (i) the placebo layer comprises at least one polyethylene oxide polymer having an average molecular weight of from about 400K Da to about 900K Da,
      (ii) the active layer comprises at least one drug, and at least one polyethylene oxide polymer having an average molecular weight of less than or equal to 300K Da,
      (iii) the push layer comprises at least one polyethylene oxide polymer having an average molecular weight of greater than or equal to 1M Da; and
   b) a semipermeable membrane, containing at least one orifice and surrounding the core,
   wherein the drug is selected from the group consisting of CNS-acting drugs, cardiovascular drugs, anti-infectives, analgesics, anesthetics, antiarthritics, anticholinergics, anti-asthmatics, antidepressants, antimigraine drugs, antiparkinson drugs, anticonvulsants, armodafinil, modafinil, calcium channel blockers, beta blockers, decongestant, sedatives, antihypertensives, ACE inhibitors, antidiabetics, and tranquilizers,
   wherein the layers in the multilayer core are placed in the following order: the placebo layer in fluid communication with the at least one orifice in the semipermeable membrane; the active layer; and the push layer facing away from the at least one orifice.

2. The composition of claim 1, wherein the semipermeable membrane comprises a water-insoluble polymer and a water-soluble pore former.

3. The composition of claim 2, wherein the water-insoluble polymer in the semipermeable membrane is selected from the group consisting of cellulose acetate, cellulose acetate butyrate, cellulose triacetate, and combinations thereof.

4. The composition of claim 2, wherein the water-soluble pore former is selected from the group consisting of polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

5. The composition of claim 2, wherein the water-soluble pore former is a plasticizer selected from the group consisting of polyethylene glycol, triethyl citrate, triacetin, diethyl tartrate, and combinations thereof.

6. The composition of claim 1, wherein the composition when tested for dissolution in about 900 ml of a dissolution medium comprising about 0.01N HCl, using USP Apparatus II (sinkers) at about 50 rpm and about 37° C., provides a lag time of at least 4 hours.

7. The composition of claim 6, wherein, during the lag time, the composition releases no more than 10% of the drug.

8. The composition of claim 1, wherein the push layer further comprises an osmogen.

9. The composition of claim 8, wherein the osmogen is selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, and combinations thereof.

10. The composition of claim 8, wherein the osmogen is present in an amount of from about 5 wt % to about 40 wt % of the push layer.

11. The composition of claim 1, wherein the placebo layer is present in an amount of from about 10 wt % to about 60 wt %, based on the total weight of the multilayer core.

12. The composition of claim 1, wherein the polyethylene oxide polymer in the placebo layer is present in an amount of from about 50 wt % to about 99 wt % of the placebo layer.

13. The composition of claim 1, wherein the active layer further comprises a surfactant selected from the group consisting of esters of fatty acids; sorbitan fatty acid esters; polyethylene glycol fatty acid esters; polyethylene glycol esters and polyethylene glycol ethers;
and polyethoxylated carboxylic acids, PEG-7 hydrogenated castor oil, and PEG-30 dipolyhydroxystearate; block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; polyoxyl 40 stearate, and any combinations thereof.

14. An oral pharmaceutical composition providing a pulsatile release of a first drug and a second drug, the composition comprising:
   a) a multilayer core comprising layers in the following order:
   (i) a first placebo layer comprising at least one polyethylene oxide polymer having an average molecular weight of from about 400,000 Da to about 900,000 Da,
   (ii) a first active layer comprising a first drug, and at least one polyethylene oxide polymer having a molecular weight of less than or equal to 300,000 Da,
   (iii) a second placebo layer comprising at least one polyethylene oxide polymer having an average molecular weight of from about 300,000 Da to about 900,000 Da,
   (iv) a second active layer comprising layer comprising a second drug and at least one polyethylene oxide polymer having a molecular weight of less than or equal to 300,000 Da, and
   (v) a push layer comprising at least one polyethylene oxide polymer having an average molecular weight of greater than or equal to 1000,000 Da, and
   b) a semipermeable membrane surrounding the multilayer core, wherein the semipermeable membrane comprises at least one orifice facing the first placebo layer; wherein the layers in the multilayer core are placed in the following order: the first placebo layer in fluid communication with the at least one orifice in the semipermeable membrane; the first active layer; the second placebo layer; the second active layer; and the push layer facing away from the at least one orifice,
   wherein the first drug and the second drug are selected from the group consisting of amphetamines, methylphenidate, diltiazem, carbamazepine, metoprolol, oxprenolol, nifedipine, albuterol, phenylpropanolamine, pseudoephedrine, chlorpheniramine maleate, prazosin, doxazosin, verapamil, oxybutynin chloride, isradipine, hydromorphone, paliperidone, modafinil, armodafinil, liothyronine, oseltamivir (Tamiflu), rifamycin, and glipizide.

15. The composition of claim 14, wherein the pulsatile release comprises release of a first pulse containing the first drug, and a second pulse containing the second drug, and wherein the release of first pulse containing the first drug is delayed by at least about 4 hours.

16. The composition of claim 15, wherein the composition further comprises an immediate release drug layer containing a third drug for immediate release and surrounding the semipermeable membrane.

17. An oral pharmaceutical composition comprising a multilayer core comprising a drug for delayed release; a semipermeable membrane containing at least one orifice and surrounding the multilayer core; and an immediate release drug layer containing a drug for immediate release and surrounding the semipermeable membrane, wherein the multilayer core comprises a placebo layer, an active layer, and a push layer, wherein:
   (i) the placebo layer comprises at least one polyethylene oxide polymer having an average molecular weight of from about 400,000 Da to about 900,000 Da,
   (ii) the active layer comprises a drug for delayed release, and at least one polyethylene oxide polymer having an average molecular weight of less than or equal to 300,000 Da, and
   (iii) the push layer comprises at least one polyethylene oxide polymer having an average molecular weight of greater than or equal to 1000,000 Da;
   wherein the layers in the multilayer core are placed in the following order: the placebo layer in fluid communication with the at least one orifice in the semipermeable membrane; the active layer; and the push layer facing away from the orifice,
   wherein the drug for delayed release is selected from the group consisting of amphetamines, methylphenidate, diltiazem, carbamazepine, metoprolol, oxprenolol, nifedipine, albuterol, phenylpropanolamine, pseudoephedrine, chlorpheniramine maleate, prazosin, doxazocin, verapamil, oxybutynin chloride, isradipine, hydromorphone, paliperidone, modafinil, armodafinil, liothyronine, oseltamivir (Tamiflu), rifamycin, and glipizide.

18. The composition of claim 17, and wherein the release of the drug from the multilayer core is delayed by at least 4 hours, when tested for dissolution in about 900 ml of a dissolution medium comprising about 0.01N HCl, using USP Apparatus II (sinkers) at about 50 rpm and about 37° C.

19. The composition of claim 18, wherein during the lag time, the composition releases no more than 10% of the drug present in the multilayer core.

20. A method of treating a condition that requires release of a drug at a rhythm, that matches circadian rhythm of an individual being treated, the method comprising administering to a subject in need thereof, an oral pharmaceutical composition comprising:
   a) a multilayer core comprising a placebo layer, an active layer, and a push layer, wherein:
   (i) the placebo layer comprises at least one polyethylene oxide polymer having an average molecular weight of from about 400K Da to about 900K Da, or intermediate values thereof,
   (ii) the active layer comprises at least one drug, and at least one polyethylene oxide polymer having an average molecular weight of less than or equal to 300K Da,
   (iii) the push layer comprises at least one polyethylene oxide polymer having an average molecular weight of greater than or equal to 1M Da; and
   b) a semipermeable membrane, containing at least one orifice and surrounding the core,
   wherein the drug is selected from the group consisting of CNS-acting drugs, cardiovascular drugs, anti-infectives, analgesics, anesthetics, antiarthritics, anticholinergics, anti-asthmatics, antidepressants, antimigraine drugs, armodafinil, modafinil, calcium channel blockers, beta blockers, decongestant, antihypertensives, and ACE inhibitors,
   wherein the layers in the multilayer core are placed in the following order: the placebo layer in fluid communication with the at least one orifice in the semipermeable membrane; the active layer; and the push layer facing away from the at least one orifice,
   wherein the composition is taken at night before going to bed and the drug release is delayed for at least about 4 hours.

* * * * *